US012667088B2

(12) United States Patent
Kang et al.

(10) Patent No.: US 12,667,088 B2
(45) Date of Patent: *Jun. 30, 2026

(54) ANIMAL MODEL OF BRAIN TUMOR AND MANUFACTURING METHOD OF ANIMAL MODEL

(71) Applicants: KOREA ADVANCED INSTITUTE OF SCIENCE AND TECHNOLOGY, Daejeon (KR); YONSEI UNIVERSITY, UNIVERSITY—INDUSTRY FOUNDATION (UIF), Seoul (KR)

(72) Inventors: Seok Gu Kang, Suwon-si (KR); Jeong Ho Lee, Daejeon (KR); Joo Ho Lee, Daejeon (KR); Jeong Eun Lee, Daejeon (KR)

(73) Assignees: KOREA ADVANCED INSTITUTE OF SCIENCE AND TECHNOLOGY, Daejeon (KR); YONSEI UNIVERSITY, UNIVERSITY—INDUSTRY FOUNDATION (UIF), Seoul (KR)

( * ) Notice: Subject to any disclaimer, the term of this patent is extended or adjusted under 35 U.S.C. 154(b) by 801 days.

This patent is subject to a terminal disclaimer.

(21) Appl. No.: 17/956,771

(22) Filed: Sep. 29, 2022

(65) Prior Publication Data
US 2023/0232794 A1    Jul. 27, 2023

Related U.S. Application Data

(63) Continuation-in-part of application No. 16/050,006, filed on Jul. 31, 2018, now Pat. No. 11,490,603.

(30) Foreign Application Priority Data

Feb. 6, 2018    (KR) ........................ 10-2018-0014741

(51) Int. Cl.
*A01K 67/0276*        (2024.01)

(52) U.S. Cl.
CPC .... *A01K 67/0276* (2013.01); *A01K 2217/075* (2013.01); *A01K 2217/15* (2013.01); *A01K 2227/105* (2013.01); *A01K 2267/0331* (2013.01)

(58) Field of Classification Search
CPC .......... A01K 67/0276; A01K 2217/075; A01K 2217/15; A01K 2227/105; A01K 2267/0331; A01K 2217/072; A01K 67/0275; C12N 15/1135; C12N 2310/20; C12N 9/16; C07K 14/4702; C07K 14/4748; C07K 14/71; C12Y 301/03067
See application file for complete search history.

(56) References Cited

U.S. PATENT DOCUMENTS

2010/0100974 A1    4/2010    Charest

FOREIGN PATENT DOCUMENTS

| JP | 2009-523709 | 6/2009 |
| KR | 10-1492436 | 2/2015 |
| KR | 10-2018-0024262 | 3/2018 |

OTHER PUBLICATIONS

Goldstein et al. "Variation in zygotic CRISPR/Cas9 gene editing outcomes generates novel reporter and deletion alleles at the Gdf11 locus"Sci Rep.Dec. 9, 2019;9(1):18613. (Year: 2019).*
McCarty et al. "Multiplexed CRISPR technologies for gene editing and transcriptional regulation." Nature Communications vol. 11, Article No. 1281 (2020) (Year: 2020).*
Yin et al. "Generation of an MC3R knock-out pig by CRSPR/Cas9 combined with somatic cell nuclear transfer (SCNT) technology." Lipids Health Dis. May 28, 2019;18(1):122. d (Year: 2019).*
He et al. "Use of CRISPR/Cas9 technology efficiently targetted goat myostatin through zygotes microinjection resulting in double-muscled phenotype in goats."Biosci Rep . Nov. 1, 20183;38(6): BSR20180742 (Year: 2018).*
Anh et al. "Epidermal growth factor receptor (EGFR) and EGFRvIII in glioblastoma (GBM): signaling pathways and targeted therapies. "Oncogene. Jan. 11, 2018;37(12):1561-1575. (Year: 2018).*
You et al. "Effects of Melanocortin 3 and 4 Receptor Deficiency on Energy Homeostasis in Rats".: Sci Rep. Oct. 7, 2016;6:34938. (Year: 2016).*
Vesikansa, A. "Unraveling of Central Nervous System Disease Mechanisms Using CRISPR Genome Manipulation."J Cent Nerv Syst Dis. Jul. 10, 2018;10:1179573518787469 (Year: 2018).*
Joo Ho Lee, "Human Glioblastoma Arises from the Distant Subventricular Zone Normal-appearing but Harboring Tumor-initiating Mutations", The 13th KOGO Winter Symposium 2017, Poster Presentation, Feb. 8, 2017.
Joo Ho Lee, Md, Ms, Korea Advanced Institute of Science and Technology, Daejeon, Republic of Korea., Abstract 2455, "Human glioblastoma arises from the distant subventricular zone normal appearing but harboring tumor-initiating mutations.", Travel Awards, Awardee list of Mar. 9, 2016, AACR Annual Meeting 2017, Washington DC, Apr. 1, 2017.

(Continued)

*Primary Examiner* — Titilayo Moloye
(74) *Attorney, Agent, or Firm* — LEX IP MEISTER, PLLC

(57) ABSTRACT

The present invention relates to a brain tumor animal model that directly reflects the phenomenon in a human patient and a method of preparing the same, and more specifically, a brain tumor animal model that mutations are introduced into p53, Pten, and EGFR genes, a screening method of a therapeutic agent for a brain tumor using the animal model, and a preparing method thereof.

5 Claims, 34 Drawing Sheets

Specification includes a Sequence Listing.

(56)                    References Cited

OTHER PUBLICATIONS

Seok Gu Kang, "Human glioblastoma arises from normal subventricular zone harboring tumor-initiating mutations", 5th Quadrennial Meeting of the World Federation of Neuro-Oncology Societies (WFNOS), May 5, 2017.

Joo Ho Lee, "Human glioblastoma arises from the distant subventricular zone normal-appearing but harboring tumor-initiating mutations", SY6-02, Symposium 6, APCC 2017 Seoul, Jun. 22, 2017.

Seok Gu Kang, "Starting point of human glioblastoma, IDH-wildtype: subventricular zone", ASNO 2017 The 14th Meeting of the Asian Society for Neuro-Oncology, Oct. 30, 2017.

Seok Gu Kang, "The origin of human glioblastoma, Firework pattern glioblastoma from subventricular zone", SNO 22nd Annual Meeting and Education Day of the Society for Neuro-Oncology, Nov. 17, 2017.

NCBI, "Mus musculus targeted KO-first, conditional ready, lacZ-tagged mutant allele Trp53:tm1a (EUCOMM)Hmgu; transgenic", Genbank accession No. JN964617.1.

NCBI, "Mus musculus PTENbeta (PTEN) mRNA, complete cds", Genbank accession No. KX421108.1, 2017.

Alexandru Oprita et al., "Updated Insights on EGFR Signaling Pathways in Glioma", Int. J. Mol. Sci. 2021, 22, 587. Jan. 8, 2021. https://doi.org/10.3390/ijms22020587.

Jeffrey C. Lee et al., "Epidermal Growth Factor Receptor Activation in Glioblastoma through Novel Missense Mutations in the Extracellular Domain", PLoS Med 3(12): e485. Dec. 19, 2006. doi:10.1371/journal.pmed.0030485.

Patrick J. Cimino et al., "A Wide Spectrum of EGFR Mutations in Glioblastoma is Detected by a Single Clinical Oncology Targeted Next-Generation Sequencing Panel", Exp Mol Pathol. Jun. 2015 ; 98(3): 568-573. doi:10.1016/j.yexmp.2015.04.006.

Joo Ho Lee et al., "Human Glioblastoma Arises from the Distant Subventricular Zone Normal-appearing but Harboring Tumor-initiating Mutations", The 13th KOGO Winter Symposium 2017, Feb. 8, 2017, Poster Presentation only. total 6 pages.

Joo Ho Lee et al., Md, Ms, Korea Advanced Institute of Science and Technology, Daejeon, Republic of Korea., Abstract 2455, "Human glioblastoma arises from the distant subventricular zone normal appearing but harboring tumor-initiating mutations.", AACR Annual Meeting 2017, Washington DC, Apr. 1-5, 2017, Abstract only, total 215 pages.

Seok Gu Kang et al., "Human glioblastoma arises from normal subventricular zone harboring tumor-initiating mutations", 5th Quadrennial Meeting of the World Federation of Neuro-Oncology Societies (WFNOS), May 5, 2017, Abstract only, total 4 pages.

* cited by examiner

【FIG. 1】
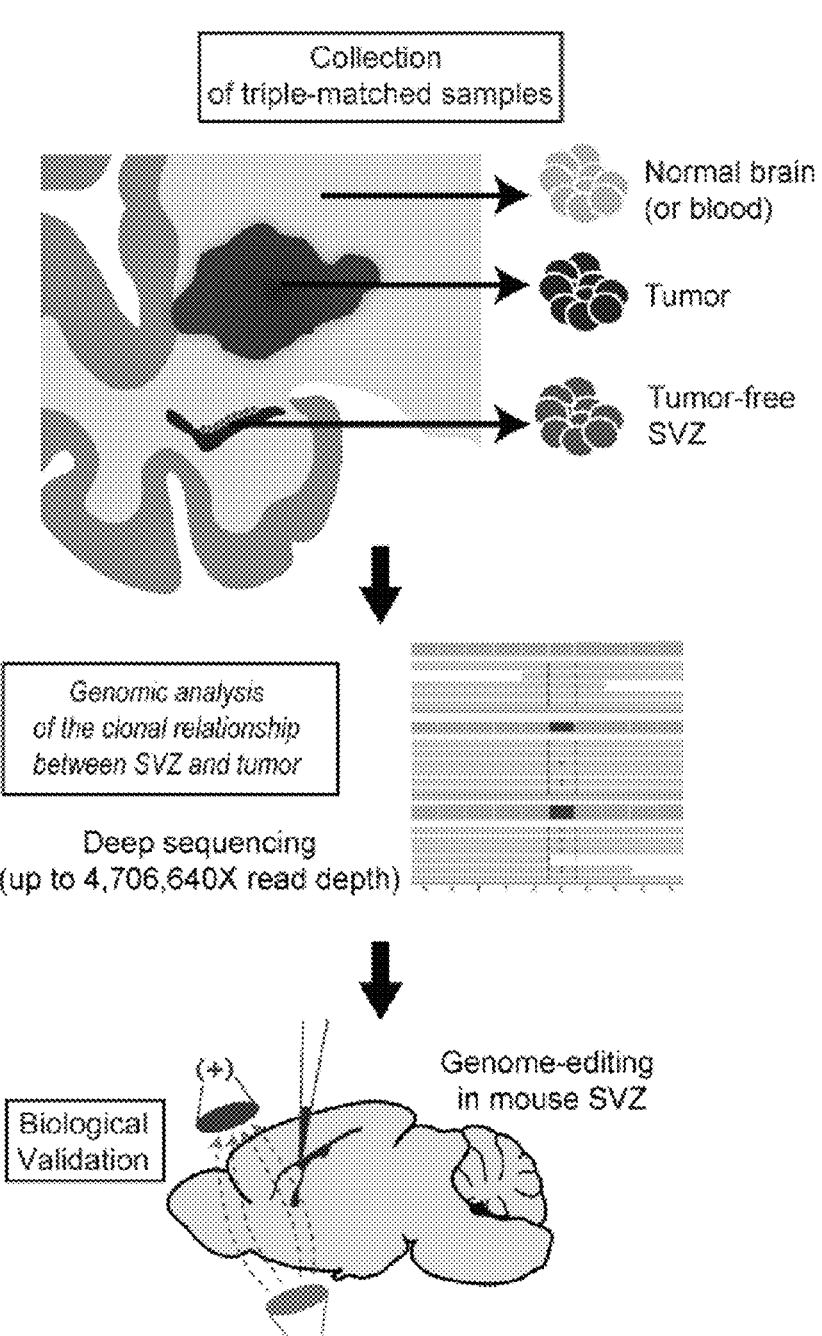

【FIG. 2】
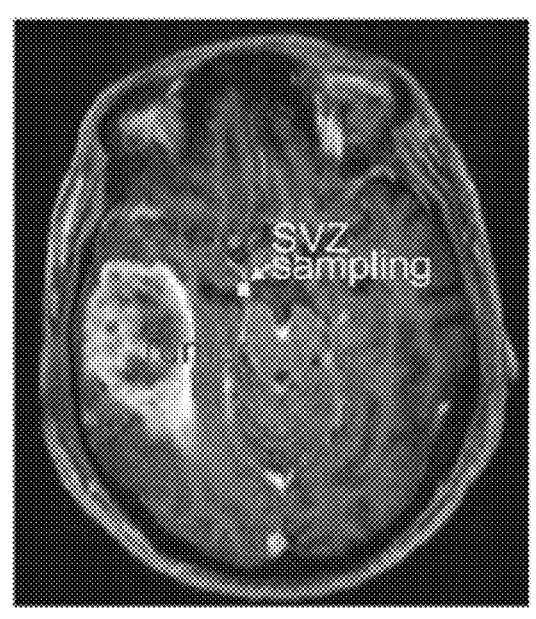
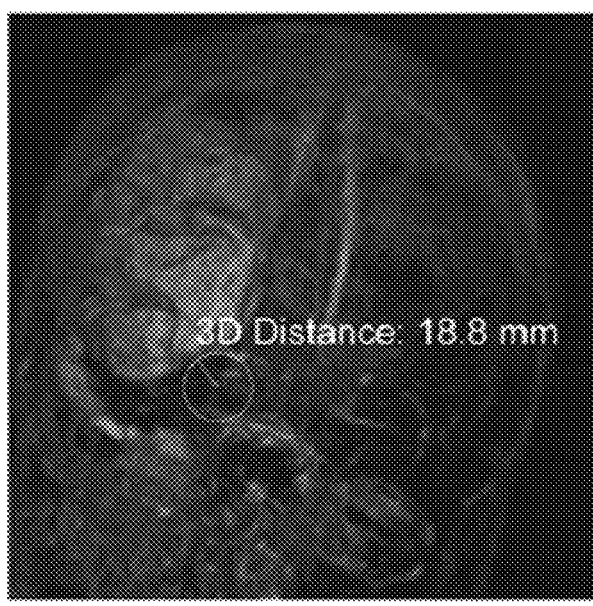

【FIG. 3】
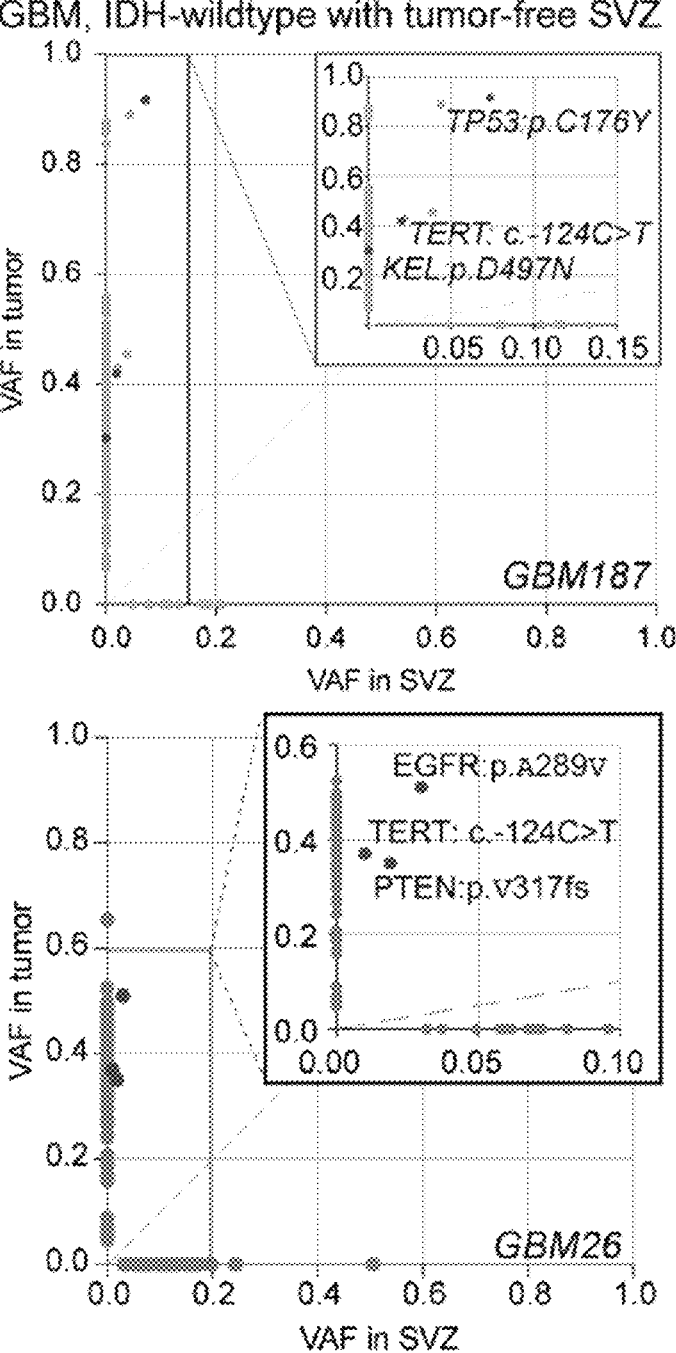

【FIG. 4】
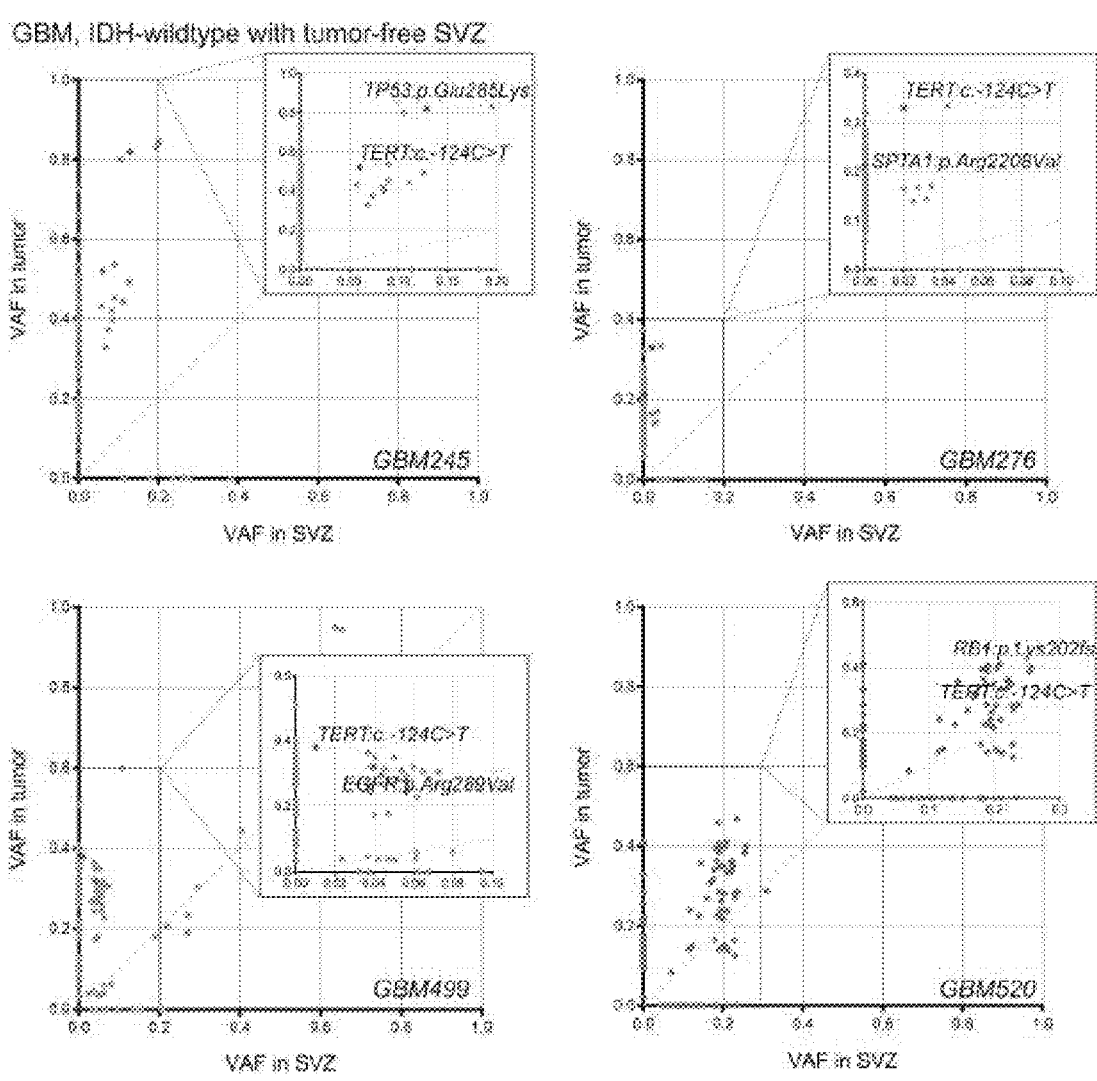

[FIG. 5]

【FIG. 6】
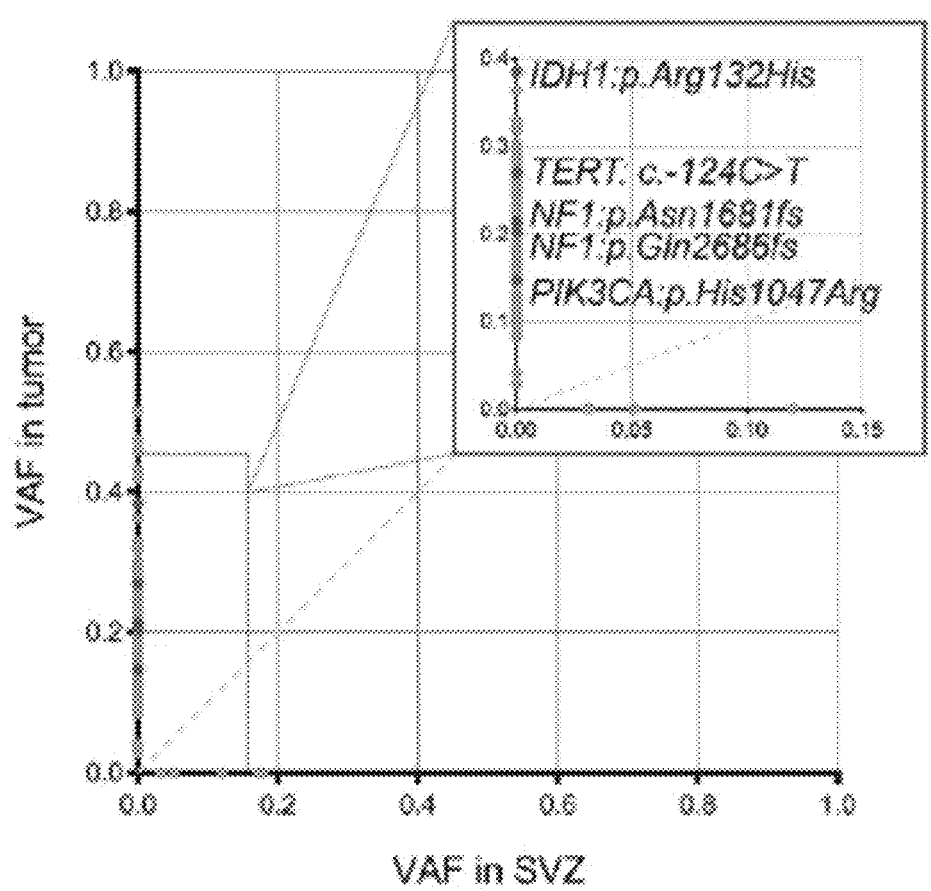

【FIG. 7】
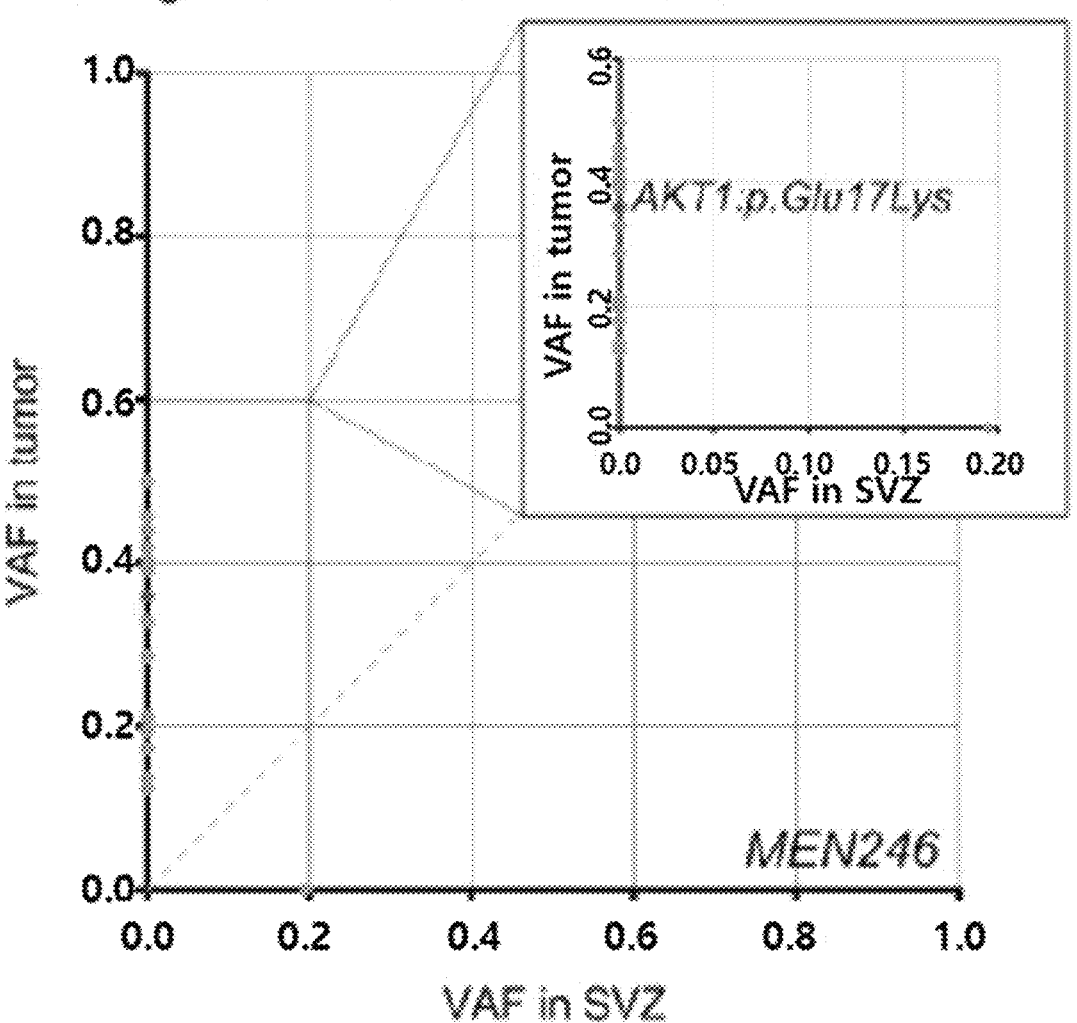

[FIG. 8]

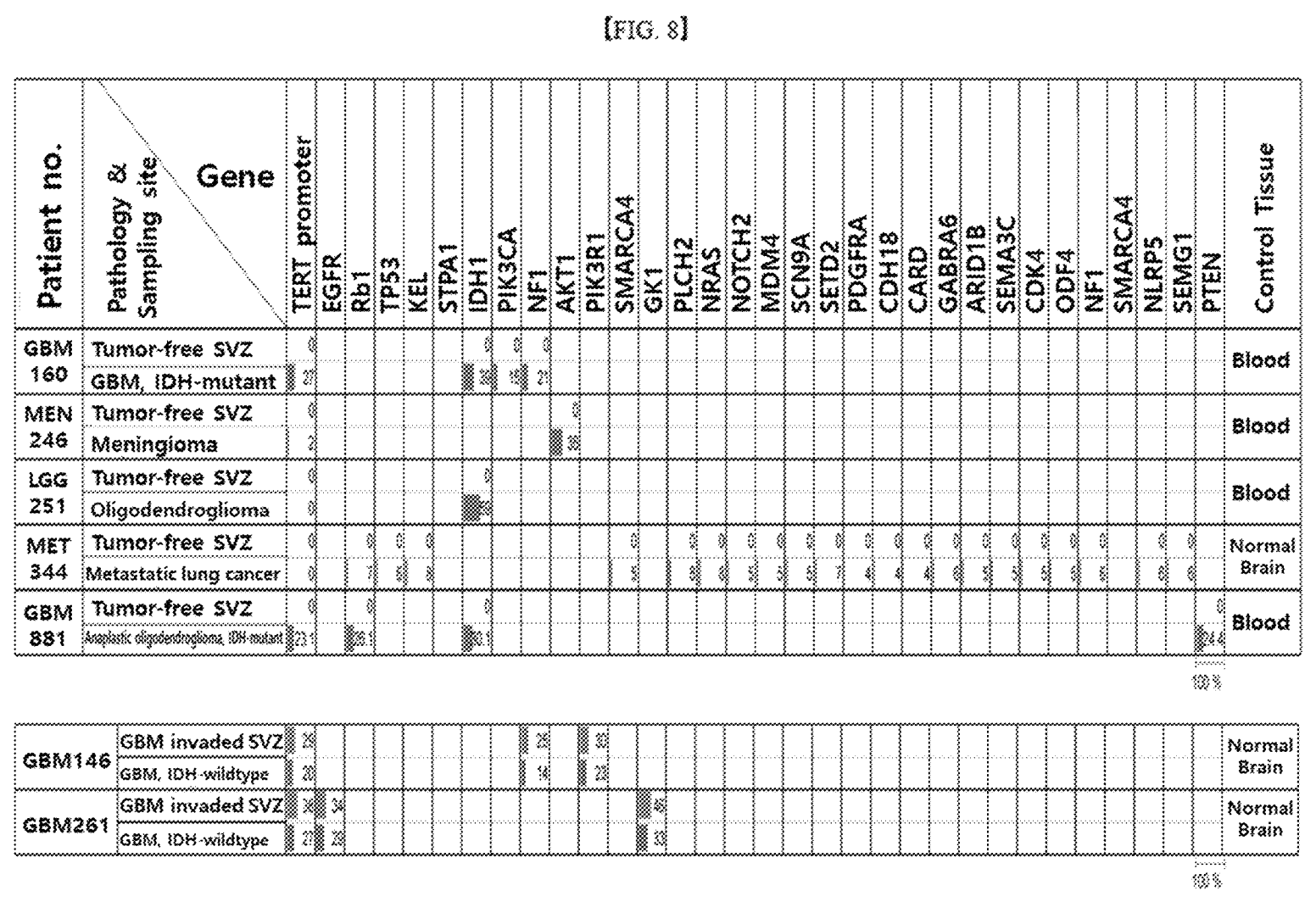

| Patient no. | Pathology & Sampling site | TERT promoter | EGFR | Rb1 | TP53 | KEL | STPA1 | IDH1 | PIK3CA | NF1 | AKT1 | PIK3R1 | SMARCA4 | GKI | PLCH2 | NRAS | NOTCH2 | MDM4 | SCN9A | SETD2 | PDGFRA | CDH18 | CARD | GABRA6 | ARID1B | SEMA3C | CDK4 | ODF4 | NF1 | SMARCA4 | NLRP5 | SEMG1 | PTEN | Control Tissue |
|---|---|---|---|---|---|---|---|---|---|---|---|---|---|---|---|---|---|---|---|---|---|---|---|---|---|---|---|---|---|---|---|---|---|---|
| GBM 160 | Tumor-free SVZ / GBM, IDH-mutant | | | | | | | | | | | | | | | | | | | | | | | | | | | | | | | | | Blood |
| MEN 246 | Tumor-free SVZ / Meningioma | | | | | | | | | | | | | | | | | | | | | | | | | | | | | | | | | Blood |
| LGG 251 | Tumor-free SVZ / Oligodendroglioma | | | | | | | | | | | | | | | | | | | | | | | | | | | | | | | | | Blood |
| MET 344 | Tumor-free SVZ / Metastatic lung cancer | | | | | | | | | | | | | | | | | | | | | | | | | | | | | | | | | Normal Brain |
| GBM 881 | Tumor-free SVZ / Anaplastic oligodendroglioma, IDH-mutant | | | | | | | | | | | | | | | | | | | | | | | | | | | | | | | | | Blood |
| GBM146 | GBM invaded SVZ / GBM, IDH-wildtype | | | | | | | | | | | | | | | | | | | | | | | | | | | | | | | | | Normal Brain |
| GBM261 | GBM invaded SVZ / GBM, IDH-wildtype | | | | | | | | | | | | | | | | | | | | | | | | | | | | | | | | | Normal Brain |

【FIG. 9】
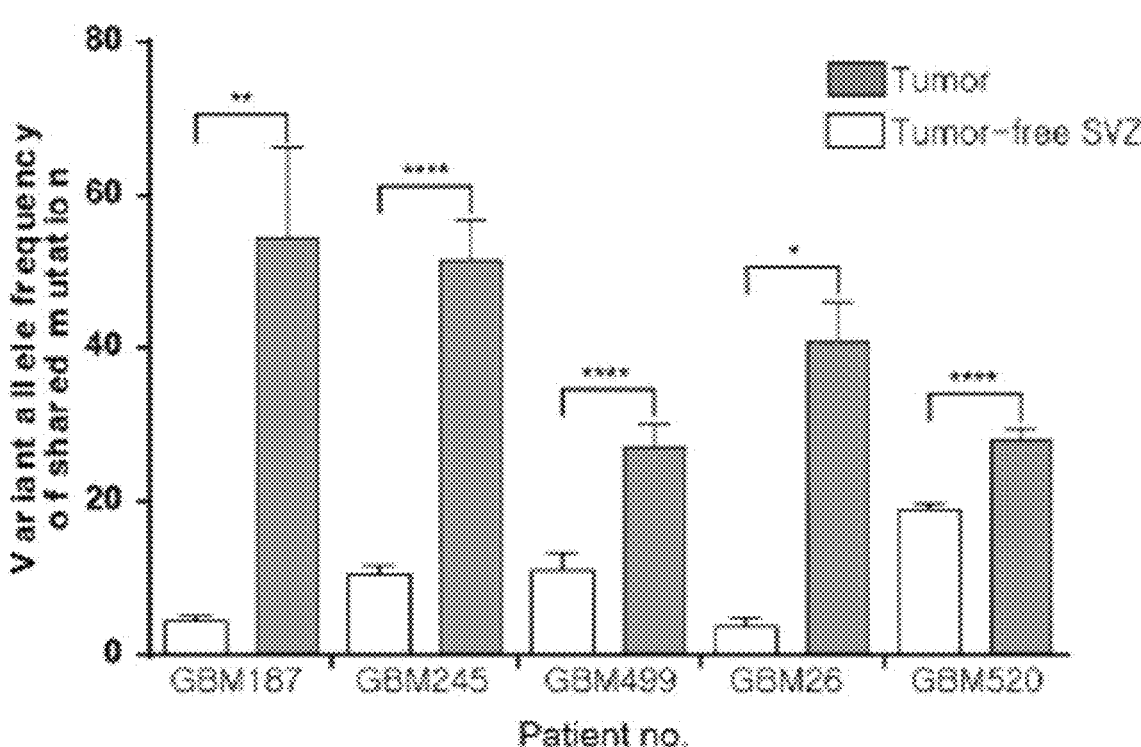

【FIG. 10】
GBM, IDH-wildtype with GBM-invaded SVZ
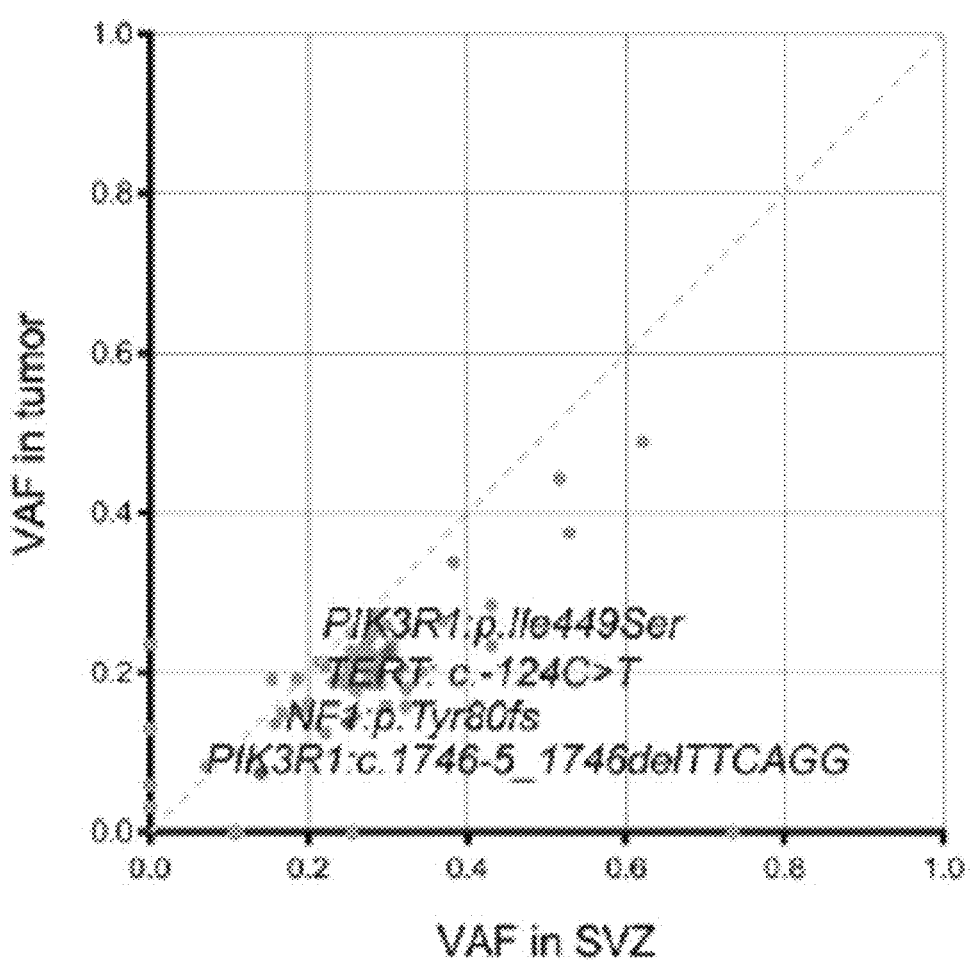

【FIG. 11】
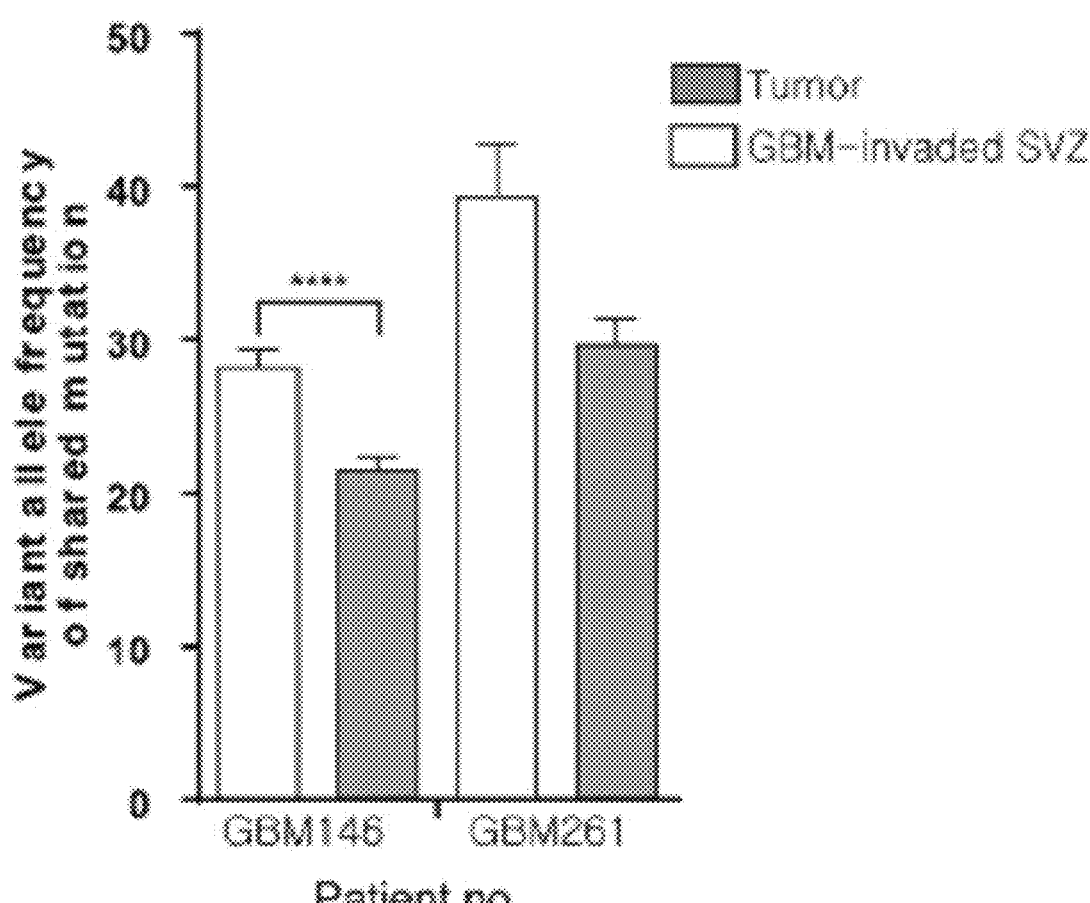

【FIG. 12】
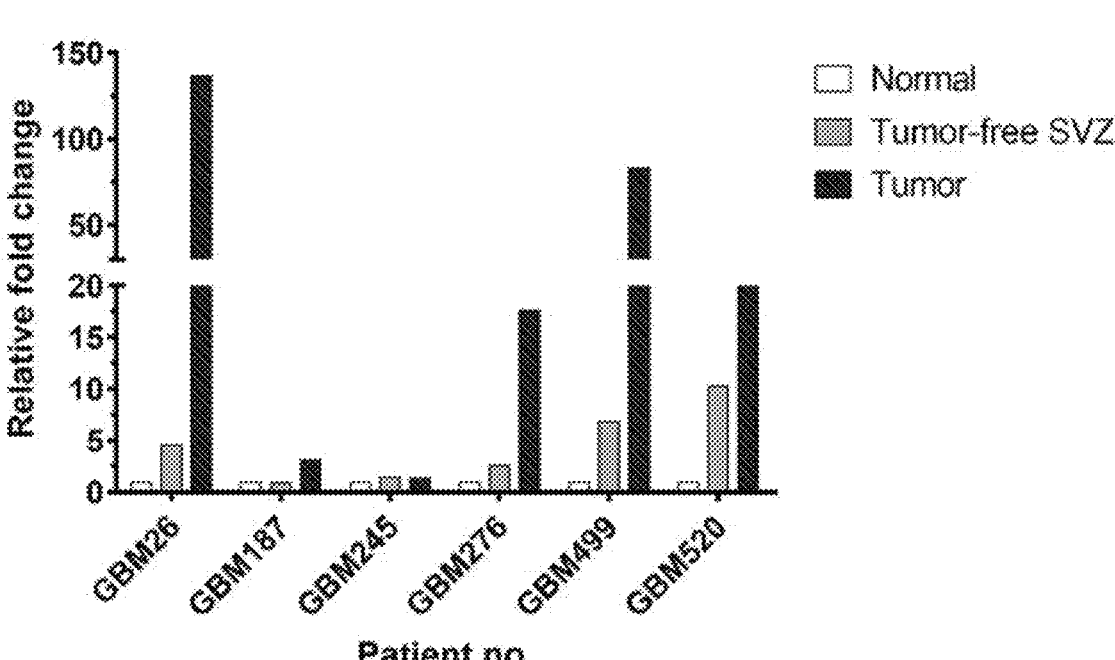

【FIG. 13】
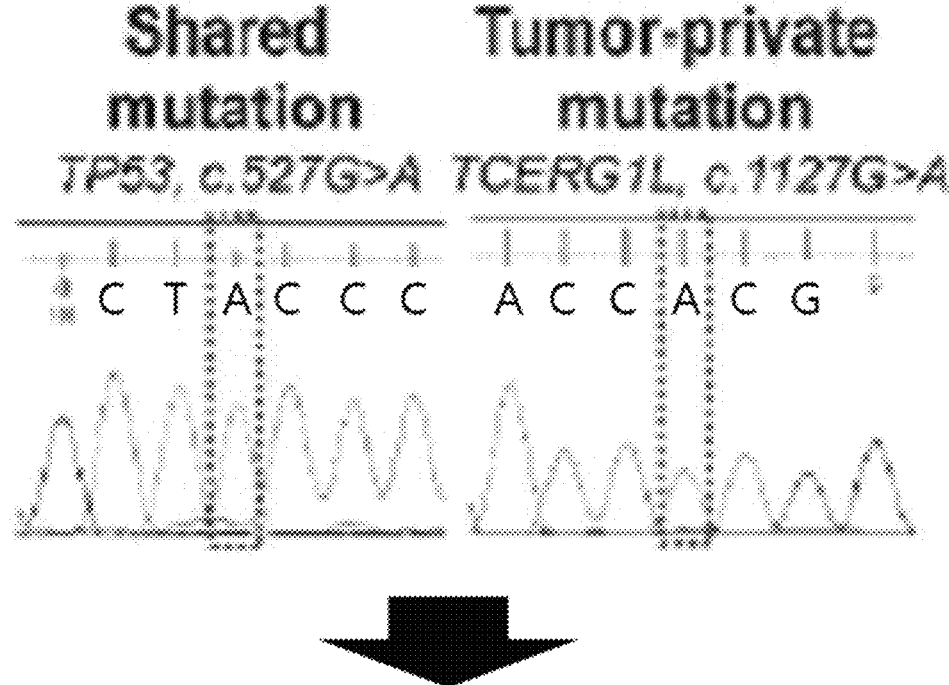
GBM185
| Shared \ Tumor-private | Tumor-private mutation | Reference sequence |
|---|---|---|
| Shared mutation | 42 | 0 |
| Reference sequence | 0 | 5 |

【FIG. 14】
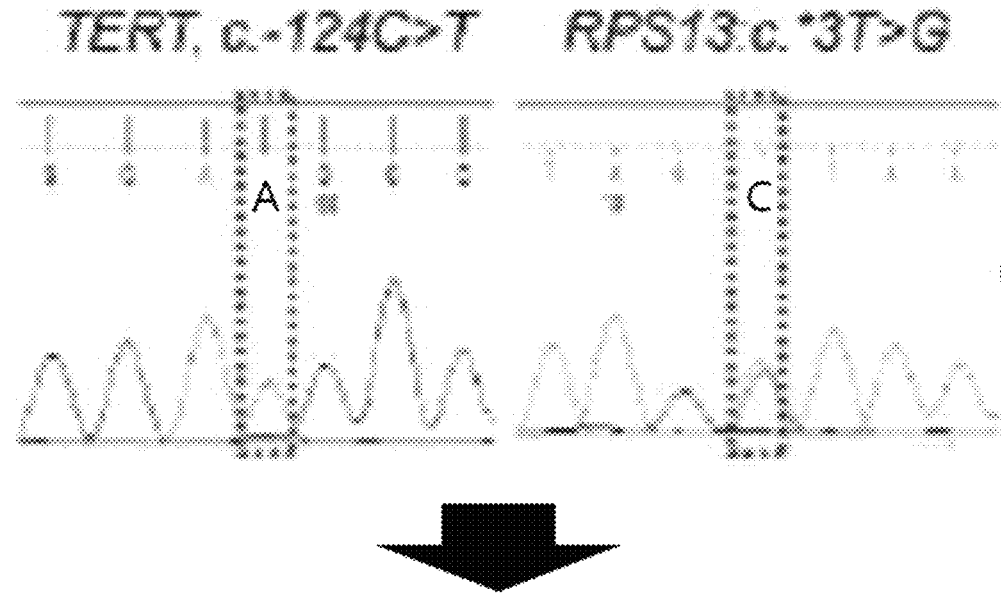
GBM520
| Shared ＼ Tumor-private | Tumor-private mutation | Reference sequence |
|---|---|---|
| Shared mutation | 12 | 0 |
| Reference sequence | 0 | 13 |

【FIG. 15】
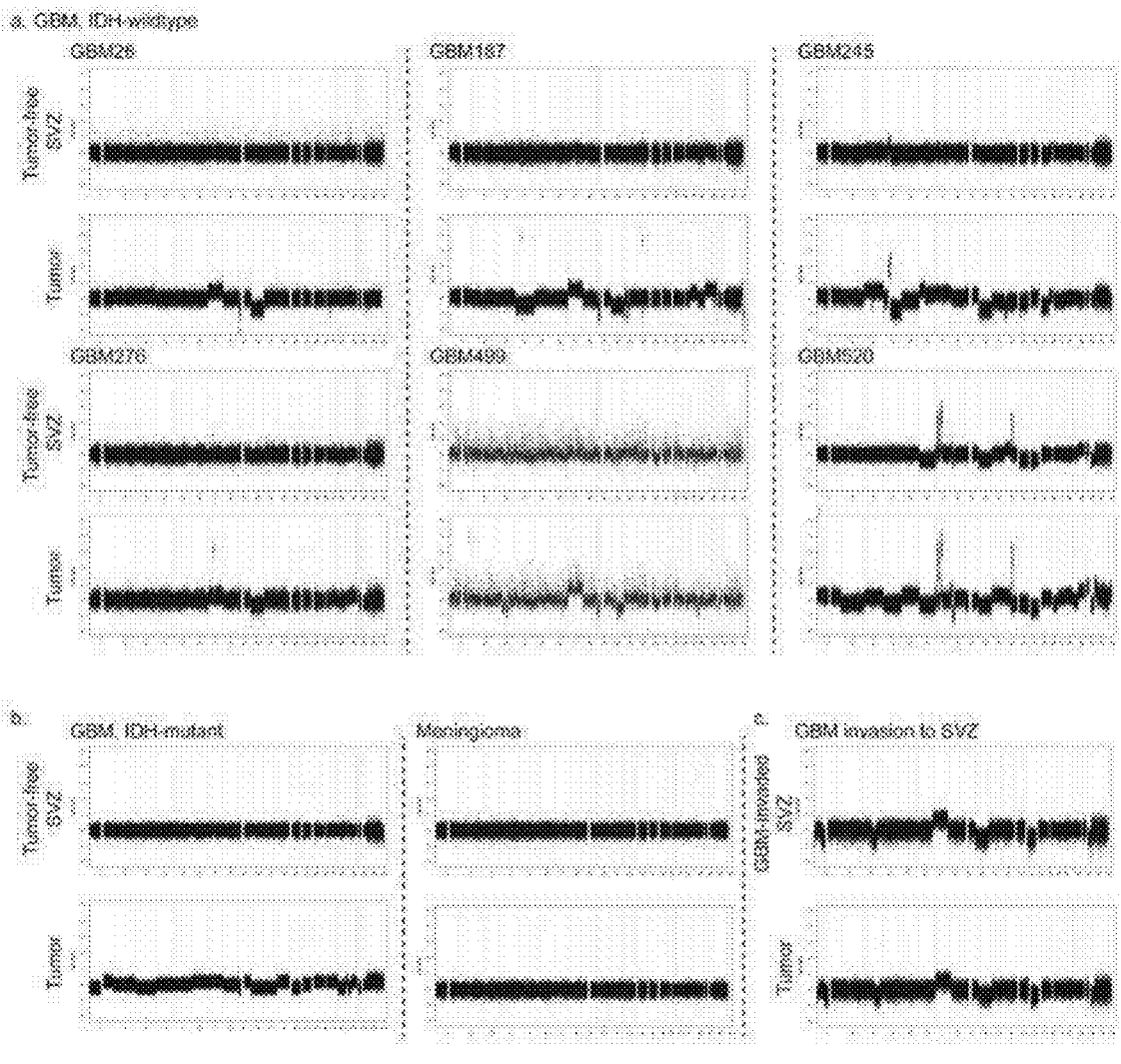

【FIG. 16】
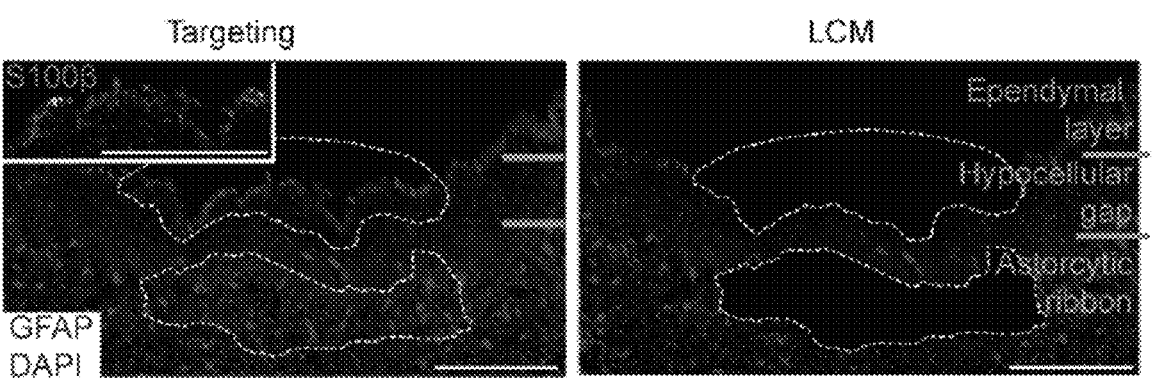
| TERT c.-124C>T | VAF (%) | |
|---|---|---|
| Patient no. | GBM499 | GBM187 |
| Bulk DNA | 1.2 | 1.6 |
| Astrocytic ribbon | 16.0 | 17.0 |
| Ependymal layer | 0 | 0 |
| Other region | 0 | 0 |

【FIG. 17】
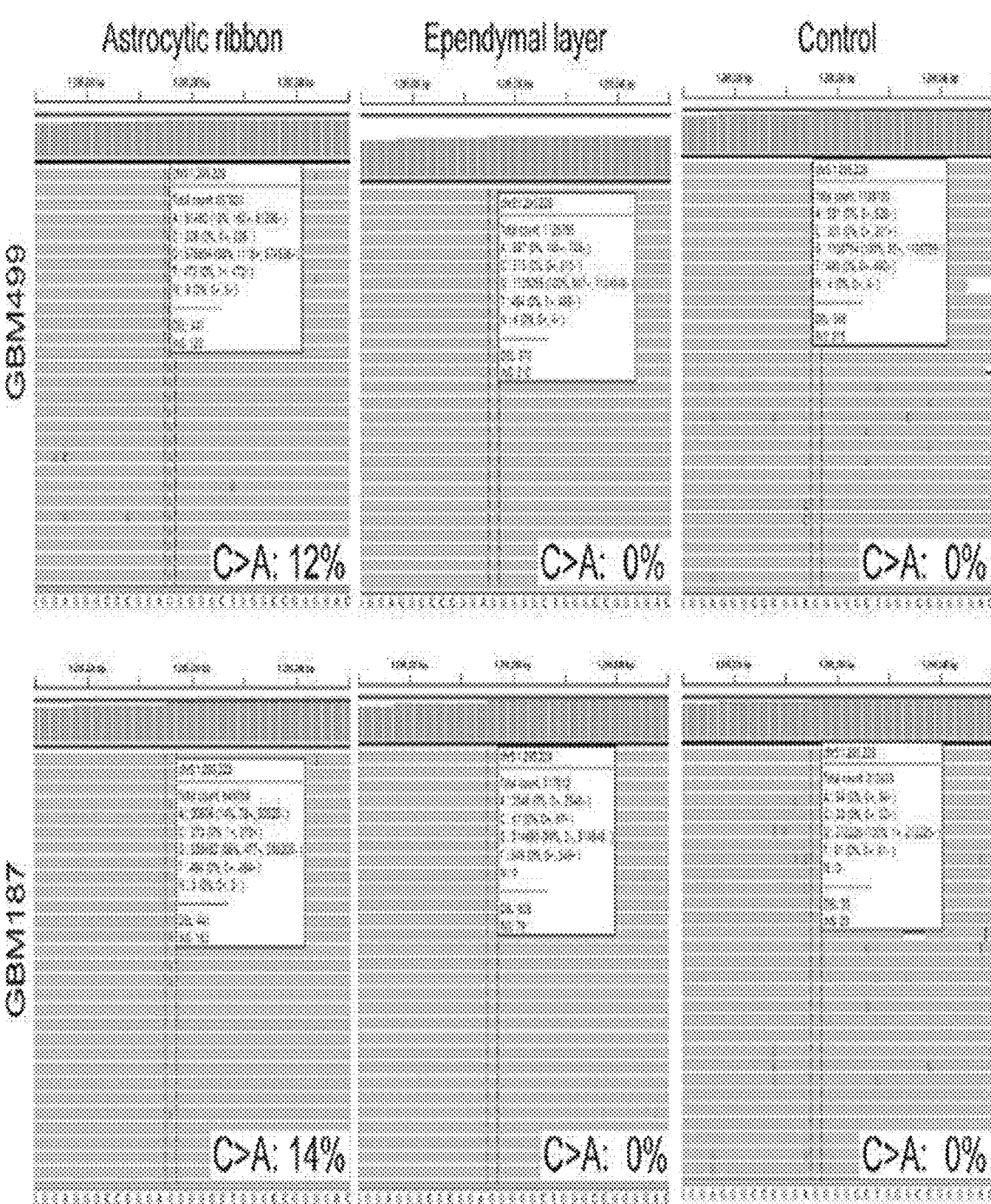

[FIG. 18]
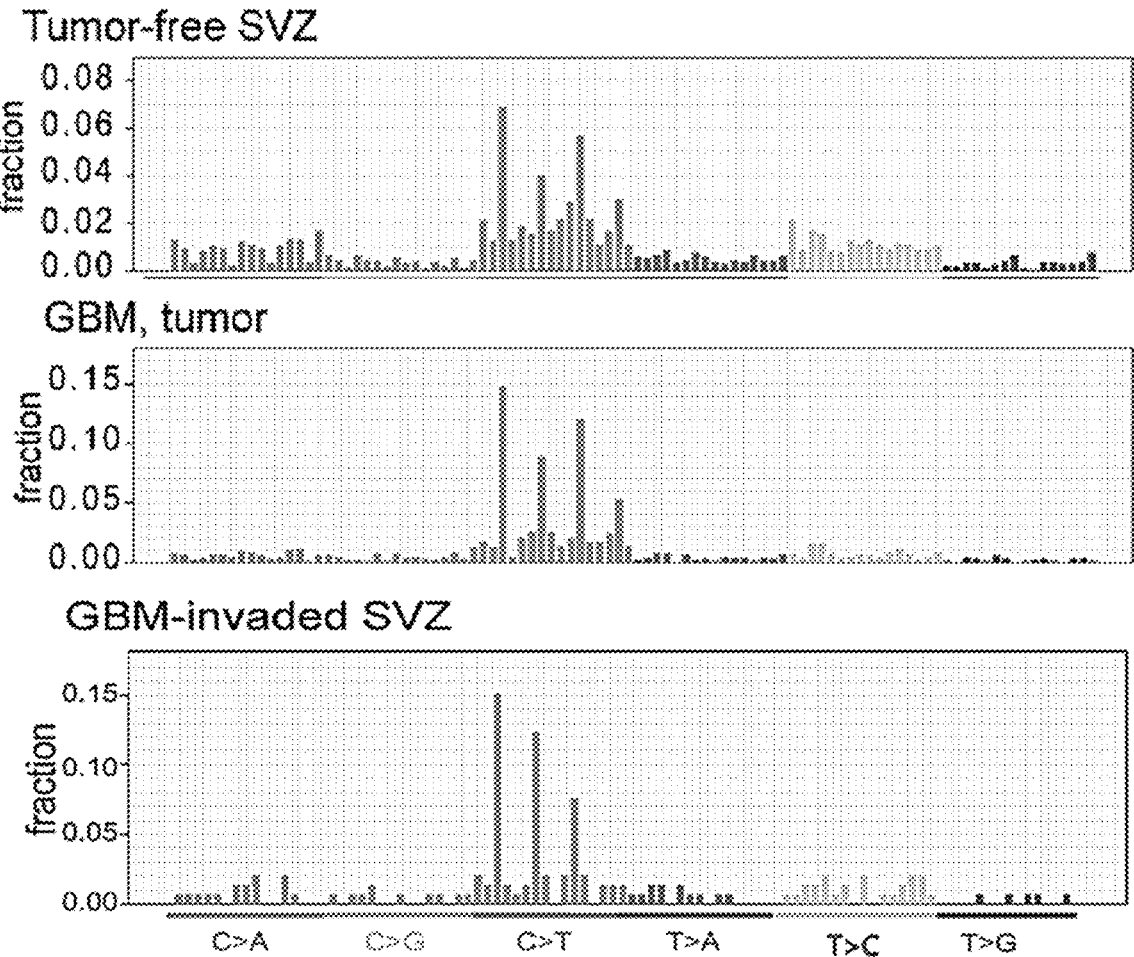

【FIG. 19】
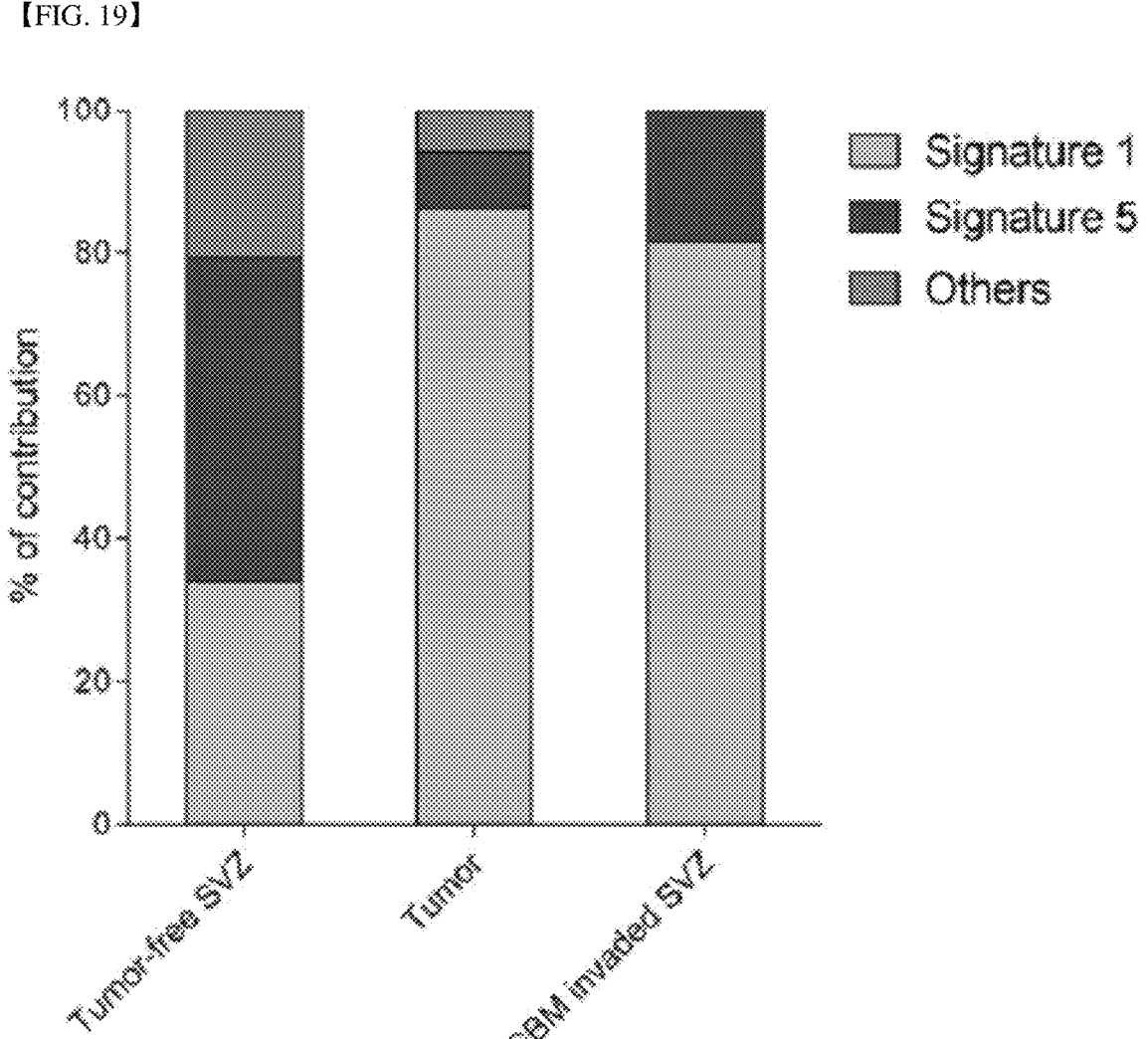

【FIG. 20】
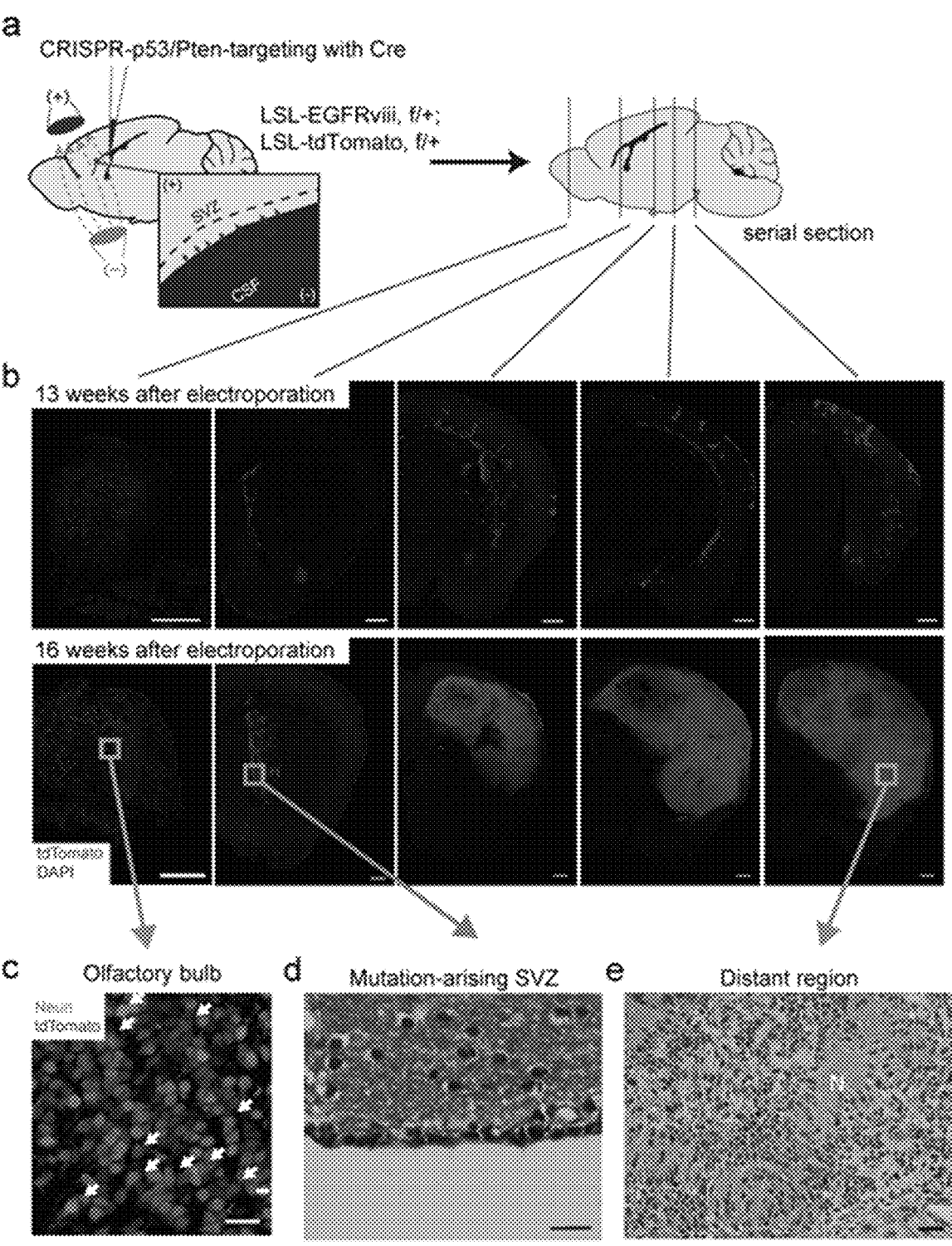

【FIG. 21】
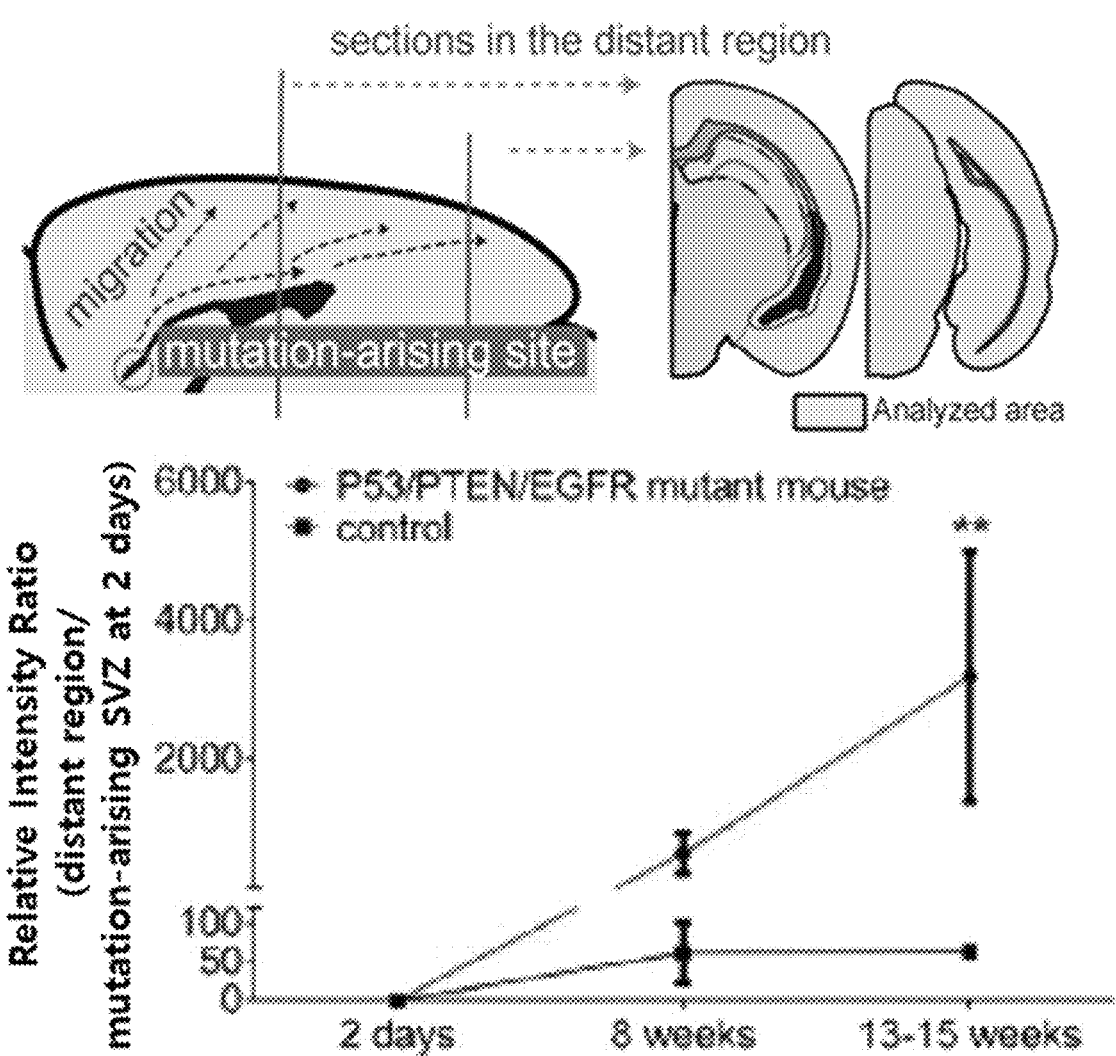

【FIG. 22】
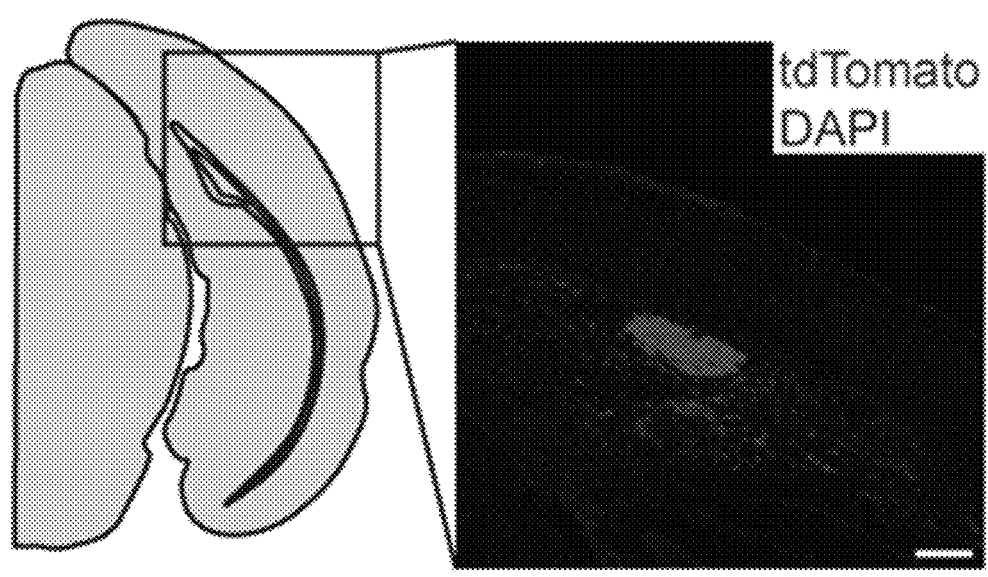
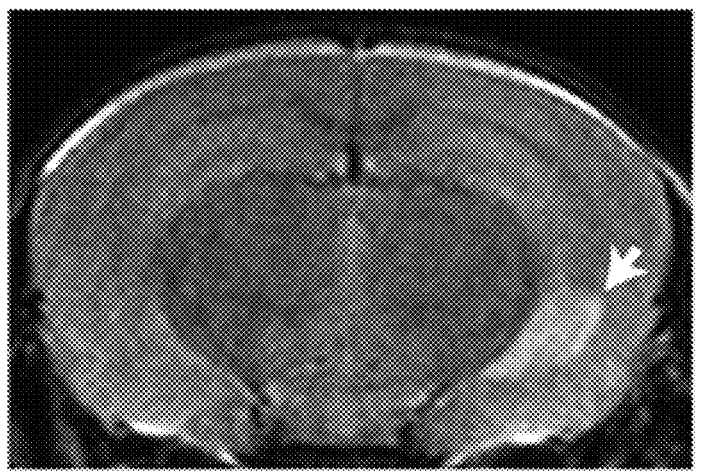
| n (%) | Rostral part | Distal part |
|---|---|---|
|  | 6 (33%) | 12 (67%) |

【FIG. 23】
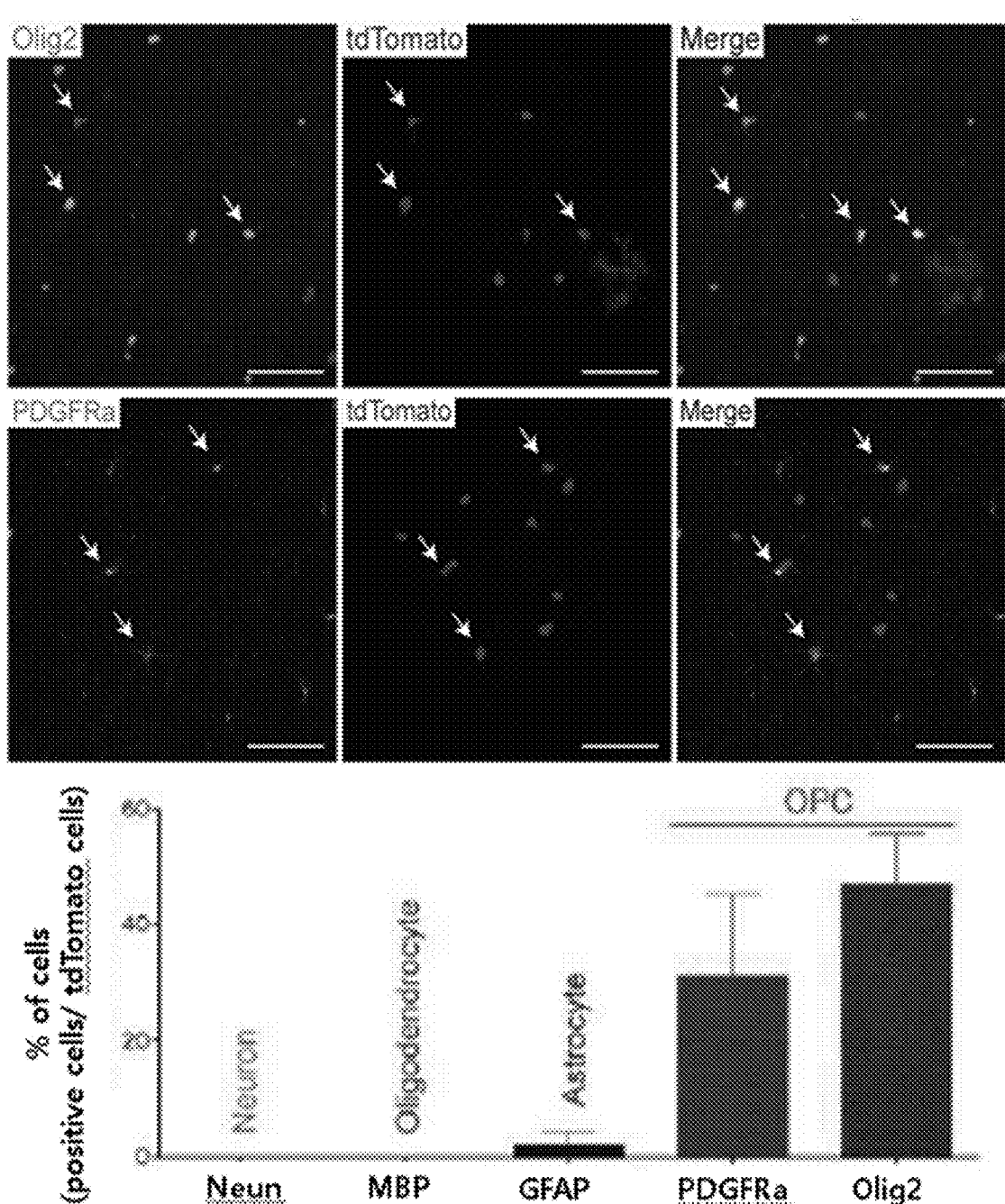

[FIG. 24]

【FIG. 25a】

【FIG. 25b】
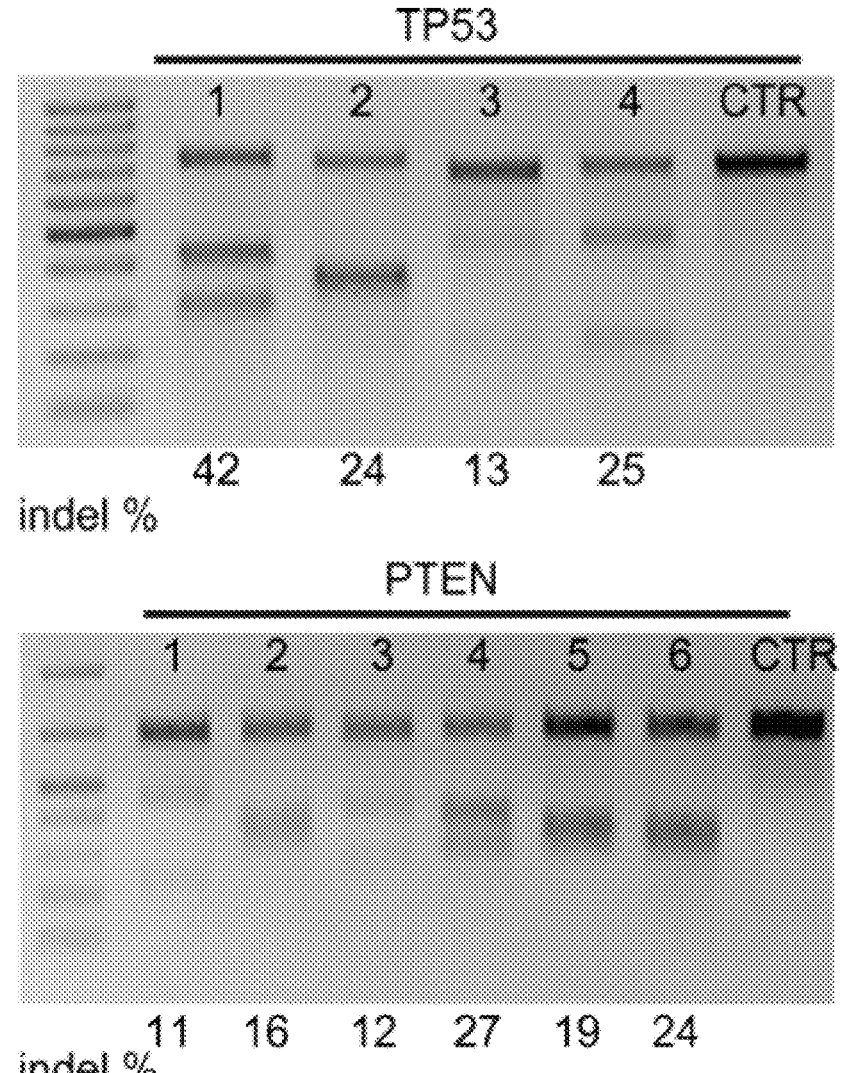

[FIG. 25c]
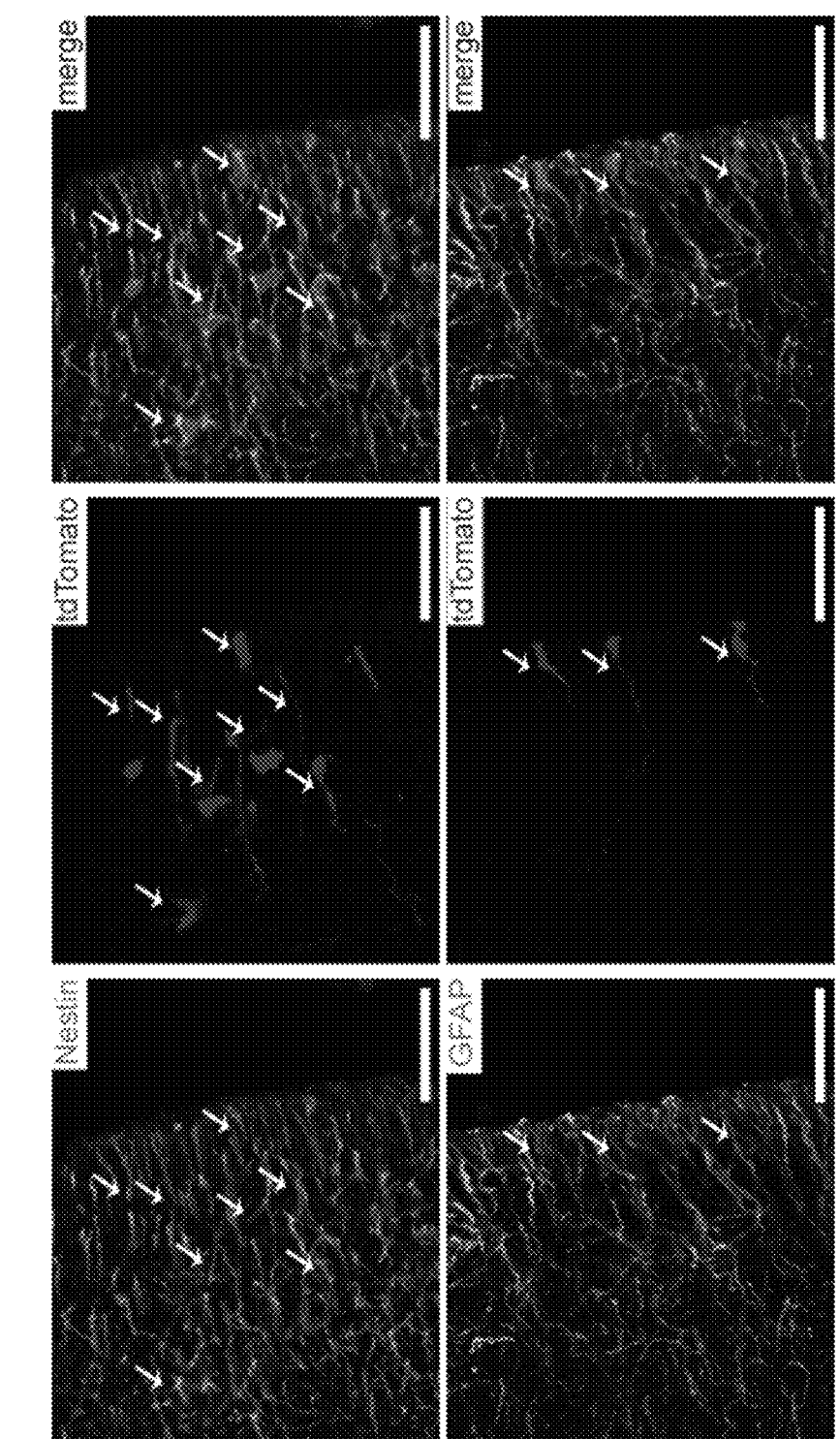

【FIG. 25d】
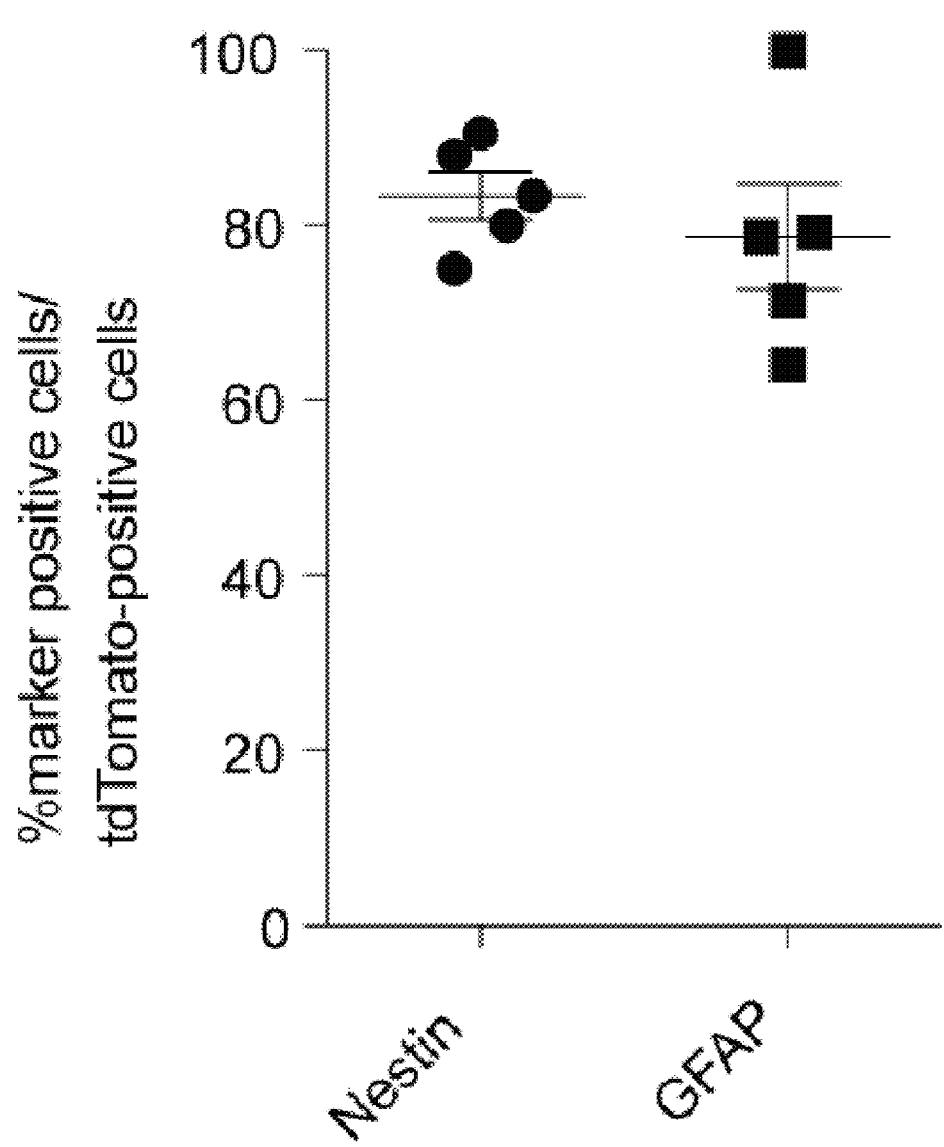

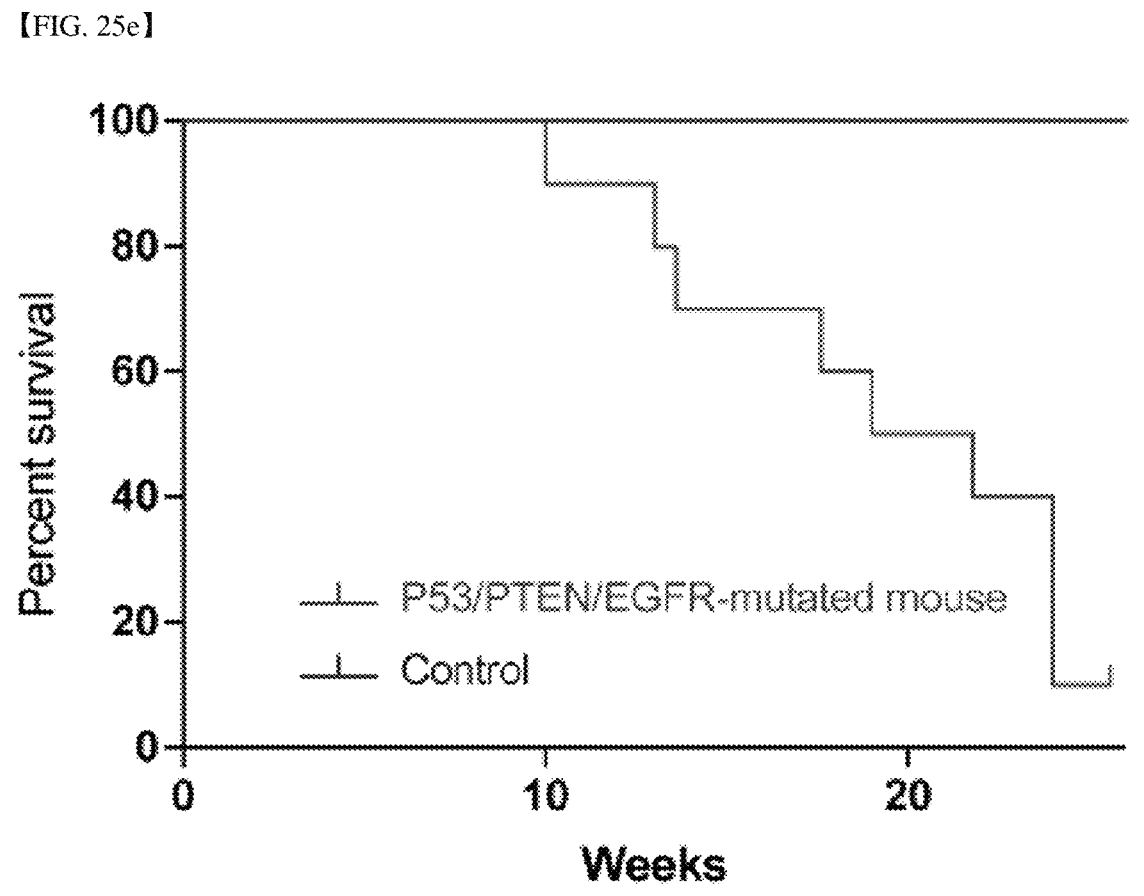

【FIG. 25e】

【FIG. 25f】
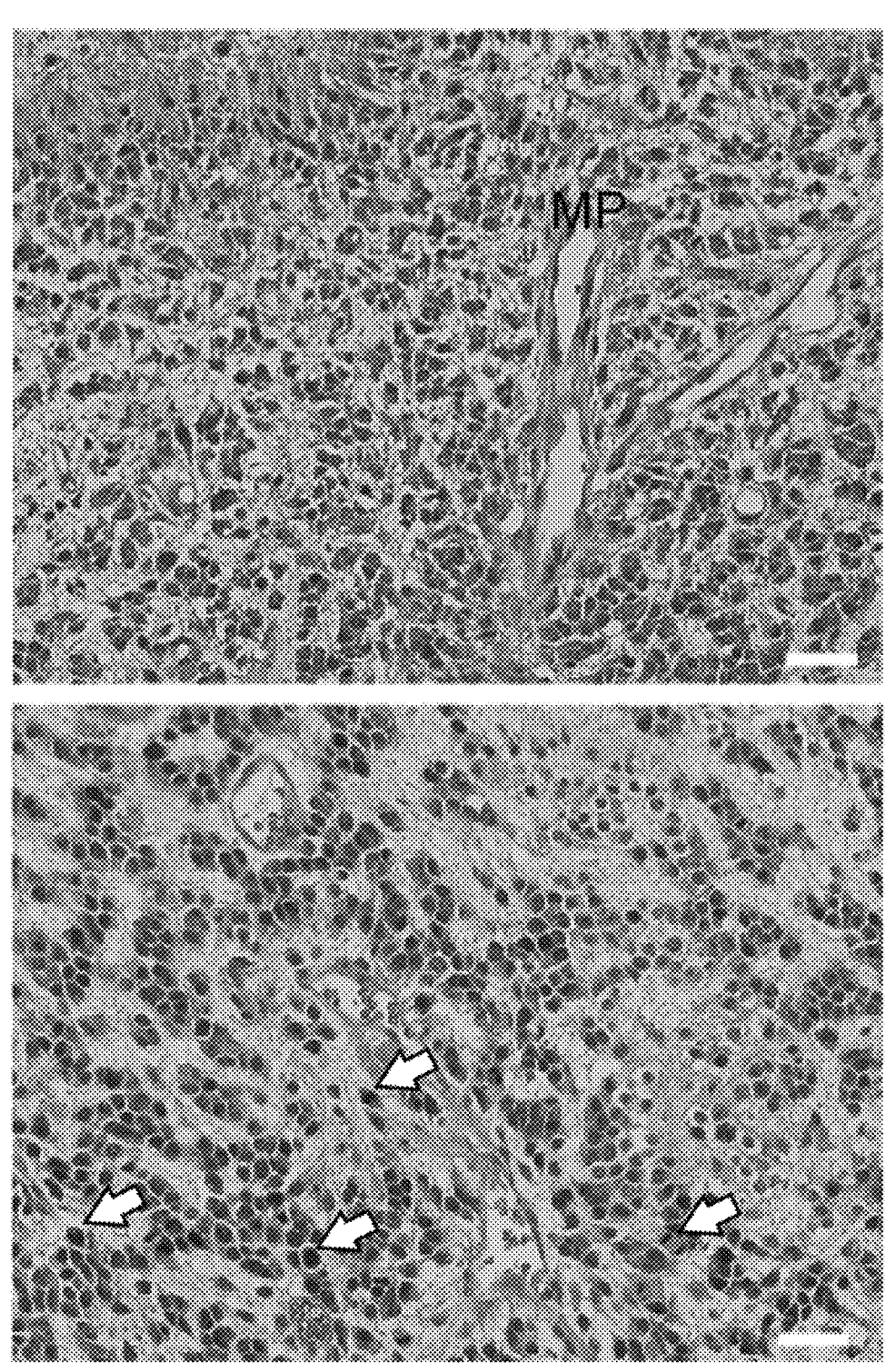

【FIG. 25g】

[FIG. 2Sh]
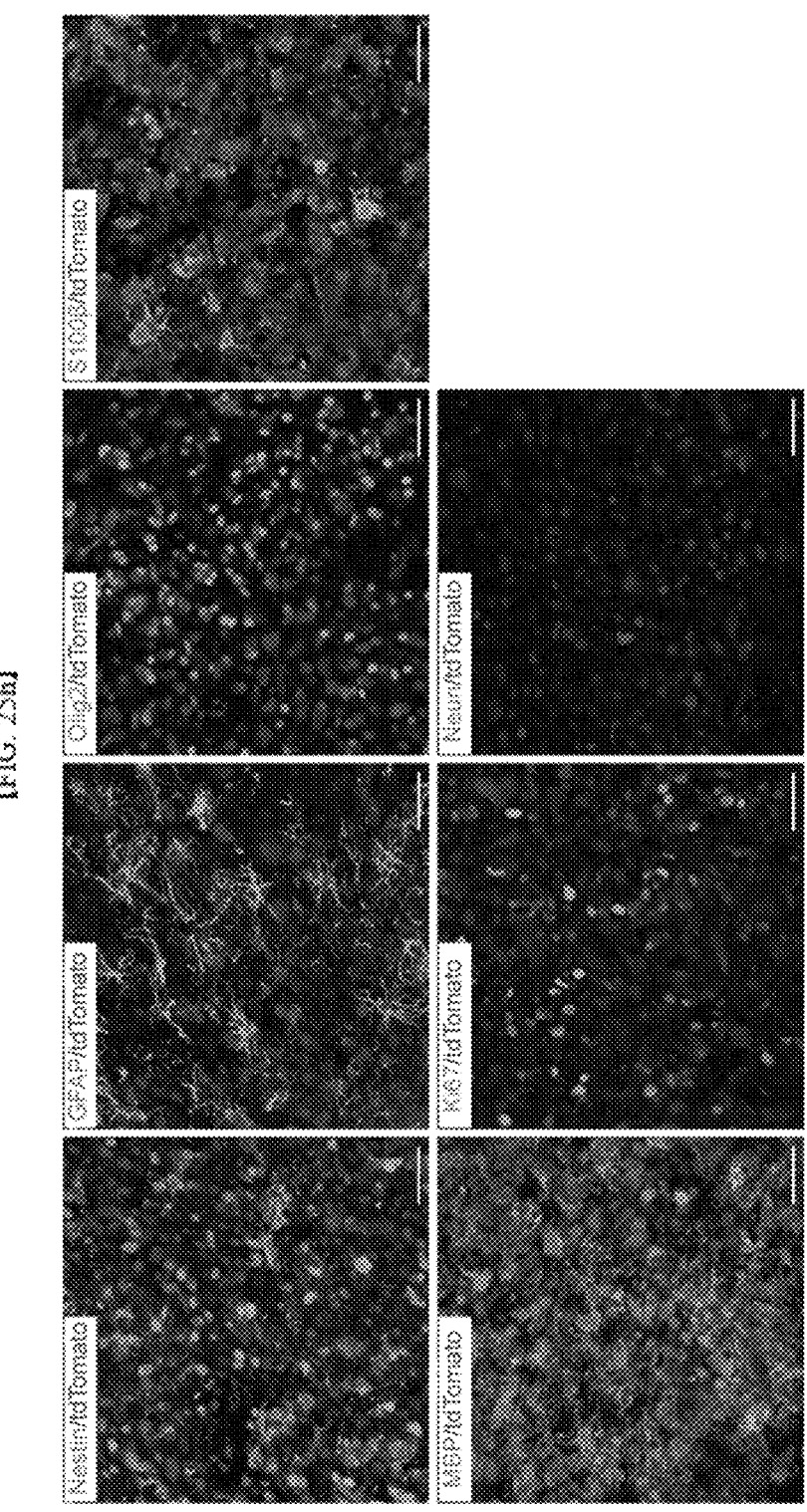

【FIG. 25i】
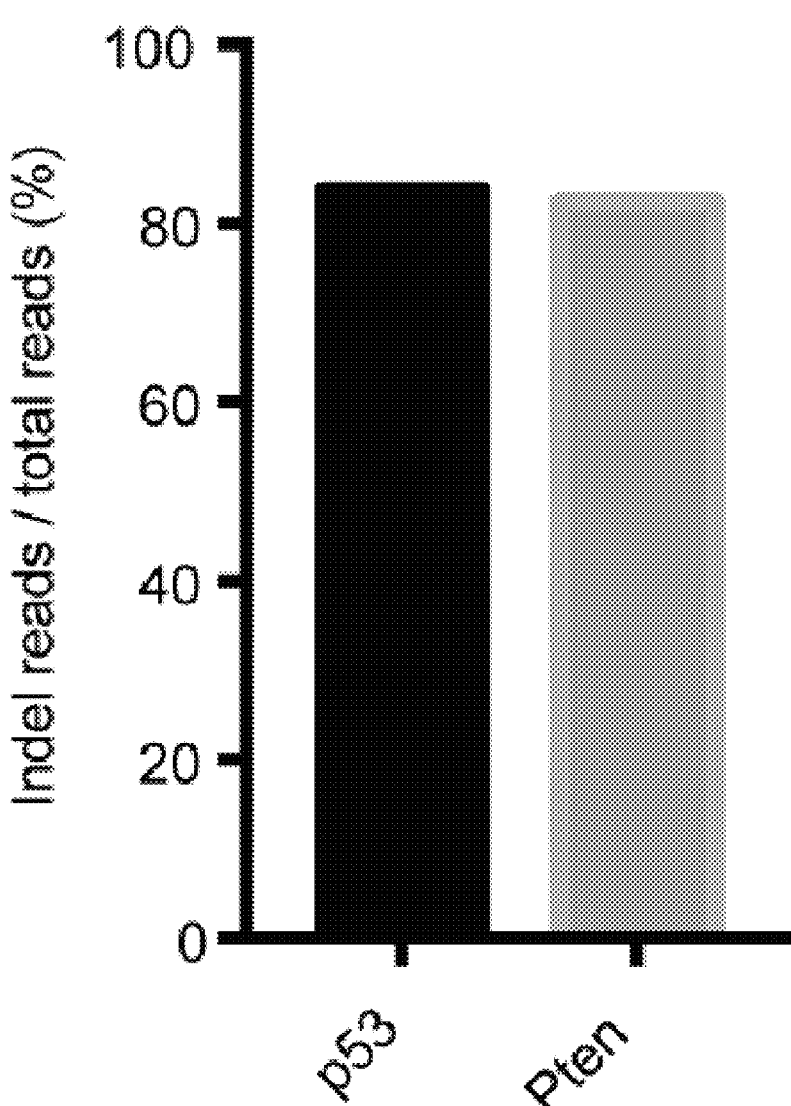

【FIG. 25j】
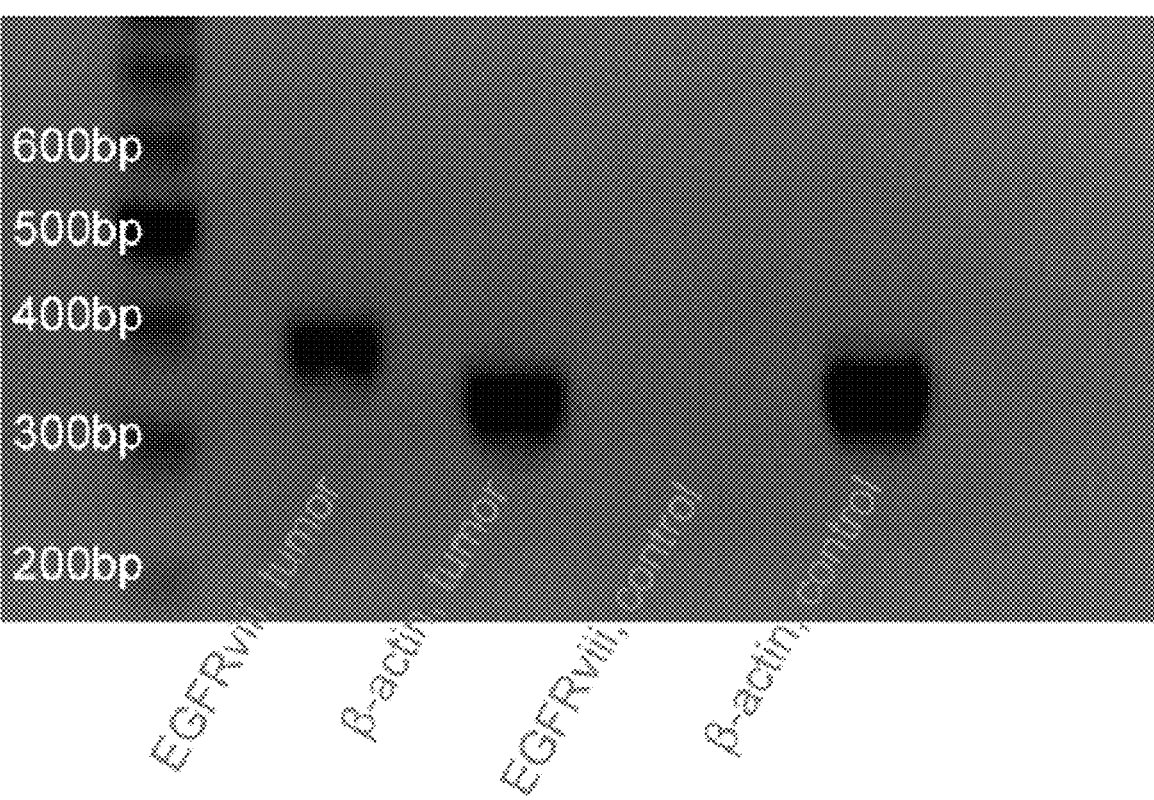

ANIMAL MODEL OF BRAIN TUMOR AND MANUFACTURING METHOD OF ANIMAL MODEL

REFERENCE TO AN ELECTRONIC SEQUENCE LISTING

The contents of the electronic sequence listing (LPP20224040US_seq_list.xml; Size: 68 K bytes; and Date of Creation: Sep. 30, 2022) is herein incorporated by reference in its entirety.

TECHNICAL FIELD

The present invention relates to a transgenic animal having glioma and a method of preparing the same.

BACKGROUND ART OF THE INVENTION

A glioma is a tumor which accounts for 60% of primary brain tumors. The glioma is a malignant tumor which is highly likely to occur and difficult to be treated, and still does not have any special treatment besides radiotherapy. A glioblastoma (GBM), classed as the most malignant type in glioma, has very high resistance to radiotherapy and chemotherapy compared to other cancers, and patients can survive only 1 year after diagnosis. Therefore, the proper diagnosis and understanding for the origin and process of each patient with GBM are important.

In addition, in case of the brain tumor, a therapeutic drug is difficult to be delivered to target region of brain due to the brain blood barrier, and the neurobiology of the brain is a relative lack of understanding, thereby preventing the active development of a therapeutic agent. Furthermore, glioblastomas present an aggressive variant when compared to other brain tumors, which can result in catastrophic results within weeks if not treated within a short time.

Accordingly, radiotherapy and chemotherapy are performed to treat glioblastoma along with surgical treatment. However, there is no perfect treatment due to resistant variants, and re-occurrence caused by tumor stem cells. Therefore, it is necessary to develop an early diagnosis and understanding of origins and new therapeutic methods based on them.

In order to develop such a therapeutic method, it is urgent to develop an animal model that can reflect the phenomenon in a human patient. Studies of these animal models are expected to pinpoint the mechanisms of brain tumors and play an important role in verifying the effectiveness of various new therapeutic targets and new therapies.

DISCLOSURE

Technical Problem

An object of the present invention is a method for predicting a tissue origin of brain tumors by comparing the expression level of oncogene mutation in the subventricular zone (SVZ) and the expression level of oncogene mutation in brain tumor tissue.

Another purpose of the present invention is related to a method to providing information to decide target site to treat brain tumor effectively by estimating tissue origin of brain tumor.

It is another object of the present invention to provide information for determining a target site capable of effectively treating a brain tumor by predicting the tissue origin of a brain tumor.

It is another object of the present invention to provide a transgenic animal having glioma, more specifically, a brain tumor model animal having p53, Pten, and EGFR mutations specifically for neural stem cells in the subventricular zone, and a method for producing the same.

A further object of the present invention is a use of a brain tumor animal model for screening a therapeutic agent by testing the efficacy of a candidate agent using a brain tumor model animal.

Technical Solution

The present invention is related to a method to predict tissue origin of a brain tumor of unknown primary site by identifying mutations of oncogenes. More particularly, the present invention is related to a method to predict tissue origin of brain tumor comprising a step that measuring allele frequency of mutations at least one of the TERT C228T and TERT C250T in subventricular zone tissue and brain tumor tissue of target individuals following a step that determining the tissue origin of brain tumor is originated from SVZ when the mutations are shared by SVZ tissue and brain tumor tissue, and when the allele frequency of mutations in the SVZ are lower than the levels in brain tumor tissue.

The present invention is related to a brain tumor animal model that directly reflects the phenomenon in human patients and a preparation method the same, more specifically, a brain tumor animal model that mutations are introduced into p53, Pten, and EGFR genes, and a screening method of a therapeutic agent for brain tumor using the animal model, and a preparing method thereof.

The present invention allows to establish an appropriate therapeutic strategy by determining treating target site that maximize treating effect for the brain tumor according to the predicted tissue origin by comparing the expression level of mutant oncogenes between the subventricular zone and the brain tumor tissue.

Glioblastoma (GBM) is a type of incurable brain tumors and patients diagnosed with GBM can live only 15 months on average. It is able to step further in understanding of GBM disease and developing novel methods for treatment by identifying the origin cell having mutation causing GBM. Accumulation of somatic mutations can cause gliomagenesis, and neural stem cells (NSCs) which have capacities of self-renewal and proliferation in the adult human SVZ can be the cells which GBM originates from. However, there has been no explanation based on direct genetic evidences so far about that.

Accordingly, the present inventors reached the present invention by discovering that the astrocyte-like NSCs in the SVZ are the origin cells of human IDH-wildtype GBM by using human brain tissues and genome-edited mouse models.

In one embodiment of the present invention is related to a method to predict tissue origin of brain tumor comprising following steps:

(a) Measuring the allele frequency of at least one of the telomerase reverse transcriptase (TERT) 1,295,228 C>T (TERT C228T) and TERT 1,295,250 C>T (TERT C250T) mutant genes in the SVZ tissue of target individuals;

(b) Measuring the allele frequency of at least one of the TERT C228T and TERT C250T mutant genes in the brain tumor tissue of target individuals; and (c) Predicting the brain tumor is originated from the SVZ when the SVZ and brain tumor tissues are sharing the mutant genes at least one of TERT C228T and TERT C250T, and at least one of the TERT C228T and TERT C250T mutant genes according to the present invention are showing lower allele frequency in SVZ tissue than in brain tumor tissue.

In another embodiment of the present invention is related to a method of providing information to determine a target site for treating the brain tumor comprising following steps:

(a) Measuring the allele frequency of at least one of telomerase reverse transcriptase (TERT) 1,295,228 C>T(TERT C228T) and TERT 1,295,250 C>T(TERT C250T) mutant genes in the SVZ tissue of target individuals;

(b) Measuring the allele frequency of at least one of the TERT C228T and TERT C250T mutant genes in the brain tumor tissue of target individuals;

(c) Predicting the brain tumor is originated from the SVZ when the SVZ and the brain tumor tissues are sharing at least one of TERT C228T and TERT C250T mutant genes, and at least one of the TERT C228T and TERT C250T mutant genes according to the present invention are showing lower allele frequency in SVZ tissue than in brain tumor tissue; and (d) Determining the SVZ as the treating target site.

The term "treating target site" as used herein refers to a region or cells that anti-cancer treatments such as radiotherapy, chemotherapy, or immunotherapy are intensively applied to treat brain tumor effectively.

In the present invention, the expression levels of at least one mutant gene selected from the group consisting of EGFR (Epidermal growth factor receptor) mutant, TPS3 (Tumor protein p53) mutant, PTEN (Phosphatase and tensin homolog) mutant, and Rb1 (Retinoblastoma 1) mutant can be measured additionally not only TERT C228T and TERT C250T.

In the present invention, measuring the expression levels of the EGFR mutants, TP53 mutants, PTEN mutant, and Rb1 mutant can be a process to identify whether the mutants are exist and their expression levels, preferably, variant allele frequency (VAF) or copy number variation (CNV) can be measured. In the present invention, VAF of at least one mutant selected from the group consisting of EGFR mutant, TPS3 mutant, PTEN mutant, and Rb1 mutant can be measured and the CNV of the EGFR mutants can be measured.

The term "target individual" as used herein can refer to, but not limited to, a patient having or suspecting to brain tumor who need or be expected an appropriate treatment for brain tumor.

In the present invention, the "brain tumor", the object of the origin prediction, can be glioma, more preferably, glioblastoma, most preferably, isocitrate dehydrogenase (IDH)-wild-type (WT) primary glioblastoma.

In the present invention, the term "glioblastoma (GBM)" as used herein refers to a primary tumor arose from brain spinal cord tissue or its surrounding membrane area, and it is the tumor originated from a neuroglia cell which is abundantly present in normal brain tissue. In the present invention, the majority of the glioblastoma (>90%) are primary tumors arising without precursor disease before, on the other hand, the secondary glioblastoma are rare diseases and can be arisen and progress from low-grade astrocytoma. Most of secondary glioblastoma have IDH mutants, but the IDH mutants hardly ever exist in primary glioblastoma.

In the present invention, the term "subventricular zone (SVZ)" refers to a region situated throughout the lateral walls of lateral ventricles where nearly contact with ventricular layer. SVZ has characteristics that not only the proliferating cells are gathered in but also it is consisting of variety cells in diverse maturity stages.

In the present invention, the SVZ tissue and brain tumor tissue separated from the target individual can be, but not limited to, positioned at a distance of 1 to 40 mm, 3 to 35 mm, or 5 to 30 mm from one another.

In addition, the SVZ separated from the target individual in the present invention, can be separated from arbitrary regions of SVZ, preferably from astrocytic ribbon of SVZ, and more preferably comprising the astrocyte-like NSCs in the astrocyte ribbon, to improve accuracy of estimating tissue origin.

In the present invention, after the SVZ and brain tumor tissues were prepared, the allele frequency can be measured for at least one of TERT C228T and TERT C250T mutations, preferably TERT C228T as the tumor-inducing TERT promoter mutant in each tissue.

In the present invention, the "TERT 1,295,228 C>T (C228T)" and "TERT 1,295,250 C>T(C250T)" refer to the mutations occurred on the promoter region of TERT (telomerase reverse transcriptase) gene in melanoma-prone family, especially C228T and C250T which are observed somatic cell mutation of TERT gene promoter frequently (Science 339(6122): 959-9).

Specifically, the TERT C228T in the present invention, is the mutation that a nucleotide C located 124 bp upstream of the ATG start site of TERT is mutated to T, and can be also represented by 'c.-124C>T'. Additionally, the TERT C250T is the mutation that a nucleotide C located 146 bp upstream of the ATG start site of TERT is mutated to T, and can be also represented by 'c.-146>T'.

In the present invention, measuring allele frequency of the TERT C228T and/or TERT C250T mutants can be a process to identify the existence and expression levels of the mutations, preferably a variant allele frequency (VAF) can be measured.

In the present invention, the term "variant allele frequency (VAF)" as used herein refers to variants in the target site of tissue, for example, allele frequency of mutations. The term "allele frequency" as used herein refers to a relative frequency of the allele in a target site, and it can be represented by %.

In the present invention, VAF of the TERT C228T and/or TERT C250T mutants can be carried out by DNA-sequencing analysis. More specifically, target site of 200 to 350 bp are amplified by PCR using primers specific to the mutants, followed by measuring relative frequency (%) of the allele of TERT C228T and/or TERT C250T mutants. The PCR can be carried out, for example, but not limited to, by using a forward primer represented by SEQ. ID. No. 1 and a reverse primer represented by SEQ. ID. NO. 2.

Preferably, in the present invention, it can be predicted whether the disease arise or not through whether the product produced by PCR amplification using sense and antisense primers of micro RNA polynucleotide. The PCR conditions, length of sense and antisense primers can be modified on the basis of those known in the art.

In the present invention, after measuring the variant allele frequency for at least one of TERT C228T and TERT C250T mutants in SVZ and brain tumor tissues respectively, if the result shows the SVZ and brain tumor tissues share same mutant at least one of TERT C228T and TERT C250T, and the variant allele frequencies of the at least one of mutants are lower in SVZ than brain tumor tissue, it can be predicted the brain tumor is originated from the SVZ, preferably from the astrocytic ribbon of SVZ, and more preferably from the astrocyte-like NSCs in the astrocyte ribbon.

For example, in the present invention, the variant allele frequencies of at least one of TERT C228T and TERT C250T of the SVZ (VAF1) can be, but not limited to, 0 to 50%, 0 to 40%, 0 to 30%, 0 to 25%, 0 to 20%, 0 to 15%, or 0 to 10%.

In the present invention, the variant allele frequencies of at least one of TERT C228T and TERT C250T of the brain tumor tissue (VAF2) can be, but not limited to, 10 to 100%, 20 to 100%, 20 to 95%, 25 to 95%, or 25 to 90%.

In the present invention, the brain tumor tissue can be predicted that the origin is SVZ, preferably astrocytic ribbon of SVZ, and more preferably the astrocyte-like NSCs in the astrocyte ribbon, when the VAF2 which is measured variant allele frequencies of at least one of the TERT C228T or TERT C250T mutants from brain tumor, is 1 to 45 times, or In the present invention, the term "copy number variation (CNV)" as used herein refers to a type of structural variants in a genome that is amplification or deletion of DNA fragments over 1 Kb.

In the present invention, the EGFR tyrosine kinase activity in glioblastoma cells may be dysregulated by EGFR gene mutations (such as amplifications, indels, SNVs), overexpression of EGFR protein, increased gene copy number, rearrangements of chromosomes, and activation by autocrine function. Most of the GBMs characterized by EGFR amplification are positive for the mutant EGFRvIII, EGFRvV, and EGFR SNVs. For example, the alterations or mutations of EGFR, TP53, PTEN and Rb1 could be, but not limited to, represented as Table 1 below as well as Table 1 of Cimino et al. Exp Mol Pathol. 2015 June; 98(3): 568-573 (see also Table 1 of Lee et al. (2006) PLoS Med 3(12)).

TABLE 1

| Gene | Reference No. | Mutation of amino acid | Mutation of nucleotides(CDS) | Chromo-some | Start site | Termination site |
|---|---|---|---|---|---|---|
| EGFR | NM_005228.4 | Ala289Val (Substitution - Missense, position 289, A –> V) (SEQ ID NO: 11) | C866T (Substitution, position 866, C –> T) (SEQ ID NO: 12) | Chr7 | 55154129 (on Assembly GRCh38) 55221822 (on Assembly GRCh37) | 55154129 (on Assembly GRCh38) 55221822 (on Assembly GRCh37) |
| TP53 | NM_000546.5 | Cys176Tyr (Substitution - Missense, position 176, C –> Y) (SEQ ID NO: 13) | G527A (Substitution, position 527, G –> A) (SEQ ID NO: 14) | Chr17 | 7675085 (on Assembly GRCh38) 7578403 (on Assembly GRCh37) | 7675085 (on Assembly GRCh38) 7578403 (on Assembly GRCh37) |
| TP53 | NM_000546 | Glu285Lys (Substitution - Missense, position 285, E –> K) (SEQ ID NO: 15) | G853A (Substitution, position 853, G –> A) (SEQ ID NO: 16) | Chr17 | 7673767 (on Assembly GRCh38) 7577085 (on Assembly GRCh37) | 7673767 (on Assembly GRCh38) 7577085 (on Assembly GRCh37) |
| PTEN | COSM4943 | Val317fs*6 (SEQ ID NO: 17) | 950_954del (SEQ ID NO: 18) | Chr10 | 89720798 | 89720798 |
| PTEN | COSM4899 | Val317fs*3 (SEQ ID NO: 19) | 951_954del (SEQ ID NO: 20) | Chr10 | 89720799 | 89720799 |
| Rb1 | — | Lys202fs (SEQ ID NO: 21) | 606_607AG > A (SEQ ID NO: 22) | Chr13 | 48923158 | 48923159 |

1.5 to 45 times (VAF2/VAF1 ratio is 1 to 50, 1 to 45, or 1.5 to 45) of VAF which is measured variant allele frequencies of at least one of the TERT C228T and TERT C250T mutants from SVZ.

Additionally, in the present invention, besides the TERT C228T and TERT C250T, the expression levels of at least one of mutants selected from the group consisting of EGFR (Epidermal growth factor receptor) mutants, TP53 (Tumor protein p53) mutants, PTEN (Phosphatase and tensin homolog) mutants, and Rb1 (retinoblastoma 1) mutants, can be measured additionally.

In the present invention, the term "p53" as used herein is one of tumor suppressor factors known to inhibit abnormal proliferation of cells and induce the death of cancer cells. The "p53" is represented as TP53 or expressed Trp53 in case of mouse gene.

In the present invention, measuring expression levels of mutations of EGFR, TP53, PTEN and Rb1 could be a process to identify whether the mutants are exist and expression levels, preferably VAF or CNV can be measured. In the present invention, the VAF of at least one of mutations of EGFR, TP53, PTEN and Rb1, and the CNV of the EGFR mutations can be measured.

In one embodiment of the present invention, gene variants common in normal SVZ cells and tumor tissue at a sufficient distance were identified in a human IDH-wildtype GBM patient. The variants are shown in Table 1 above. The common mutations were identified in EGFR, TP53, PTEN and Rb1, particularly PTEN and Rb1 showed frameshift (fs).

Specifically, in the present invention, the VAF or CNV of EGFR mutants TP53 mutants, PTEN mutants and Rb1 mutants can be performed by DNA-sequencing analyze. More specifically, it can be performed by measuring relative frequency of variant alleles (%) of the mutations of EGFR, TP53, PTEN or Rb1 after PCR amplification of target site of 200 to 350 bp using the mutants-specific primers. The primer sets could be, but not limited to, SEQ. ID. No. 3 as a forward primer, and SEQ. ID. No. 4 as a reverse primer for amplifying the EGFR mutant gene-specific primers, SEQ. ID. No. 5 as a forward primer, and SEQ. ID. No. 6 as a reverse primer for the PTEN mutant gene-specific primers, SEQ. ID. No. 7 as a forward primer, and SEQ. ID. No. 8 as a reverse primer for the TP53 mutant gene-specific primers, and SEQ. ID. No. 9 as a forward primer, and SEQ. ID. No. 10 as a reverse primer for the Rb1 mutant gene-specific primers.

In the present invention, after measuring the VAFs or CNVs of at least one of mutants of EGFR, TP53, PTEN and Rb1 in the SVZ and brain tumor tissues respectively, if the result shows the SVZ and brain tumor tissues share same mutant at least one of mutants of EGFR, TP53, PTEN and Rb1 in the SVZ, and the variant allele frequencies of the at least one of mutants are lower in SVZ than brain tumor tissue, it can be predicted the brain tumor is originated from the SVZ, preferably from the astrocytic ribbon of SVZ, and more preferably from the astrocyte-like NSCs in the astrocyte ribbon.

In the present invention, the variant allele frequencies at least one selected from the group consisting of mutations of EGFR, TP53, PTEN and Rb1 (VAF3) in the SVZ can be, but not limited to, 0 to 40%, 0 to 30%, 0 to 25%, 0 to 100%, 0 to 15%, or 25 to 95%.

In the present invention, the variant allele frequencies at least one selected from the group consisting of mutations of EGFR, TP53, PTEN and Rb1 (VAF4) in the brain tumor tissue can be, but not limited to, 10 to 100%, 20 to 30%, 0 to 25%, 0 to 20%, 0 to 15%, or 0 to 10%.

In the present invention, the brain tumor tissue can be predicted that the origin is SVZ, preferably astrocytic ribbon of SVZ, and more preferably the astrocyte-like NSCs in the astrocyte ribbon, when the VAF4 which is measured variant allele frequencies of at least one selected from the group consisting of mutations of EGFR, TP53, PTEN and Rb1 in brain tumor, are 1 to 50 times, 1 to 40 times, 1.5 to 40 times, 1.5 to 30 times, 1.5 to 25 times, 2 to 25 times, or 2 to 20 times (VAF4/VAF3 ratio is 1 to 50, 1 to 40, 1.5 to 40, 1.5 to 30, 1.5 to 25, 2 to 25 or 2 to 20) of VAF3 which is measured variant allele frequencies of at least one selected from the group consisting of mutations of EGFR, TP53, PTEN and Rb1 in SVZ.

In the present invention, the CNV1 of at least one mutant selected from the group consisting of mutations of EGFR, TP53, PTEN, and Rb1 in the SVZ can be, but not limited to, 0 to 30, 0 to 25, 0 to 20, 0 to 15 or 0 to 10.

In the present invention, the CNV1 of at least one mutant selected from the group consisting of mutations of EGFR, TP53, PTEN, and Rb1 in the brain tumor tissue can be, but not limited to, 10 to 200, 0 to 25, 10 to 180, 10 to 170, 10 to 160, or 10 to 150.

In the present invention, the brain tumor tissue can be predicted that the origin is SVZ, preferably astrocytic ribbon of SVZ, and more preferably the astrocyte-like NSCs in the astrocyte ribbon, when the CNV2 which is measured copy number variants of at least one selected from the group consisting of mutations of EGFR, TP53, PTEN and Rb1 in brain tumor, are 1 to 50 times, 1 to 40 times, 1.5 to 40 times, 1.5 to 30 times, or 2 to 30 times (CNV2/CNV1 ratio is 1 to 50, 1 to 40, 1.5 to 40, 1.5 to 30, or 2 to 30) of CNV1 which is measured variant allele frequencies of at least one selected from the group consisting of mutations of EGFR, TP53, PTEN and Rb1 in SVZ.

In another embodiment of the present invention is related to a pharmaceutical agent preventing recurrence of brain tumor comprising antibodies specific to proteins expressed by at least one mutations selected from the group consisting of TERT C228T, TERT C250T, EGFR Ala289Val, TP53 Cys176Tyr, TP53 E285K, PTEN Val317fs*6, PTEN Val317fs*3 and Rb1 Lys202fs.

In the present invention, if the brain tumor originated from SVZ, the possibility of recurrence of the brain tumor is very high. Accordingly, the present invention can prevent recurrence of the brain tumor effectively by treating, for example, antibodies specific to proteins expressed by at least one mutations selected from the group consisting of TERT C228T, TERT C250T, EGFR Ala289Val, TP53 Cys176Tyr, TP53 E285K, PTEN Val317fs*6, PTEN Val317fs*3 and Rb1 Lys202fs to the SVZ, preferably astrocytic ribbon of the SVZ, and more preferably the astrocyte-like NSCs in the astrocyte ribbon.

The therapeutic agents of the present invention preferably comprising at least one of antibodies specific to proteins expressed by TERT C228T and TERT C250T. Antibodies specific to proteins expressed by at least one mutations selected from the group consisting of EGFR Ala289Val, TP53 Cys176Tyr, TP53 E285K, PTEN Val317fs*6, PTEN Val317fs*3 and Rb1 Lys202fs can be included additionally.

In the present invention the antibody as used herein refers to antibodies showing specific binding with the proteins expressed by the mutations of the present invention. The antibodies can be prepared by conventional methods from proteins obtained by conventional cloning method that each marker genes are inserted to the expression vector. Partial peptides that can be produced by the proteins are also included, and the partial peptides of the present inventions comprise at least 7 amino acids, preferably at least 9 amino acids, more preferably at least 12 amino acids. The forms of antibodies of the present invention are not particularly limited, and includes polyclonal antibody, monoclonal antibody, or part of those while they have antigen binding activities. Furthermore, the antibodies of the present invention can include special antibodies such as humanized antibodies. The antibodies used to detect cancer diagnosis marker of the present invention include functional fragment of an antibody molecule as well as a complete form having full-length of heavy chain and full-length of 2 light chains. The functional fragment of an antibody refers to a fragment having at least antigen binding activity, such as Fab, F(ab'), F(ab')2 and Fv.

The antibodies of the present invention, a person skilled in the art can design the protein-specific antibody based on the amino acid sequence of the protein expressed from the mutant genes of the present invention. A monoclonal antibodies to the proteins can be used the one produced by conventional monoclonal antibody producing method in the art, or commercially available one. Additionally, polyclonal antibodies recognizing the proteins, instead of monoclonal antibodies can be used and produced by antiserum preparation method which is conventional in the art.

In the present invention, the term "prevention" as used herein refers to, but not limited to, actions inhibiting recurrence of symptoms of brain tumors using the therapeutic agents of the present invention, or every action as long as inhibiting or delaying recurrence of symptoms of brain tumors.

The therapeutic agents of the present invention can be administrated together with other anticancer drugs that allow enhancing the effect of recurrence inhibition and inhibition of brain tumor.

The anticancer drugs can be, but not limited to, at least one selected from the group consisting of nitrogen mustard, imatinib, oxaliplatin, rituximab, erlotinib, neratinib, lapatinib, gefitinib, vandetanib, nilotinib, semaxanib, bosutinib, axitinib, cediranib, lestaurtinib, trastuzumab, gefitinib, bortezomib, sunitinib, carboplatin, sorafenib, bevacizumab, cisplatin, cetuximab, Viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate-chitosan, gemcitabine, doxifluridine, pemetrexed, tegafur, capecitabine, gimeracil, oteracil, azacitidine, methotrexate, uracil, cytarabine, fluorouracil, fludarabine, enocitabine, flutamide, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, peplomycin, temozolomide, busulfan, ifosfamide, cyclophosphamide, melphalan, altretamine, dacarbazine, thiotepa, nimustine, chlorambucil, mitolactol, leucovorin, tretinoin, exemestane, aminogluthetimide, anagrelide, navelbine, fadrozole, tamoxifen, toremifene, testolactone, anastrozole, letrozole, vorozole, bicalutamide, lomustine and carmustine.

In the present invention, the pharmaceutical agents can be formulated in a capsule, a tablet, a granule, an injection, an ointment, a powder, or a drink, and the pharmaceutical agents can be applied to humans.

The pharmaceutical agents of the present invention can be, but not limited to, formulated in the form of oral dosage forms such as powders, granules, capsules, tablets, aqueous suspensions, external preparations, suppositories, and sterilized injection solutions according to conventional methods. The pharmaceutical agents of the present invention can include a pharmaceutically acceptable carrier. For oral administration, the pharmaceutically acceptable carrier can include one or more of binders, lubricants, disintegrants, excipients, solubilizing agents, dispersing agents, stabilizers, suspending agents, pigments, fragrances, and the like. For injection, the pharmaceutically acceptable carrier can include one or more of buffers, preservatives, pain-relieving agents, solubilizing agents, isotonic agents, stabilizers, and the like. For local administration, the pharmaceutically acceptable carrier can include one or more of bases, excipients, lubricants, preservatives, and the like. The pharmaceutical composition according to the present invention can be mixed with the pharmaceutically acceptable carriers as described above to provide various formulations. For example, for oral administration, the pharmaceutical composition of the present invention can be prepared in the form of tablet, troche, capsule, elixir, suspension, syrup, wafer or the like, and for injection, the pharmaceutical composition can be prepared in the form of unit dosage ampoules or multiple dosage containers. In addition, the pharmaceutical composition of the present invention may be prepared as solutions, suspensions, tablets, capsules, sustained-release formulations, or the like.

Meanwhile, examples of carriers, excipients and diluents, which are suitable for formulation, include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil, or the like. In addition, the pharmaceutical composition of the present invention can further contain one or more of fillers, anticoagulants, lubricants, wetting agents, fragrances, emulsifiers, preservatives, and the like.

Routes for administration of the pharmaceutical composition according to the present invention include, but are not limited to, oral, intravenous, intramuscular, intra-arterial, intra-marrow, intrathecal, intracardiac, transdermal, subcutaneous, intraperitoneal, intranasal, intestinal intrarectal, local, sublingual and intrarectal routes. Oral or parenteral administration is preferred.

In the present invention, the term "parenteral" as used herein includes subcutaneous, intradermal, intravenous, intramuscular, intra-articular, intrabursal, intestinal, intrathecal, intralesional and intracranial injection or infusion techniques. The pharmaceutical agents of the present invention can also be administered in form of suppositories for rectal administration.

The dose of the pharmaceutical agents of the present invention can vary depending on the activity of a particular compound used, the patient's age, body weight, general health, sex, diet, administration time, administration route, excretion rate, drug combination, and the severity of a particular disease to be prevented or treated. The pharmaceutical agents can be administered at a dose of 0.0001-50 mg/kg/day or 0.001-50 mg/kg/day, depending on the patient's condition, body weight, severity of the disease, the form of drug, administration route and period. The pharmaceutical agents of the present invention may be administered once or several times a day. The dose does not limit the scope of the present invention in any way. The pharmaceutical agents according to the present invention can be formulated as pills, sugar-coated tablets, capsules, liquids, gels, syrups, slurries, or suspensions.

The present invention provides a method of preparing an animal model of brain tumor by inducing p53, Pten and EGFR mutations in SVZ of an animal, preferably a non-human animal.

In the present invention, the term "animal" as used herein refers to any mammals except humans preferably rodents such as mice, rats, guinea pigs, hamsters, more preferably mice. The animals include every age of animals including embryos, fetuses, neonates, and adults. The animals for use in the present invention can be provided by, for example, commercial sources.

In the present invention, the term "animal model" as used herein refers to a non-human animal having a disease whose form is very similar to the disease of human. By the physiological or genetic similarities between human and animals, the biomedical disease model animals provide materials for research of the various causes of diseases, the pathogenesis, and the diagnosis in the disease research. By studying the disease model animals, basic materials of finding the disease-related genes out, understanding interactions among genes, and determining the possibility of practical use can be provided.

The animal model of the present invention has a somatic cancer including brain tumor, for example, glioma or glioblastoma. Specifically, glioma or glioblastoma is occurred in the cortex region separated from SVZ having mutations. The SVZ region shows normal cell structures, and the NSCs having oncogenic mutations migrate from SVZ and induce glioma by abnormal growth of oligodendrocyte-precursor cells (OPCs). The glioma of the animal model was determined high grade glioma according to the hematoxylin and eosin staining (H&E staining) result of the tumor tissue that representing the characteristics such as microvascular proliferation and mitosis. The glioma of the animal model showed immunoreactivity to GFAP, Nestin, Olig2, and PDGFRα, and was developed by migration of neural stem cells (NSCs) having self-renewal and proliferative capacities in SVZ to dorsolateral side. The somatic oncogenic mutations, for example, Trp53, Pten, and EGFR mutants, are able to develop malignant glioma from NSCs in SVZ. Accordingly, the animal model using Trp53, Pten, and EGFR mutants have glioblastoma that reflects the phenomenons of human patients that the glioblastoma arose from GFAP-positive NCSs.

The method of preparing the animal model of brain tumor can comprise following steps: (a) preparing an epidermal growth factor receptor (EGFR) mutant animal; (b) preparing a vector knocking out p53 and Pten; and (c) injecting the vector prepared in step (b) into the subventricular zone (SVZ) of the animal prepared in step (a) by electroporation.

The brain tumor can be malignant glioma, preferably glioblastoma (GBM). The SVZ can comprise a neural stem cell in SVZ, preferably refers to NSCs in the SVZ. In one embodiment of the present invention, the brain tumor was arisen in 90% of mice, and their median survival was 20 weeks when the method of preparing the animal model of brain tumor was applied (FIG. 25e).

The step of preparing the EGFR mutant animal prepared in the step (a) may include a method to commercially purchase an animal having the target mutant. The EGFR mutant can be, for example, an EGFR knockout, preferably an EGFRviii mutant (FEBS J. 2013 November; 280 (21): 5350-70).

In one embodiment of the present invention, LoxP-Stop-LoxP EGFRvii f/+; LoxP-Stop-LoxP tdTomato f/+ were prepared by mating a LoxP-Stop-LoxP EGFRviii mouse (FVB strain) purchased from NCI mouse repository and a LoxP-Stop-LoxP-tdTomato mouse (C57BL/6) purchased from The Jackson Laboratory.

The vector knocking out p53 and Pten prepared in the step (b) described above may be a vector used in gene editing. For example, but not limited to, vectors for homologous recombination, TALEN, zinc finger nuclease (ZFN), or CRISPR-Cas9 can be used. A person skilled in the art can select any appropriate vector by needs regardless of types of vectors as long as the vector can knock out p53 and Pten.

In one embodiment of the present invention, the vectors knocking out p53 and Pten were CRISPR-Cas9 vectors comprising sgRNA targeting p53 or Pten respectively that had been prepared by recombining genome-editing tested sgRNA and a CRISPR-Cas9 vector (FIG. 25a).

The CRISPR-Cas9 vector can be used by synthesizing using methods well known in the art or by purchasing commercially.

The genome-editing test of sgRNA can be carried out by methods well known in the art. Preferably, the genome-editing efficiency may be calculated by T7 Endonuclease I assay (T7E1 assay; NEB) after transduction.

The genome-editing test of sgRNA can additionally include a process to calculate mutation frequency.

The sgRNA targeting p53 may comprise SEQ ID NO: 29, and the sgRNA targeting Pten may comprise SEQ ID NO: 30.

The genome-editing frequency of the sgRNAs can be, but not limited to, the mutation frequency of 30 to 99.9%, 40 to 99.9%, 45 to 99.9%, 50 to 99.9%, 55 to 99.9%, 60 to 99.9%, 65 to 99.9%, 70 to 99.9%, 75 to 99.9%, 80 to 99.9%, 85 to 99.9%, 30 to 95%, 40 to 95%, 45 to 95%, 50 to 95%, 55 to 95%, 60 to 95%, 65 to 95%, 70 to 95%, 75 to 95%, 80 to 95%, 85 to 95%, or 50 to 90%.

In the step (C) described above, genes are transferred specific to the SVZ, the NSCs region, by inserting the vector by electroporation. The electroporation method can overcome the risk that genes were transferred to the other regions besides the SVZ.

In the step (C) described above, dose of the vector can be, but not limited to, 0.1 to 10ng, 0.1 to 8ng, 0.1 to 6ng, 0.1 to 5ng, 0.1 to 4ng, 0.1 to 3ng, 0.1 to 2.7ng, 0.1 to 2.5ng, 0.5 to 10ng, 0.5 to 8ng, 0.5 to 6ng, 0.5 to 5 ng, 0.5 to 4ng, 0.5 to 3ng, 0.5 to 2.7ng, 0.5 to 2.5ng, 1 to 10ng, 1 to 8ng, 1 to 6ng, 1 to 5ng, 1 to 4ng, 1 to 3ng, 1 to 2.7ng, 1 to 2.5ng, 1.5 to 10ng, 1.5 to 5ng, 1.5 to 6ng, 1.5 to 5ng, 1.5 to 4ng, 1.5 to 3ng, 1.5 to 2.7ng, or 1.5 to 2.5ng, preferably 2ng. The amount of vector inserted can be appropriately modified according to the technical knowledge in the art as required.

In one embodiment of the present invention, the brain tumor arose in 90% of mice as the result of a pU6-sgP53-pU6-sgPTEN_CBh-Cas9-P2A-Cre plasmid injection to a LoxP-Stop-LoxP EGFRvii f/+; LoxP-Stop-LoxP tdTomato f/+ mouse. On the other hand, the brain tumor did not arise in mice simply electroporated a sgLacz-targeting CRISPR-CAS9 vector (control). Accordingly, the result suggests that the brain tumor was induced by the mutations inserted, not by the shock of electroporation.

The present invention provides an animal model of brain tumor that p53 Pten and EGFR mutations are induced to an animal, preferably any mammals except humans. More specifically, an animal model that the p53 and Pten knockout mutants are induced specific to the SVZ of EGFR knockout animal is provided.

The p53, Pten and EGFR mutations may correspond to mutations in human patient group. Preferably, the p53, Pten and EGFR mutations can be p53, Pten, and EGFR knockout mutations, for example, but not limited to, indels of few nucleotides or frameshift. The mutations can be freely selected within the range of objectives to lose the function of proteins encoded by p53, Pten and EGFR genes.

The loss of protein functions may include every following case: when the proteins do not expressed, when the proteins expressed but not active, and when the protein activities are significantly inhibited compared to the wild type proteins.

The animal model of the present invention may have the incidence of brain tumor with more than 50%, more than 60%, more than 70%, or more than 80%, for example, 50 to 100%, 60 to 100%, 70 to 100%, 75 to 100%, 80 to 100%, 80 to 100/a, 85 to 100%, 50 to 99%, 60 to 99%, 70 to 99%, 75 to 99%, 80 to 99%, 85 to 99%, 50 to 95%, 60 to 95%, 70 to 95%, 75 to 95%, 80 to 95%, or 85 to 95%.

In one embodiment of the present invention, the brain tumor arose in 90% of mice that the CRISPR/Cas9 vector comprising sgRNA targeting Trp53, or Pten had been injected. On the other hand, the control group that sgRNA targeting LacZ had been introduced did not form the brain tumors. Accordingly, it is certified that the animal model provided by the present invention is suitable as a brain tumor model.

In one embodiment of the present invention, variants in sgRNA analyzed by amplicon sequencing represented the result that the frequency of Trp53 genes comprising one of SEQ ID NO: 38 to 40 were about 80%, and the frequency of Pten genes comprising one of SEQ ID NO: 41 to 43 were about 80%.

The average life span of the mouse models in the present invention may be 10 to 50 weeks, 10 to 40 weeks, 10 to 35 weeks, 10 to 30 weeks, 10 to 28 weeks, 10 to 25 weeks, 12 to 50 weeks, 12 to 40 weeks, 12 to 35 weeks, 12 to 30 weeks, 12 to 28 weeks, or 12 to 25 weeks.

The animal model of the present invention has a characteristic that the mutation insertion region and the tumor developing region are separated. Preferably, the tumor may be developed on the region migrated to dorsolateral from the region the mutation inserted, and the separation distance can be, but not limited to, 1 to 40 mm, 3 to 35 mm, or 5 to 30 mm.

The animal model of the present invention has a characteristic that the SVZ having the Trp53, Pten, and EGFR mutants shows mutant genotypes but their phenotype remains normal tissue. Accordingly, the mutation injected region may not develop tumors.

In the animal model of the present invention, the Trp53, Pten, and EGFR mutations can be present on the electroporation region, for example, specific to NSCs in SVZ.

In one embodiment of the present invention, high-grade glioma having characteristics such as necrosis, microvascular proliferation, and mitosis was observed by analyzing brain tumor of a mouse model (FIG. 20). Additionally the characteristics of human glioma having immunoreactivity to GFAP, Nestin, Olig2 and PDGFRα, more specifically characteristics that glioblastoma is developed from GFAP-positive NSCs in the SVZ was observed, and the high proliferation ability was identified by Ki67.

Specifically, the animal model of brain tumor provided by the present invention directly reflect phenomenon in a human patient that glioblatoma is developed from GFAP-positive NSCs in the human SVZ.

More specifically, the animal model of the present invention has a characteristic that the mutant cell of frontal SVZ the mutation injected migrates to dorsolateral direction and forms tumor, while the frontal SVZ the mutation injected remains normal tissue.

In one embodiment of the present invention, it was determined by using tdTomato marker that the SVZ that mutations were first injected keeps normal structure and still it comprises NSCs having the mutations at the same time. In other words, the NSCs-specific mutations in SVZ were remained after occurrence of glioma. The mutations were identified in the tdTomato-positive NSCs as the result of gene analysis after separating using laser microdissection. Consequently, because the genetic mutations in primary region were kept even after tumor development, this characteristic can be used for further researches such as a study about the function of the mutant stem cells left in primary region, molecular mechanisms, and screening a novel agent for treating or preventing brain tumor.

The animal model of brain tumor of the present invention can be effectively used for researches about the function of genes, molecular mechanisms of brain tumor, screening novel anti-brain tumor agents for preventing or treating.

Accordingly, as another embodiment, the present invention relates to a method of screening a therapeutic agent for brain tumor comprising the step of administering a candidate agent for brain tumor treatment to a glioma-induced animal, followed by confirming whether or not the brain tumor is alleviated or treated.

Specifically, the animal that induced brain tumor can be usefully used for screening a therapeutic agent of brain tumor by confirming whether or not the brain tumor is alleviated or treated under conditions with or without a candidate agent for brain tumor treatment. Any substances reducing brain tumor symptoms directly or indirectly can be selected as a brain tumor treating agent. In other words, a result of observing symptoms of brain tumor without a candidate agent of brain tumor, and a result of observing symptoms of brain tumor with a candidate agent of brain tumor are compared and the substance that brain tumor symptoms were reduced in the presence of the candidate agent compare to absence of the candidate agent can be predicted as the brain tumor treating agent.

The step confirming whether or not the brain tumor is alleviated or treated can comprise measuring the gene expression level or protein activity level of markers of brain tumor. The markers of brain tumor can be, but not limited to, at least one marker selected from the group consisting of NeuN, nestin, GFAP, OliG2, S100b, MBP and Ki67. A person skilled in the art can freely select any brain tumor marker known in the art.

The expression or activity levels of proteins can be measured at least one method selected from the group consisting of Western blotting, radioimmunoassay (RIA), radioimmunodiffusion, enzyme-linked immunosorbent assay (ELISA), immunoprecipitation (IP), flow cytometry, immunofluorescence, ouchterlony, complement fixation assay, and protein chip.

The step that measuring the expression or activity levels of proteins can be carried out by measuring mRNA transcription level. The mRNA may be mRNA transcribed from a gene encoding the protein, or mRNA transcribed from a gene targeted by the protein.

The mRNA level can be measured, but not limited to, by at least one method selected from the group consisting of polymerase chain reaction (PCR), reverse transcriptase PCR (RT-PCR), real-time PCR, RNase protection assay (RPA), microarray, and Northern blotting.

The administrating method of the candidate agent can be administrate by any routes selected by common knowledge in the art such as subcutaneous injection, intramuscular injection, ophthalmic ointment, eye drop, ear drop, inhalation, rectal administration, oral administration, sublingual administration, and transdermal administration.

In the present invention, the term "candidate agent" as used herein refers to a substance subjected to test as a therapeutic agent for brain tumor, preferably glioblastoma. The candidate agent may comprise any molecules such as an extract, a protein, an oligopeptide, a small organic molecule, a polysaccharide, a polynucleotide and a compound in broad range. The candidate agent can also comprise a synthetic substance as well as a natural substance.

Effect of the Invention

The present invention provides an animal model of brain tumor and a preparation method thereof. More specifically, an animal model that directly reflects the phenomenon in a human patient that glioblastoma is occurred from GFAP-positive neural stem cells in human SVZ, and a method of preparing the same are provided. The animal model and the preparation method can be usefully applied in a diagnosis method of human brain tumor, screening a therapeutic agent and developing a novel drug.

Additionally, the present invention can predict the tissue origin of brain tumor of unknown primary. Accordingly, the present invention allows establishment of an appropriate treatment strategy by determining a target region of treatment that maximize treating effect of the brain tumor.

BRIEF DESCRIPTION OF DRAWINGS

FIG. 1 is a schematic presentation for deep sequencing analysis using samples separated from IDH-wildtype BGM patients in one embodiment of the present invention.

FIG. 2 is a picture of the sampling sites of GBM tumor samples and tumor-free SVZ tissue samples in IDH-wildtype GBM patients (left) and a 3D-reconstructed MRI image showing the distance between the tumor-margin and the sampling site of SVZ tissue (right) in one embodiment of the present invention.

FIG. 3 shows VAFs scatterplots of mutations in SVZ tissues without tumor and GBM tumor tissues of 2 patients of IDH-wildtype GBM (GBM187, GBM26) in one embodiment of the present invention.

FIG. 4 shows VAFs scatterplots of mutations in SVZ tissues without tumor and GBM tumor tissues of 4 patients of IDH-wildtype GBM (GBM245, GBM276, GBM499, GBM520) in one embodiment of the present invention.

Figure 5:
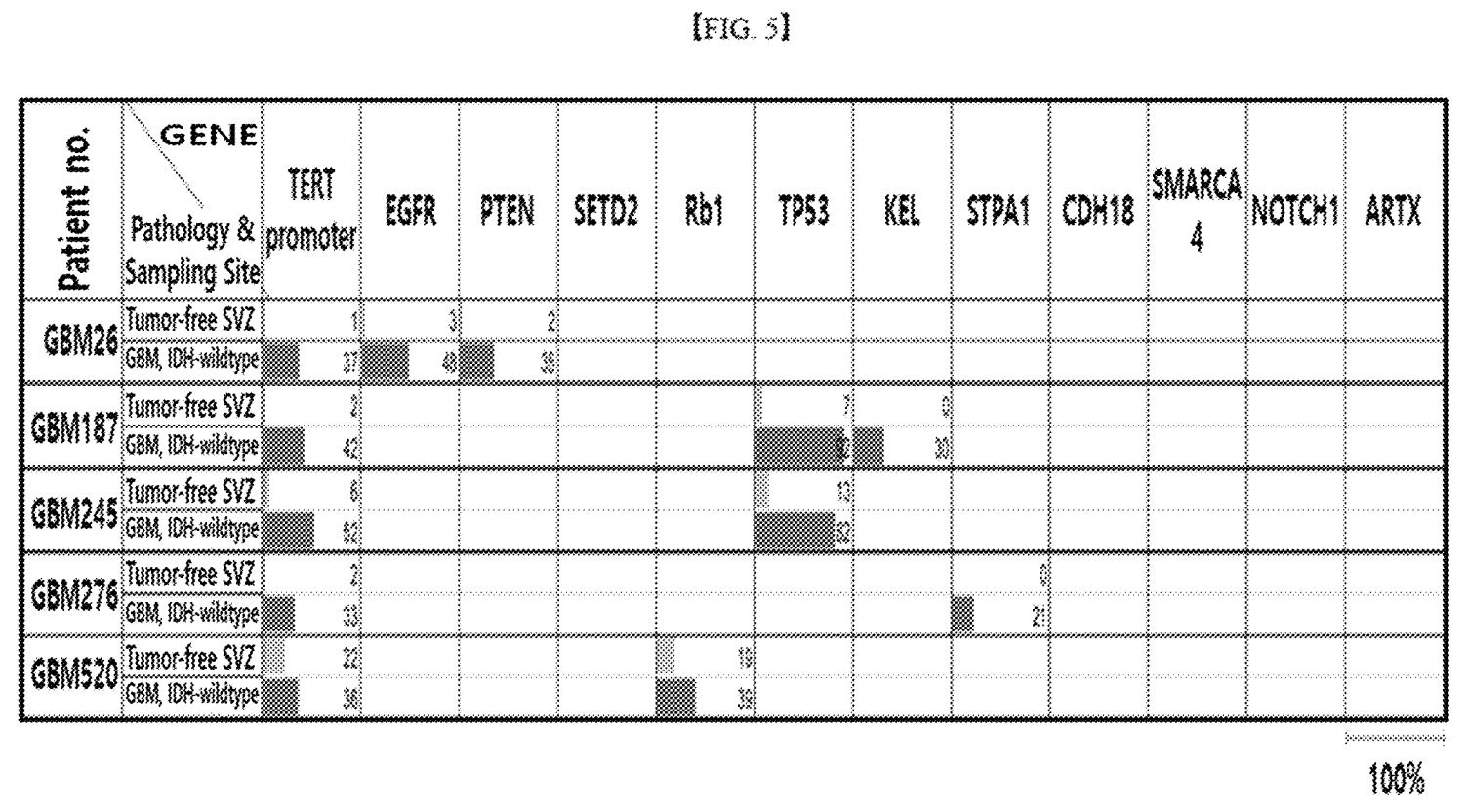

FIG. 5 is a table showing VAFs of mutations measured in SVZ tissues without tumor and GBM tumor tissues of IDH-wildtype GBM patients in one embodiment of the present invention.

FIG. 6 is a VAFs scatterplot of mutations in SVZ tissue without tumor and GBM tumor tissue of a patient of IDH-mutant GBM (GBM160) in one embodiment of the present invention.

FIG. 7 is a VAFs scatterplot of mutations in SVZ tissue without tumor and meningioma tissue of a patient of meningioma (MEN246) in one embodiment of the present invention.

FIG. 8 is a table shing VAFs of mutations measured in SVZ tissues without tumor and GBM tumor tissues of tumor patients except GBM, or patients GBM is invaded to SVZ (GBM146) and a IDH-mutant GBM patient (GBM261) in one embodiment of the present invention.

FIG. 9 is a bar graph representing VAFs of mutations shared in SVZ tissues presence or absence of GBM tumor in IDH-mutant GBM patients in one embodiment of the present invention.

FIG. 10 is a VAFs scatterplot of mutations in SVZ tissue without tumor and GBM tumor tissue of a patient of IDH-wildtype GBM that GBM is invade to SVZ (GBM146) in one embodiment of the present invention.

FIG. 11 is a bar graph representing VAFs of mutations shared in SVZ tissue without tumor and GBM tumor tissue of a patient of IDH-wildtype GBM that GBM is invade to SVZ (GBM160) in one embodiment of the present invention.

FIG. 12 is a graph showing CNVs results of EGFR mutants measured in GBM tumor tissue and tumor-free SVZ tissue of IDH-wildtype GBM patient in one embodiment of the present invention.

FIG. 13 represents a result of single cell Sanger sequencing for passenger mutation only in tumor and shared mutation in GBM tumor tissue and SVZ in an IDH-wildtype GBM patient (GBM185) in one embodiment of the present invention.

FIG. 14 represents a result of single cell Sanger sequencing for passenger mutation only in tumor and shared mutation in GBM tumor tissue and SVZ in an IDH-wildtype GBM patient (GBM520) in one embodiment of the present invention.

FIG. 15 shows the result of CNVs in tumor tissues and SNV tissues based on the deep WES data in one embodiment of the present invention. (a) The CNVs result in IDH-wildtype GBM patient having mutations in GBM tumor tissues shared with SVZ. (b) The CNVs result in IDH-mutant GBM patients and meningioma patients. (c) The CNVs result of a IDH-wildtype GBM patient that the GBM is invaded to SVZ.

FIG. 16 is a result of the laser capture microdissection (LCM) after deep amplicon sequencing in an IDH-wildtype GBM patient in one embodiment of the present invention.

FIG. 17 is the results of site-specific amplicon sequencing analysis relate to TERT C228T mutant in the microdissected astrocytic ribbon in one embodiment of the present invention.

FIG. 18 shows the mutation spectra incorporating the substitution type of mutations in GBM tumor tissue and tumor-free SVZ, and SVZ of IDH-wildtype GBM patient that GBM is invaded to SVZ in one embodiment of the present invention.

FIG. 19 is a graph showing contributions of signature 1, signature 5 and other signatures in GBM tumor tissue and tumor-free SVZ of IDH-wildtype GBM patients and GBM invaded SVZ of IDH-wildtype GBM patient GBM invaded in one embodiment of the present invention.

FIG. 20 shows the glioma progression in the mouse model carrying low-level driver mutations in NSCs from the SVZ in one embodiment of the present invention. (a) Experimental scheme showing the procedure for electroporation of a plasmid containing sgRNAs. (b) Representative images of serial sections from mice at 13 and 16 weeks after electroporation. (c)-(e) Representative images of immunostaining or H&E staining in P53/PTEN/EGFR mutant mice with high-grade glioma in the caudal cortex in one embodiment of the present invention.

FIG. 21 is a schematic showing the imaging analysis of tdTomato-positive cells in the caudal cortical region, and a graph representing quantification of the relative intensities of tdTomato signals in the caudal cortical regions at each time point in one embodiment of the present invention.

FIG. 22 is representative images of histology and MRI and the proportion of the location of the tumor in one embodiment of the present invention.

FIG. 23 is the representative immunostaining images of OLIG2-, PDGFRα-, GFAP- and tdTomato-positive cell regions at the caudal cortex, and the graph of propositions of the cells positive to neuron, oligodendrocyte, astrocyte, OPCs respectively in one embodiment of the present invention.

FIG. 24 is an illustration of the progress of migration and tumor development via the aberrant growth of OPCs in one embodiment of the present invention.

FIGS. 25*a* to *j* show development of high-grade glioma in genome-edited mice harboring P53/PTEB/EGFR mutations in the SVZ in one embodiment of the present invention. (a) The map of a single vector expressing Cas9 and Cre recombinase with the sgRNAs targeting p53/Pten. (b) In vitro screen of sgRNAs targeted to p53 and Pten in the Neuro-2a cell line. (c) Immunostaining image of neural stem cells at 3 days after electroporation. Scale bars, 50 um. (d) A scatter dot graph showing the percentage of tdTomato-positive cells co-stained with nestin or GFAP. (e) A Kaplan-Meier survival graph of mice (10 mice in each group, P=0.000063, log-rank test). (f) Representative H&E-stained images reflect the classical features of high-grade glioma, such as necrosis microvascular proliferation (M), and mitoses (arrow). (g) Representative MRI images of the 3 mice 16 weeks after the electroporation. (h) Immunostaining of various high-grade glioma-related markers, including nestin, GFAP, OLIG2, S100β, MBP and Ki67, as well as the neural maker NeuN, in tumors. (i) The bar graph shows the percentage of sequencing reads with indels in one high-grade glioma from mutant mice, using site-specific amplicon sequencing. j) Detection of EGFRviii (360 bp) in tumors from mutant mice using qRT-PCR. Actb was used as an internal control.

MODES FOR INVENTION

Hereinafter, the present invention will be described in more detail through the Examples.

The Examples are only for describing the present invention in more specifically. Based on the gist of the present invention, it will be obvious to those skilled in the art that the scope of the present invention is not limited by these Examples.

[Preparation Examples 1] Sample Preparation

To examine the somatic mutations in normal SVZ tissue away from the tumor mass, 55 specimens including i)

pathologically and radiographically normal SVZ tissue with a safe distance from the tumor, ii) tumor tissue, and iii) unaffected normal cortical tissue or blood were obtained from 17 patients having isocitrate dehydrogenase (IDH)-wildtype GBM (primary GBM), IDH-mutant GBM (secondary GBM), or meningioma, oligodendroglioma, and mestatic cancer (FIG. 1).

The patients enrolled in our study underwent supra-total resection or other surgical resection of tumors located primarily in the temporal lobe, providing access to normal SVZ tissue away from the tumor mass, under the assistance of a magnetic resonance imaging (MRI)-based navigation system (FIG. 2). Tumor-free SVZ tissue was resected at a safe distance from the tumor margin on reconstructed three-dimensional MRI images, ranging from 5.3 to 33.3 mm. The collected SVZ samples were confirmed for tumor-free conditions by histological examination. In addition, the i) and iii) specimens described above were collected from two patients in whom GBM had invaded SVZs as a positive control.

[Preparation Examples 2] Gene Expression Microarray Datasets and Subtype Classification Total RNA was extracted from GBM tumour samples using a Qiagen RNeasy kit (Qiagen) according to the manufacturer's procol. Expression profiles were obtained using an Illumina Human HT-12 v4 Expression BeadChip. Raw at a were variance stabilizing transformed normalized with the quantile normalization method using R/Bioconductor lumi package, and then standardized into [0, 1] by (values–MTN)/(MAX–MIN). The four gene signatures of GBM (Verhaak, R. G. W. et al. An integrated genomic analysis identifies clinically relevant subtypes of glioblastoma characterized by abnormalities in PDGFRA, IDH1, EGFR and NF1. Cancer cell 17, 98, (2010)) were projected onto the gene expression data. To determine the subtypes of samples, enrichment scores for each subtype were generated using single sample gene set enrichment analysis (ssGSEA).

[Preparation Examples 3] Deep Whole-Exome Sequencing (WES) in Patient's Tissues Genomic DNA was extracted with either the Qiamp mini DNA kit (Qiagen) for freshly frozen brain tissues or the Wizard Genomic DNA Purification Kit (Promega) for blood following the manufacturers' instructions. Each sequenced sample was prepared according to Agilent library preparation protocols (Agilent Human All Exon 50 Mb kit). Libraries underwent paired-end sequencing on an Illumina HiSeq 2000 and 2500 instrument (average read depth of 392x) according to the manufacturer's protocol. The analysis-ready bam files from Fastq files were generated according to the 'best practices'workflow designed by the Broad Institute. In brief, raw sequences were aligned from the fastq file to reference genome using BWA (http://bio-bwa.sourceforge.net) to generate sam files. The sam files were converted to bam files and conducted the marked duplicate using Picard (http://broadinstitute.github.io/picard). Then, indel artefacts in these bam files were cleaned up using RealignerTargetCreator and IndelRealigner in GATK analysis tools (http://www.broadinstitute.org/gatk/download). Next, the present inventors performed base quality score recalibration using BaseRecalibrator in GATK analysis tools for the accurate variant calling.

[Preparation Examples 4] Deep Sequencing of Glioma-Related Genes

Hybrid capture probes for 79 glioma-related genes were designed using SureDesign online tools (Agilent Technologies). Glioma-related genes included TCGA GBM exome sequencing results of significantly mutated genes (allele frequency (AF)>2%) and meaningful genomic data (driver genes and functional pathways involved in grade II or III glioma) from large cohorts of grade II and III gliomas from Japan (JPN) and The Cancer Genome Atlas Research Network (TCGA) Consortium (Brennan, C. W. et al. The somatic genomic landscape of glioblastoma. Cell 155, 462-477, (2013); Suzuki, H. et al. Mutational landscape and clonal architecture in grade II and III gliomas. Nat Genet 47, 458-468, (2015)). Genomic DNA (>200 ng) was sheared, and the DNA fragments were end-repaired, extended with an 'A' on the 3' end, ligated with paired-end adaptors, and amplified (6 cycles). Adaptor-ligated libraries were hybridized for 24 h with biotinylated oligonucleotide RNA baits and enriched with streptavidin-conjugated magnetic beads. The final libraries were further amplified for 16 cycles with PCR and sequenced on an Illumina HiSeq 2500 sequencer (median read depth of 655x). Then, the present inventors generated an analysis-ready bam file using GATK best practice data cleanup pipeline. These barn files were converted to pileup files using Samtools (http://samtools.sourceforge.net).

[Preparation Examples 5] Site-Specific Amplicon Sequencing of Mutations in TERT Promoter A target region is designed to flank C228T and C250T mutations in TERT promoter, corresponding to c.-124C>T and c.-146C>T of TERT. This region was amplified by PCR using the primers (a forward primer: AGCACCTCGCGGTAGTGG; and a reverse primer: GTCCTGCCCCTTCACCTT (SEQ ID NO: 2)). This region was amplified by PCR using targeted primers, including six base-pair index sequences. PCR was performed using PrimeSTAR GXL (Takara, Japan) high-fidelity DNA polymerase under optimized thermal conditions. Then, DNA library was prepared according to the TruSeq DNA sample preparation guide. In brief, end repair and addition of 3'A overhangs were performed using the TruSeq DNA kit (Illumina, USA).

Indexed TruSeq adaptors were ligated according to the manufacturer's protocol and purified with AMPure beads (Agencourt Bioscience, USA). DNA fragments of 386 bp (274 bp of DNA plus 55 bp of adaptors with 57 bp of index) were excised from agarose gel and purified using the Mini elute gel extraction kit (Qiagen, USA). Then, the present inventors performed enrichment of DNA fragments that had adaptor molecules on both ends to amplify the amount of DNA in the library using PCR primer cocktail and master mix (Illumina, USA). Libraries were pooled and sequenced on a Hiseq sequencer (IlluminaSA) (median read depth of 917,384x). Then, the present inventors sorted raw sequences from the Hiseq sequencer by index to generate patient-specific fastq files using in-house transcripts. The sorted sequences were aligned by Bowtie2 (http://bowtie-bio.sourceforge.net/bowtie2/index.shtml) and a barn file was generated. The bam file was converted to pileup files using Samtools (http://samtools.sourceforge.net).

[Preparation Examples 6] Validation Sequencing of Candidate Variants

To validate the candidate variants, the present inventors used Sanger sequencing of PCR-amplified DNA for variants. Primers for PCR amplification were designed with Primer3 (http://bioinfo.ut.ee/primer3-0.4.0/) (Untergasser, A. et al. Primer3Plus, an enhanced web interface to Primer3. Nucleic Acids Res 35, W71-74, (2007)). PCR was performed using PrimeSTAR GXL (Takara, Japan) high-fidelity DNA polymerase under optimized thermal conditions. PCR products were evaluated on agarose gels. Sanger sequencing was performed using Big Dye Terminator reactions and subsequent loading on an Applied Biosystems 3730Eq DNA analyser (Applied Biosystems, USA). For the candidate variants with low variant frequency <10% or undetermined in Sanger sequencing, site-specific amplicon sequencing described above was used. The present inventors validated 104 (11.0%) out of 946 GBM-related mutations and randomly selected mutations, of which mutational burdens ranged from 1.9% to 99.1%. Of validated targets, the present inventors confirmed 96 out of 104 mutations. VAF calculated by site-specific amplicon sequencing replaced VAF of WES to analyse the clonal relationship between SVZs and tumors.

[Preparation Examples 7] Real-Time Quantitative PCR

Real-time qPCR was performed using iQ™ SYBR® Green Supermix (Biorad, USA) in the thermal cycler system (CFX-96, Biorad, USA) following the manufacturer's protocol. The presence of CNVs was confirmed using specific primers for the EGFR sequence, RNase P, and LDHA (Table 2) designed using Primer3 (http://frodo.wi.mit.edu). Thermal cycling consisted of one cycle with initial denaturation and enzyme activation at 95° C. for 3 min, followed by 40 cycles at 95° C. for 10s and annealing and extension at 55-60° C. for 30 s. The relative fold changes, compared to blood or normal brain tissue, were determined using the relative normalized expression method calculated by CFX Manager™ Software.

using MPprimer (http://biocompute.bmi.ac.cn/MPprimer/). These mutation regions were amplified by multiplex PCR using the two primer sets. The single nuclei PCR was performed using HotStarTaq DNA polymerase (Qiagen, USA) under optimized thermal conditions.

[Preparation Examples 9] Laser Capture Microdissection (LCM)

Formalin-fixed, paraffin-embedded tissue sections from tumor-free SVZ were collected and placed on glass slides. The slides were deparaffinized with xylene and rehydrated. Heat-induced antigen retrieval was performed with 90° C. for 20 min in Tris-EDTA buffer. The slides were blocked in PBS-GT for 1 h at room temperature and stained with mouse antibody to GFAP (1:500; G3893, Sigma) and rabbit antibody to S100β (1:500; ab52642, abcam). Samples were then washed in PBS and stained with the secondary antibodies Alexa Fluor 488-conjugated to rabbit (1:500 dilution; Invitrogen) and Alexa Fluor 555-conjugated to mouse (1:500 dilution; Invitrogen). Samples were washed in PBSagain and incubated in PBS with 300 nM DAPI. After performing immunofluorescence staining with GFAP, S100β antibodies, and DAPI, the ependymal layer, hypocellular gap, and dense ribbon of cell bodies in SVZs were identified microdissected with the PALM laser capture system (Carl Zeiss, Germany). Genomic DNA was extracted from collected cells using a QiAamp micro kit (Qiagen, USA). The target region flanking C228T mutation of TERT promoter was amplified by PCR using targeted primers and high-fidelity PrimeSTAR GXL DNA polymerase (Takara, Japan). Amplified PCR product was purified and then site-specific amplicon sequencing described in Preparation Examples 5 was performed.

TABLE 2

| Gene | Locus | Forward | Reverse | Product size |
|------|-------|---------|---------|--------------|
| EGFR | Ch7:55229262-55229347 | CGTCTCTTGCCGGA ATGT (SEQ ID NO: 23) | GGATTAAAGAAATAAC CTCCTACCC (SEQ ID NO: 24) | 86 |
| RNaseP | Chr15:75246734-75246832 | GGGAGATGCGGAA GAATGT (SEQ ID NO: 25) | CCTCCAGTCAGCCACAG AA (SEQ ID NO: 26) | 99 |
| LDHA | Chr11:18408413-18408534 | ACTGTGACCCTTAT CCAGGC (SEQ ID NO: 27) | CTTCCCTTAACTAGCTC TCAGGA (SEQ ID NO: 28) | 122 |

[Preparation Examples 8] Single-Cell Cloning Preparation with Subsequent Sanger Sequencing Single nuclei were isolated from fresh frozen tumor samples. More specifically, tissue samples were placed in NST-DAPI buffer and teased apart and homogenized with scalpels. After free nuclei were confirmed visually using fluorescence microscopy, nuclei stained with DAPI were analysed by FACS. Single nuclei were sorted from the DAPI-positive population. For subsequent Sanger sequencing, the present inventors selected representative shared driver and tumor-private mutations with a high variant allele frequency in tumor samples. Two primer sets to flank the sites of tumor-private and shared mutations were designed

[Preparation Examples 10] Analysis of Mutation Signature

To determine the contributions of mutational process, a multiple regression approach, deconstructSigs (Rosenthal, R., McGranahan, N., Herrero, J., Taylor, B. S. & Swanton, C. DeconstructSigs: delineating mutational processes in single tumors distinguishes DNA repair deficiencies and patterns of carcinoma evolution. Genome Biol 17, 31, (2016)) was performed to extract signatures based on the COSMIC signature framework (http://cancer.sanger.ac.uk/cosmic/signatures). Final inputs of mutations were 261 from 11 tumor-free SVZs, 812 from 9 GBMs, 60 from 1 GBM-invaded SVZ.

[Examples 1] Identification of Mutations in Tumor-Free SVZ and Tumor

The following experiments were performed based on a hypothesis that if the normal SVZ samples away from tumor obtained by the method of the Preparation Example 1, mutation burden or variant allele frequency (VAF) would be lower than tumor. Specifically, deep sequencing analysis were performed for the specimens of i) and iii) to identify low-level somatic mutations in the tumor-free SVZ. In briefly, deep whole exome sequencing (average read depth of 392×) in 34 samples, 2 telomerase reverse transcripase (TERT) promoter site in 61 samples (average read depth or 948,608×), deep targeted sequencing in 79 glioma-related genes known by Cancer Genome Atlas Brennan, C. W. et al. The somatic genomic landscape of glioblastoma. Cell 155, 462-477, (2013); Suzuki, H. et al. Mutational landscape and clonal architecture in grade II and III gliomas. Nat Genet 47, 458-468, (2015))(Table 3) of 18 samples (average read depth of 601×) were performed. Recently, the mutations on upstream of 124 bp (C228T) and 146 bp (C250T) from TERT ATG start site are reported as oncogenes in 83% of GBM patients. And somatic mutations of all exons and TERT promoter sites were investigated using Strelka algorithm (https://sites.google.com/site/strelkasomaticvariant-caller/) and Integrative Genomic Viewer of aligned bam files, and VAFs were measured in SVZ and tumor tissue. Somatic mutations were not identified only in the samples from unaffected brain or blood tissue among specimens obtained from patients. Among tissues analyzed with deep WES, the present inventors identified an average of 25.2 somatic mutations in each tumor-free SVZ specimen and 86.3 in each tumor specimen. To validate somatic mutations, the present inventors performed Sanger sequencing or site-specific amplicon sequencing using primers described in Table 3 above, and 92.3% of selected somatic mutations (96 of 104) were identified as authentic somatic mutations. It is discovered that 47% of the patients (8 of 17) had at least one somatic mutation in the coding or TERT promoter region of TP53 in their tumor-free SVZ tissue. VAFs of these mutations in SVZ were measured with 1% to 22%. Interestingly, the TERT promoter mutations were found in all of the IDH-wild-type GBM patients with driver mutations in tumor-free SVZ tissue. The VAFs of the driver mutations were measured much higher, about 29% to 92%, in tumor tissue than SVZ (FIG. 9). Meanwhile, deep WES in the patients with GBM-invaded SVZ showed that 93% of somatic mutations in tumor were appeared in somatic mutations in the GBM-invaded SVZs, and the VAFs of the mutations were higher in the SVZ than in tumor tissue (FIGS. 8, 10 and 11). Furthermore, the present inventors performed real-time quantitative PCR to analyze EGFR copy number variations (CNVs) often found in GBM and CNVs were found in the tumor-free SVZ tissue. The EGFR amplification was found in 4 of 6 patients of IDH-wild-type GBM patients having driver mutations in tumor-free SVZ tissue (Table 4). Similar to the results of deep WES, the relative EGFR copy numbers were measured significantly higher in tumor tissue than tumor-free SVZ tissue (FIG. 12).

Together, the results indicates that patients with IDH-wildtype GBM share somatic mutations in SVZ and tumor tissue, but the expression level in SVZ is significantly low than tumor tissue.

TABLE 3

| Glioma-related genes |
|---|
| NOTCH1, NOTCH2, PDGFRA, EGFR, PIK3CA, PIK3R1, PTEN, NF1, CIC, ATRX, IDH1, FUBP1, ARID1A, ARID1B, SMARCA4, CDKN2A, TP53, SETD2, MLL2, IDH2, ABCB1, ABCC9, ADAM29, AFM, ANKRD36, BRAF, C1orf150, CALCR, CARD6, CD3EAP, CDH18, CDH9, CDHR3, CDX4, COL1A2, CXorf22, DCAF12L2, DRD5, DYNC1I1, FGA, FOXR2, FRMD7, GABRA1, GABRA6, GABRB2, GPX5, HEATR7B2, IL18RAP, KEL, KRTAP20-2, LCE4A, LRRC55, LUM, LZTR1, MMP13, NLRP5, ODF4, PARD6B, PLCH2, PODNL1, QKI, RB1, RFX6, RPL5, SCN9A, SEMA3C, SEMA3E, SEMG1, SIGLEC8, NRAS, KRAS, CDK4, CDKN2B, FGFR, MDM2, MDM4, MET, CDKN2C, CDK6 |

TABLE 4

| Patient no. | Distance between SVZ and tumor (mm) | Shared mutations | | |
|---|---|---|---|---|
| | | SNV. Indel (VAF, SVZ→tumor) | TERT promoter (VAF, SVZ→tumor) | CNV (fold change, SVZ→tumor) |
| GBM 26 | 13.4 | EGFR:p.Ala289Val (3% → 48%) PTEN:p.Val317fs (2% → 35%) | c228t (1% → 37%) | EGFR (5 → 137) |
| GBM 187 | 18.8 | TP53:p.Cys176Tyr (7% → 92%) | c228t (2% → 42%) | — |
| GBM 245 | 7.2 | TP53:p.Glu285Lys (13% → 82%) | c228t (6% → 52%) | — |
| GBM 276 | 5.3 | — | c228t (2% → 33%) | EGFR (3 → 18) |
| GBM 499 | 7.6 | EGFR:p.Ala289Val (4% → 29%) | c228t (1% → 38%) | EGFR (7 → 83) |
| GBM 520 | 26.6 | RB1:p.Lys202fs (19% → 39%) | c228t (22% → 36%) | EGFR (10 → 21) | tumor-free SVZs that was shared with the matched tumor by deep sequencing analysis (FIGS. 3, 4 and 5). Deep WES in the eight patients revealed that an average of 13.3 somatic mutations per individual was shared between matched tumor and tumor-free SVZ tissue. The shared somatic mutations in the tumor-free SVZ and the matched tumor tissue were only found in patients with IDH-wild-type GBM and not with other types of brain tumor (FIGS. 6, 7 and 8). More surprisingly, 75% (6 of 8) of the patients with IDH wild-type GBM who had somatic mutations shared between SVZ and tumor tissue contained low-level driver mutations in TERT promoter or cancer-driving genes, such as EGFR, PTEN and

[Examples 2] Identification of Origin Region of GBM Tumor

About the result of Examples 1 that somatic mutations are shared in SVZ and tumor tissue of IDH-wild-type GBM patients, but the expression level in SVZ is much lower than in tumor tissue, it can be assumed that clones found in the SVZ gained tumor-private passenger mutations in a tumor development process after driver mutations had gained. The single cell sequencing of tumor sharing driver mutations with SVZ of IDH-wild-type GBM patients were performed, because tumors have to include not only mutations sharing with SVZ private passenger mutations in a single cell level, according to the assumption. More specifically, single nuclei were separated from a patient having a TP53, c.527G>A driver mutation in both of GBM tumor and SVZ and a TCERG1L, c.1127G>A passenger mutation only in GBM (GBM187) using fluorescence-activated cell sorting (FACS).

The VAFs of TP53, c.527G>A and TCERG1L, c.1127G>A were calculated in 91.8% and 87.2% which are similar to mutation level in tumor. And single cell sequencing was carried out for TP53, c.527G>A and TCERG1L, c.1127G>A regions. The result showed 42 of 47 sequenced clones had had both TP53, c.527G>A and TCERG1L, c.1127G>A mutations, 2 other clones had shown normal alleles in both regions (FIG. 13). Clones having either TP53, c.527G>A or TCERG1L, c.1127G>A mutants were not observed. Similarly, for tumors obtained from other IDH-wild-type GBM patient (GBM520), the VAFs of TERT promoter mutation C228T shared with SVZ and a RPS13, c.*3T>G private mutant of tumor were calculated as 36.0% and 40.8% respectively, 12 of 25 sequenced clones had had both of the mutations. Other clones had normal alleles in both regions (FIG. 14), and no clone had either one of 2 mutations. To investigate more the direction of clonal evolution, CNVs pattern were analyzed for all chromosomes in tumor-free SVZ and GBM-invaded SVZ using deep WES data. As a result, tumor-free SVZ did not show the structural abnormalities found in tumor, however, GBM-invaded SVZ showed SNV pattern identical with tumor tissue. Through, it was determined that tumor cells were not the origins of CNVs in tumor-free SVZ likewise single cell sequencing data (FIG. 15).

Accordingly, it is found that cells having driver mutations in tumor-free SVZ away from tumor were transformed and developed GBM.

[Examples 3] Determining Tumor-Driving Region and Cells in Tumor-Free SVZ

Next, the present inventors sought to determine which cell types in tumor-free SVZs harbor the mutations driving GBM. The human SVZ is known to comprise three anatomically distinct layers: the ependymal layer, hypocellular gap, and astrocytic ribbon. Of these three layers, the glial fibrillary acidic protein GFAP-positive, astrocytic ribbon in the SVZ contains astrocyte-like stem cells and the following experiments were carried out to determine whether astrocyte-like stem cells develop driver mutations in SVZ. First, S100β, GFAP, and DAPI immunostaining were performed in order to isolate separately the three layers of SVZ (FIG. 16). 2 patients of GBM499 and GBM198 were both represented low-level TERT promoter C228T mutation in tumor-free SVZ. Next, laser capture microdissection were performed to isolate separately GFAP-positive astrocyte-like stem cells from astrocytic ribbon, S100β-positive ependymal cells from ependymal layer, DAPI-positive cells from hypocellular gap or other regions (FIG. 16). To identify which cells have driver mutations in SVZ, the present inventors performed deep-site specific amplicon sequencing of the TERT promoter in enriched cells of each layer. The TERT promoter C228T mutation was noted only in GFAP-positive, astrocyte-like stem cells from the astrocytic ribbon layer (FIGS. 16 and 17).

Together, these results suggested that astrocyte-like stem cells from the astrocytic ribbon of the SVZ harbor driver mutations and clonally evolve to tumors away from the SVZ.

[Examples 4] Determining the Aetiology of Somatic Mutations in Tumor-Free SVZs To examine the aetiology of somatic mutations in tumor-free SVZs, the present inventors attempted to analyse genetic signatures of the somatic mutations such as intrinsic DNA replication errors, exogenous or endogenous mutagen exposure and defective DNA repair. Mutational characteristics of somatic mutations were analyzed in coding regions of 11 tumor-free SVZs (271 somatic mutations), 9 tumors (845 somatic mutations), and 1 GBM-invaded SVZ (64 somatic mutations) discovered by each deep WES sequencing using DeconstructSigs (FIG. 18). Signatures 1 (33.9%) and 5 (45.4%) were found as major causes in mutation spectrum for tumor-free SVZ. Meanwhile, the Signature 1 was the only dominant signature in tumor (86.2%) and GBM-invaded SVZ (81.5%) (FIG. 19). High proportions of Signature 5 refers to accumulation of somatic mutations, not clearly discovered yet, it had been found that is caused by general genetic aging mechanisms recently. On the other hand, it had been found that high proportions of the Signature 1 refer to mutations based on rapid proliferation.

Together, it was found that somatic mutations in SVZ causing GBM affects natural aging of NSCs having limited self-renewal capacities rather than rapid proliferation of abnormal cells, by the result of high Signature 5 mutation level in tumor-free SVZ

[Examples 5] Preparing Mouse Model of GBM Tumor

To test whether low-level somatic mutations in the NSCs of the SVZ could indeed lead to the formation of GBM away from the SVZ in vivo, a mouse model of Trp53 (also known as p53 or TP53), Pten and EGFR mutations in NSCs from the SVZ through genome editing was prepared: these mutations were recurrent driver mutations found in the tumor-free SVZ tissues from the GBM patients.

5-1. Mouse Experiment Information and Preparation of LoxP-Stop-LoxP EGFRvii f/+:LoxP-Stop-LoxP tdTomato f/+ Mouse All mouse experiments were approved by and performed according to the guidelines of the Institutional Animal Care and Use Committee (IACUC) of the KAIST.

The mice were housed in isolator cages with free access to food and water. The housing room was located in a specific-pathogen-free condition maintained at a constant temperature of 23° C. on a 12-h light-dark cycle with lights off at 19:00. The health status of mouse was examined regularly by the veterinarians and investigators.

Disease Specific Survival (DSS) endpoint was met when the mice died or met the criteria for euthanasia under the IACUC protocol. The criteria for euthanasia were: (i) severe weight loss of more than 20%, (ii) severe neurological impairment including paralysis, seizure and hunched posture with impaired motor power, or (iii) head bulging sign.

A LoxP-Stop-LoxP EGFRvii f/+; LoxP-Stop-LoxP tdTomato f/+ mouse was prepared by mating a LoxP-Stop-LoxP EGFRviii mouse (FVB strain) purchased from NCI mouse repository and a LoxP-Stop-LoxP-tdTomato mouse (C57BL/6) purchased from The Jackson Laboratory 5-2. Construction of the Cre-Expressing CRISPR-Cas9 Vector In order to insert Trp53, Pten, and EGFR mutations to NSCs of mouse SVZ, a single vector containing sgRNAs targeting p53/Pten, Cas9, and Cre recombinase was generated.

Specifically, the pU6-(BbsI)_CBh-Cas9-T2A-BFP plasmid was obtained as a gift from R. Kuehn (Addgene plasmid 64323). sgRNAs targeting p53 (sgP53) and Pten (sgPTEN) were designed using CRISPR tool (http://crispr.mit.edu) to minimize potential off-target effects. sgRNA candidates for p53 and Lacz were designed by a method known in the art (Cancer Cell 28, 429-440 (2015)). sgRNA sequences are shown in Table 5.

TABLE 5

| SEQ ID NO: | Target gene | Sequence (5'→3') |
|---|---|---|
| 29 | Trp53 | GGTGTAATAGCTCCTGCATGG |
| 30 | PTEN | GGTTGGTCAAGATCTTCACAGA |
| 31 | LacZ | GGTGCGAATACGCCCACGCGAT |

Oligonucleotides containing each sgRNA sequence were synthesized by Cosmogenetech and annealed in vitro with a thermocycler. pU6-(BbsI)_CBhCas9-T2A-BFP plasmid was digested with BbsI and ligated with the annealed oligonucleotides.

The genome-editing test with plasmids containing sgRNAs was performed by a method known in the art (Nat. Protocols 8, 2281-2308 (2013)). In brief, Neuro-2a cells were transfected with the plasmids carrying sgRNAs candidates using jetPRIME transfection reagent (Polyplus). After 2 days, genomic DNA was extracted from the treated cells using the Qiamp mini DNA kit (Qiagen) and used as a template for PCR amplification of target regions. T7 Endonuclease I assay (T7E1 assay; NEB) was performed to test the genome-editing efficiency of sgRNA candidates. The T7E1 results shown in FIG. 25b. Mutation frequencies were calculated on the basis of the band intensities with ImageJ software and the following Formula.

$$\text{Mutation frequency}(\%)=100\times(1-(1-\text{fraction cleaved})^{1/2}) \quad \text{[Formula 1]}$$

To generate a single vector containing sgRNAs targeting p53/Pten, Cas9, and Cre recombinase, the present inventors amplified P2A-Cre with AAV:ITR-U6-sgRNA (backbone)-pEFS-Rluc-2A-Cre-WPRE-hGHpA-ITR (a gift from F. Zhang, Addgene plasmid 60226), and then switched T2A-BFP to P2A-Cre in the pU6-(BbsI)_CBh-Cas9-T2A-BFP plasmid. Next, the present inventors amplified pU6-sgP53, pU6-sgPTEN and switched pU6-(BbsI) to pU6-sgP53-pU6-sgPTEN in pU6-(BbsI)_CBh-Cas9-P2A-Cre plasmid to generate pU6-sgP53-pU6-sgPTEN_CBh-Cas9-P2A-Cre plasmid (sgTP-Cas9-Cre). In addition, the present inventors inserted sgLacz to pU6-(BbsI)_CBh-Cas9-P2A-Cre to generate sgLacz-Cas9-Cre. The final vector map was shown in FIG. 25a.

5-3. Insertion of Vectors to Mouse SVZ by Electroporation

The Cre-containing CRISPR-Cas9 vector generated by a method of Examples 5-2 was injected to front SVZ of one side of LoxP-Stop-LoxP EGFRviii f/+; LoxP-Stop-LoxP tdTomato mouse cerebral hemisphere by in vivo electroporation to induce oncogenic mutations to NSCs in specific regions of mouse SVZ and determine mutant cell migration from SVZ.

Specifically, neonate, 2-3-day-old pups (P2-P3) were anaesthetized by hypothermia (over 5 min) and fixed to a support using an adhesive plaster. As a general positional marker, a virtual line connecting the right eye with lambda was used and a capillary needle was inserted at about one-third the length of this line from the eye. The right lateral ventricle was injected at a depth of 2 mm from the skull with 1 μl of plasmid solution (2 ug/ul, containing 1% (v/v) FastGreen). Injection success was achieved with the Fast-Green staining visualizing the shape of the lateral ventricle. Only successfully injected animals were subjected to five electrical pulses (100 V, 50 ms, separated by 950 ms intervals) using the ECM830 electroportor (BTX-Harvard apparatus) and 1-mm tweezer electrodes (CUY650P1, Nepagene). The positive electrode was positioned ahead of the eye, and the negative was placed in the opposite position on the ventral side. After electroporation, mice were placed on a 37° C. heating plate until they fully recovered and were returned to their mother. The transfected cells expressing tdTomato were mainly located on the rostral-dorsolateral side in the anterior horn of the lateral ventricle at post-injection 2 days. However, the transfected cells decreased gradually to the caudal direction and disappeared at the coronal section of the rostral head of the hippocampus.

The immunostaining result of Trp53/Pten/EGFR mutant mice 3 days after electroporation is shown in FIG. 25c. White arrows pointing the regions tdTomato-positive reaction appeared with GFAP or nestin in SVZ. Therefore, it was confirmed that tdTomato-positive cells were localized in SVZ. A scatterplot of cells co-stained with tdTomato-positive and nestin or GFAP is shown in FIG. 25d.

5-4. Identifying Development of Brain Tumor in Mice Model

90% of the electroporated mice (9 of 10) developed brain tumors with a median survival of 20 weeks, whereas no brain tumors were found in control mice simply sgLacz-targeting CRISPR-Cas9 vectors were electroporated (FIG. 25e). The survival rate of electroporated mice compare to control mice is shown in FIG. 25e. 10 mice were used for each group.

Additionally, EGFRviii expression and Trp53 and Pten indels in brain tumor were examined. Specifically, tumor mass separated with a scalpel and genomic DNA was extracted from tdTomato-positive cells in olfactory bulb which are microdissected using laser-microdissection. Trp53 and Pten region of mouse genome are amplified using primers listed in Table 6.

TABLE 6

| SEQ ID NO: | Primer name | Sequence (5'→3') |
|---|---|---|
| 32 | Mouse_Trp53_forward | AGGTAGGGAGCGACTTCACC |
| 33 | Mouse_Trp53_reverse | TAAGGATAGGTCGGCGGTTC |
| 34 | Mouse_Pten_forward | AGACCATAACCCACCACAGC |
| 35 | Mouse_Pten_reverse | TACACCAGTCCGTCCCTTTC |

After amplification of target region, site-specific amplicon sequencing described in Preparation Examples 5 above was performed. To measure the frequencies of indels in the target regions, the Cas-Analyzer algorithm (http://www.rgenome.net/cas-analyzer/#!) was used. The indel frequency result is shown in FIG. 25i.

Specifically, indels were randomly generated near the sgRNAs targeting sites, and both Trp 53 and Pten showed high indel frequencies over 80%. More specifically, indels of Trp53 were randomly generated in range of 69402693 to 69402702 of chromosome 11, and indels of Pten were randomly generated in range of 32874403 to 32874412 of chromosome 19 (reference mouse genome: UCSC mouse standard genome).

The Table 7 below is showing the representative amplicon sequencing results of Trp53 and Pten which are sequences more than 1% of total reads. The read frequency of the Table 7 refers to the each read ratio having notated sequences to total reads.

The tumor tissues were stained by H&E staining method, and the result is shown in FIG. 25*f*. The immunostaining results of glioma markers are shown in FIG. 25*h*. From the staining results, high-grade glioma having characteristics such as necrosis, microvascular proliferation, and mitosis

TABLE 71

| SEQ ID NO: | Nucleotide sequence | Read frequency (%) |
|---|---|---|
| | Trp53 | |
| 38 | TGTGTCTTCCCCCAGGCCGGCTCTGAGTATACCACCATCCACTACAA GTACATGTGTAATAGCTCCTGCACTTGGGGGGCATGAACCGCCGACC TATCCTTA | 36.3 |
| 39 | TGTGTCTTCCCCCAGGCCGGCTCTGAGTATACCACCATCCACTACAA GTACATGTGTAATAGCTCCTGTGGGGGGCATGAACCGCCGACCTATC CTTA | 34.7 |
| 40 | TGTGTCTTCCCCCAGGCCGGCTCTGAGTATACCACCATCCACTACAA GTACATGTGTAATAGCTCCTGCAATGGGGGGCATGAACCGCCGACCT ATCCTTA | 8.0 |
| | Pten | |
| 41 | AGACCATAACCCACCACAGCTAGAACTTATCAAACCCTTCTTGAAGA TCTTGACCAATGGCTAAGTGAAGATGACAATCATGTTGCAGCAATTC ACTGTAAAGCTGGAAA | 38.9 |
| 42 | AGACCATAACCCACCACAGCTAGAACTTATCAAACCCTCTGAAGATC TTGACCAATGGCTAAGTGAAGATGACAATCATGTTGCAGCAATTCAC TGTAAAGCTGGAAA | 36.6 |
| 43 | AGACCATAACCCACCACAGCTAGAACTTATCAAACCCTTCGTGAAG ATCTTGACCAATGGCTAAGTGAAGATGACAATCATGTTGCAGCAATT CACTGTAAAGCTGGAAA | 3.3 |

For the identification of EGFRviii expression in tumors, RNA was extracted from tumor and untreated brain tissue using RNeasy Mini Kit (Qiagen). Then, cDNA was generated from the extracted RNA using SuperScript II (Invitrogen). To amplify EGFRviii from the cDNA, the present inventors designed primers annealing to human EGFR exons 1 and 8. The sequences of the primers are as follows: forward, 5'-CCCAGGCACTTGATGATACTC-3' (SIQ. ID NO. 36) and reverse, 5'-CTTGCTTTGGGTGGAGAGTT-3' (SEQ ID NO: 37). The PCR conditions were as follows: 98° C. for 2 min; 35 times (98° C. for 10 s, 60° C. for 15 s, 68° C. for 30 s); hold at 4° C. Then, the amplicon was analysed by electrophoresis on 2% agarose gel. Actb was used as control. The electrophoresis result is shown in FIG. 25*j*. FIG. 25*j* is showing that EGFRviii was expressed only in tumors.

A gross mass of tumor was identified 16 weeks after electroporation. The MRI image is represented in FIG. 25*g*.

Specifically, MRI conditions are as follows. The mice were initially anaesthetized by inhalation of 5% isoflurane in an air/O2 mixture, and then placed in a cradle for MRI scans, with a respiratory mask connected to 1.5% isoflurane in an air/O2 mixture. MRI experiments were performed on an a 3T MRS 3000 scanner (MR Solutions) with a birdcage mouse head coil.

T1-weighted and T2-weighted images were respectively acquired with spin echo (SE) and fast spin echo (FSE) sequences for investigation of anatomical and pathological conditions. Scan parameters were as follows: time to repeat/echo time=550/11 ms (SE) and 3,000/68 ms (FSE), field of view=22×22 mm2, matrix size=256×256 (SE) and 256×248 (FSE), slice thickness=1 mm, number of slices=19, and scan time=9 min 23 s (SE) and 9 min 18 s (FSE).

were identified (FIG. 20 and FIG. 25*h*). The tumors had immunoreactivity to GFAP, Nestin, Olig2, and PDGFRα and showed characteristics of human glioma and high proliferation ability was observed.

Through, as somatic cancer driving mutants, for example, Trp53, Pten, and EGFR mutations have abilities to develop malignant glioma from NSCs in SVZ.

5-6. Similarities with Human Glioma (1) Over Time Analysis of Glioma Development To examine the time and spatial relationships between the occurrence of mutations in SVZs and the formation of glioma, the present inventors analysed the progress of glioma development over time.

Specifically, the present inventors obtained serial sections of mouse brain tissue from the olfactory bulb to caudal cortex, 2 days, 8 weeks and 13 to 15 weeks after electroporation. Then, tdTomato-positive cell migration was traced. It is discovered that tdTomato-positive cells migrated from the SVZ to the dorsolateral-caudal cortex and the olfactory bulb (FIG. 20).

In geome-edited mice (n=18), cells harboring driver mutations that migrated to the olfactory bulb properly differentiated to mature neurons and did not lead to glioma development, whereas cells that migrated to the dorsolateral-caudal cortex did (FIG. 20).

The tdTomato-positive cells proliferated throughout serial sections from p64, Pten and Egfr mutated mice. In particular, tdTomato-positive cells increased markedly in number over time in the distant cortical region away from the mutation arising SVZ (−2.5 and −3.5 mm from bregma) (FIG. 21).

Furthermore, the present inventors also noted that 67% of the gliomas developed in a distant region away from the mutation arising SVZ (FIG. 22) by measuring the location of glioma in serial sections or MRI images. In the mice having glioma in cortex (n=12), immunostaining result of H&E staining and nestin, S100β, and DAPI showed normal cyto-architecture similar to the tumor-free SVZs from GBM patients (FIG. 20).

(2) Identification of Cell Line Developing Glioma

To examine whether cells from NSCs develop glioma, abnormal proliferations were analyzed for neuron, astrocyte, oligodendrocyte, and oligodendrocyteprecursor cells.

Specifically, before the formation of a visible tumor, tdTomato-positive cells in cortex region were immunos-tained as follows: NeuN for neuron, GFPA for astrocyte, MBP for oligodendrocyte, and Olig2 and PDGFRa for oligodendrocyteprecursor cells.

Majority of tdTomato-positive cells were co-expressing Olig2 or PDGFRa (FIG. 23).

Figure 24:
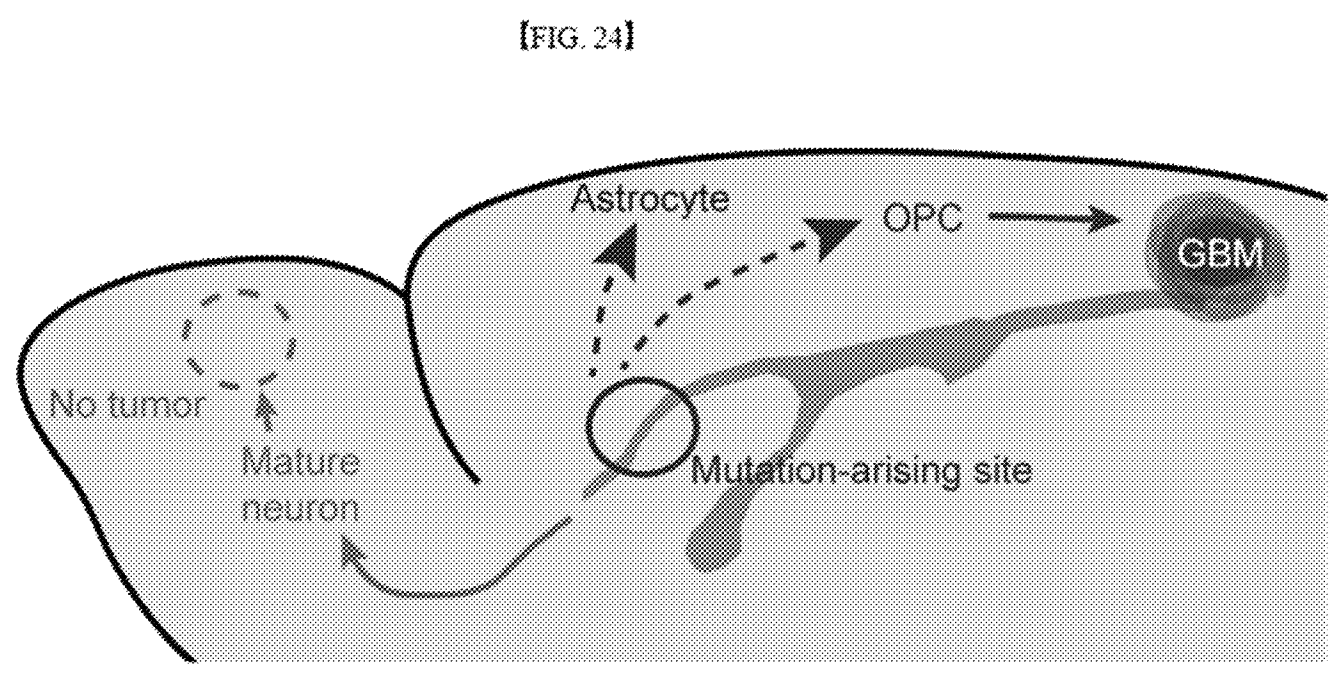

Accordingly, it is confirmed that NSCs having driver mutations migrate from SVZ and induce malignant glioma by abnormal proliferation of oligodendrocyteprecursor cells (FIG. 24).

---

The invention claimed is:

1. A transgenic mouse comprising, knock-out mutations of p53 and Pten genes in nerve stem cells of subventricular zone (SVZ), and an activating mutation of epidermal growth factor receptor (EGFR) gene in nerve stem cells of SVZ, wherein a glioblastoma occurs in the dorsolateral-caudal cortex region, wherein the glioblastoma develops from nerve stem cells that are positive for Glial fibrillary acidic protein (GFAP), wherein the GFAP positive nerve stem cells have normal cytoarchitecture.

2. The transgenic mouse of claim 1, wherein the glioblastoma is a high-grade glioblastoma having characteristics of necrosis, microvascular proliferation and mitosis, and has an immune response to GFAP, Nestin, Olig2, and PDGFRα.

3. The transgenic mouse of claim 1, wherein the glioblastoma is IDH-wild type.

4. The transgenic mouse of claim 1, wherein the mouse maintains the knockout mutations of p53 and Pten genes specific to nerve stem cells in SVZ even after glioblastoma occurrence.

5. The transgenic mouse of claim 1, wherein the p53 gene comprises at least one nucleotide sequence of SEQ ID Nos: 38 to 40, and the Pten gene comprises at least g nucleotide sequence of SEQ ID Nos: 41 to 43.

* * * * *

SEQUENCE LISTING

```
Sequence total quantity: 43
SEQ ID NO: 1              moltype = DNA  length = 17
FEATURE                  Location/Qualifiers
misc_feature             1..17
                         note = TERT_forward
source                   1..17
                         mol_type = other DNA
                         organism = synthetic construct
SEQUENCE: 1
gcacctcgcg gtagtgg                                               17

SEQ ID NO: 2              moltype = DNA  length = 18
FEATURE                  Location/Qualifiers
misc_feature             1..18
                         note = TERT_reverse
source                   1..18
                         mol_type = other DNA
                         organism = synthetic construct
SEQUENCE: 2
gtcctgcccc ttcacctt                                              18

SEQ ID NO: 3              moltype = DNA  length = 20
FEATURE                  Location/Qualifiers
misc_feature             1..20
                         note = EGFR_forward
source                   1..20
                         mol_type = other DNA
                         organism = synthetic construct
SEQUENCE: 3
ctacaacccc accacgtacc                                            20

SEQ ID NO: 4              moltype = DNA  length = 20
FEATURE                  Location/Qualifiers
misc_feature             1..20
                         note = EGFR_reverse
source                   1..20
                         mol_type = other DNA
                         organism = synthetic construct
SEQUENCE: 4
ccacccaaag actctccaag                                            20

SEQ ID NO: 5              moltype = DNA  length = 20
FEATURE                  Location/Qualifiers
misc_feature             1..20
                         note = PTEN_forward
source                   1..20
                         mol_type = other DNA
                         organism = synthetic construct
SEQUENCE: 5
accaggacca gaggaaacct                                            20

SEQ ID NO: 6              moltype = DNA  length = 20
FEATURE                  Location/Qualifiers
misc_feature             1..20
                         note = PTEN_reverse
source                   1..20
                         mol_type = other DNA
                         organism = synthetic construct
SEQUENCE: 6
agtcaacaac ccccacaaaa                                            20

SEQ ID NO: 7              moltype = DNA  length = 20
FEATURE                  Location/Qualifiers
misc_feature             1..20
```

```
                          note = TP53_forward
source                    1..20
                          mol_type = other DNA
                          organism = synthetic construct
SEQUENCE: 7
gggccagacc taagagcaat                                                     20

SEQ ID NO: 8              moltype = DNA  length = 20
FEATURE                   Location/Qualifiers
misc_feature              1..20
                          note = TP53_reverse
source                    1..20
                          mol_type = other DNA
                          organism = synthetic construct
SEQUENCE: 8
ctttgaggtg cgtgtttgtg                                                     20

SEQ ID NO: 9              moltype = DNA  length = 21
FEATURE                   Location/Qualifiers
misc_feature              1..21
                          note = Rb1_forward
source                    1..21
                          mol_type = other DNA
                          organism = synthetic construct
SEQUENCE: 9
gcacaaaaag aaacacccaa a                                                   21

SEQ ID NO: 10             moltype = DNA  length = 20
FEATURE                   Location/Qualifiers
misc_feature              1..20
                          note = Rb1_reverse
source                    1..20
                          mol_type = other DNA
                          organism = synthetic construct
SEQUENCE: 10
gtccaaagga atgccaattt                                                     20

SEQ ID NO: 11             moltype = AA  length = 1136
FEATURE                   Location/Qualifiers
REGION                    1..1136
                          note = human EGFR A289V protein
source                    1..1136
                          mol_type = protein
                          organism = synthetic construct
SEQUENCE: 11
MRPSGTAGAA LLALLAALCP ASRALEEKKV CQGTSNKLTQ LGTFEDHFLS LQRMFNNCEV  60
VLGNLEITYV QRNYDLSFLK TIQEVAGYVL IALNTVERIP LENLQIIRGN MYYENSYALA  120
VLSNYDANKT GLKELPMRNL QEILHGAVRF SNNPALCNVE SIQWRDIVSS DFLSNMSMDF  180
QNHLGSCQKC DPSCPNGSCW GAGEENCQKL TKIICAQQCS GRCRGKSPSD CCHNQCAAGC  240
TGPRESDCLV CRKFRDEATC KDTCPPLMLY NPTTYQMDVN PEGKYSFGVT CVKKCPRNYV  300
VTDHGSCVRA CGADSYEMEE DGVRKCKKCE GPCRKVCNGI GIGEFKDSLS INATNIKHFK  360
NCTSISGDLH ILPVAFRGDS FTHTPPLDPQ ELDILKTVKE ITGFLLIQAW PENRTDLHAF  420
ENLEIIRGRT KQHGQFSLAV VSLNITSLGL RSLKEISDGD VIISGNKNLC YANTINWKKL  480
FGTSGQKTKI ISNRGENSCK ATGQVCHALC SPEGCWGPEP RDCVSCRNVS RGRECVDKCN  540
LLEGEPREFV ENSECIQCHP ECLPQAMNIT CTGRGPDNCI QCAHYIDGPH CVKTCPAGVM  600
GENNTLVWKY ADAGHVCHLC HPNCTYGCTG PGLEGCPTNG PKIPSIATGM VGALLLLLVV  660
ALGIGLFMRR RHIVRKRTLR RLLQERELVE PLTPSGEAPN QALLRILKET EFKKIKVLGS  720
GAFGTVYKGL WIPEGEKVKI PVAIKELREA TSPKANKEIL DEAYVMASVD NPHVCRLLGI  780
CLTSTVQLIT QLMPFGCLLD YVREHKDNIG SQYLLNWCVQ IAKGMNYLED RRLVHRDLAA  840
RNVLVKTPQH VKITDFGLAK LLGAEEKEYH AEGGKVPIKW MALESILHRI YTHQSDVWSY  900
GVTVWELMTF GSKPYDGIPA SEISSILEKG ERLPQPPICT IDVYMIMVKC WMIDADSRPK  960
FRELIIEFSK MARDPQRYLV IQGDERMHLP SPTDSNFYRA LMDEEDMDDV VDADEYLIPQ  1020
QGFFSSPSTS RTPLLSSLSA TSNNSTVACI DRNGLQSCPI KEDSFLQRYS SDPTGALTED  1080
SIDDTFLVPV PGEWLVWKQSC SSTSSTHSAA ASLQCPSQVL PPASPEGETV ADLQTQ      1136

SEQ ID NO: 12             moltype = DNA  length = 3411
FEATURE                   Location/Qualifiers
misc_feature             1..3411
                          note = human EGFR A289V cDNA
source                    1..3411
                          mol_type = other DNA
                          organism = synthetic construct
SEQUENCE: 12
atgcgaccct ccgggacggc cggggcagcg ctcctggcgc tgctggctgc gctctgcccg  60
gcgagtcggg ctctggagga aaagaaagtt tgccaaggca cgagtaacaa gctcacgcag  120
ttgggcactt ttgaagatca tttttctcagc ctccagagga tgttcaataa ctgtgaggtg  180
gtccttggga atttggaaat tacctatgtg cagaggaatt atgatctttc cttcttaaag  240
accatccagg aggtggctgg ttatgtcctc attgccctca acacagtgga gcgaattcct  300
ttggaaaacc tgcagatcat cagaggaaat atgtactacg aaaattccta tgccttagca  360
```

```
gtcttatcta actatgatgc aaataaaacc ggactgaagg agctgcccat gagaaattta   420
caggaaatcc tgcatggcgc cgtgcggttc agcaacaacc ctgccctgtg caacgtggag   480
agcatccagt ggcgggacat agtcagcagt gactttctca gcaacatgtc gatggacttc   540
cagaaccacc tgggcagctg ccaaaagtgt gatccaagct gtcccaatgg gagctgctgg   600
ggtgcaggag aggagaactg ccagaaactg accaaaatca tctgtgccca gcagtgctcc   660
gggcgctgcc gtggcaagtc ccccagtgac tgctgccaca accagtgtgc tgcaggctgc   720
acaggccccc gggagagcga ctgcctggtc tgccgcaaat ccgagacga agccacgtgc   780
aaggacacct gccccccact catgctctac aaccccacca cgtaccagat ggatgtgaac   840
cccgagggca aatacagctt tggtgtcacc tgcgtgaaga agtgtccccg taattatgtg   900
gtgacagatc acggctcgtg cgtcccgagcc tgtgggccg acagctatga gatggaggaa   960
gacggcgtcc gcaagtgtaa gaagtgcgaa gggccttgcc gcaaagtgtg taacggaata  1020
ggtattggtg aatttaaaga ctcactctcc ataaatgcta cgaatattaa acacttcaaa  1080
aactgcacct ccatcagtgg cgatctccac atcctgccgg tggcatttag gggtgactcc  1140
ttcacacata ctcctcctct ggatccacag gaactggata ttctgaaaac cgtaaaggaa  1200
atcacagggt ttttgctgat tcaggcttgg cctgaaaaca ggacggacct ccatgccttt  1260
gagaacctag aaatcatacg cggcaggacc aagcaacatg gtcagttttc tcttgcagtc  1320
gtcagcctga acataaatc cttgggatta cgctccctca aggagataag tgatggagat  1380
gtgataattt caggaaacaa aaatttgtgc tatgcaaata caataaactg aaaaaactg  1440
tttgggacct ccggtcagaa aaccaaaatt ataagcaaca gaggtgaaaa cagctgcaag  1500
gccacaggcc aggtctgcca tgccttgtgc tcccccgagg gctgctgggg cccggagccc  1560
agggactgcg tctcttgccg gaatgtcagc cgaggcaggg aatgcgtgga caagtgcaac  1620
cttctggagg gtgagccaag ggagtttgtg gagaactg atgccaccca  1680
gagtgcctgc ctcaggccat gaacatcacc tgcacaggac ggggaccaga caactgtatc  1740
cagtgtgccc actacattga cggccccac tgcgtcaaga cctgcccggc aggagtcatg  1800
ggagaaaaca cacccctggt ctggaagtac gcagacgccg gccatgtgtg ccacctgtgc  1860
catccaaact gcacctacgg atgcactggg ccaggtcttg aaggctgtcc aacgaatggg  1920
cctaagatcc cgtccatcgc cactgggatg gtggggggccc tcctcttgct gctggtggtg  1980
gccctgggga tcggcctctt catgcgaagg cgccacatcg ttcggaagcg cacgctgcgg  2040
aggctgctgc aggagaggga gcttgtggag cctcttacac ccagtggaga agctcccaac  2100
caagctctct tgaggatctt gaaggaaact gaattcaaaa agatcaaagt ggcgggcatc  2160
ggtgcgttcg gcacggtgta taagggactc tggatcccag aaggtgagaa agttaaaatt  2220
cccgtcgcta tcaaggaatt aagagaagca acatctccga aagccaacaa ggaaatcctc  2280
gatgaagcct acgtgatggc cagcgtggac aacccccacg tgtgccgcct gctgggcatc  2340
tgcctcacct ccaccgtgca gctcatcacg cagctcatgc ccttcggctg cctcctggac  2400
tatgtccggg aacacaaaga caatattggc tcccagtact gctcaactg gtgtgtgcag  2460
atcgcaaagg gcatgaacta cttggaggac cgtcgcttgg tgcaccgcga cctggcagcc  2520
aggaacgtac tggtgaaaac accgcagcat gtcaagatca cagatttggg ctgccaaaa  2580
ctgctgggtg cggaagagaa agaataccat gcagaaggag gcaaagtgcc tatcaagtgg  2640
atggcattgg aatcaatttt acacagaatc tatacccacc agagtgatgt ctggagctac  2700
ggggtgactg tttgggagtt gatgacctt ggatccaagc catatgacgg aatccctgcc  2760
agcgagatct cctccatcct ggagaaagga gaacgcctcc ctcagccacc catatgtacc  2820
atcgatgtct acatgatcat ggtcaagtgc tggatgatag acgcagatag tcgcccaaag  2880
ttccgtgagt tgatcatcga attctccaaa atggcccgag accccagcg ctaccttgtc  2940
attcagggg atgaaagaat gcatttgcca agtcctacag actccaactt ctaccgtgcc  3000
ctgatggatg aagaagacat ggacgacgtg gtggatccg acgagtacct catcccacag  3060
cagggcttct tcagcagccc ctccacgtca cggactcccc tcctgagctc tctgagtgca  3120
accagcaaca attccaccgt ggcttgcatt gatagaaatg ggctgcaaag tcgtcccatc  3180
aaggaagaca gcttcttgca gcgatacagc tcagacccca caggcgcctt gactgaggac  3240
agcatagacg acaccttcct cccagtgcct ggtgagtggg ttgtctggaa acagtcctgc  3300
tcctcaacct cctcgaccca ctcagcagca gccagtctcc agtgtccaag ccaggtgctc  3360
cctccagcat ctccagaggg ggaaacagtg cagatttgca gacacagtg a              3411
```

```
SEQ ID NO: 13          moltype = AA   length = 341
FEATURE                Location/Qualifiers
REGION                 1..341
                       note = human TP53 C176Y protein
source                 1..341
                       mol_type = protein
                       organism = synthetic construct
SEQUENCE: 13
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK  120
SVTCTYSPAL NKMFCQLAKT CPVQLWVDST PPPGTRVRAM AIYKQSQHMT EVVRRYPHHE  180
RCSDSDGLAP PQHLIRVEGN LRVEYLDDRN TFRHSVVVPY EPPEVGSDCT TIHYNYMCNS  240
SCMGGMNRRP ILTIITLEDS SGNLLGRNSF EVRVCACPGR DRRTEEENLR KKGEPHHELP  300
PGSTKRALPN NTSSSPQPKK KPLDGEYFTL QDQTSFQKEN C                       341
```

```
SEQ ID NO: 14          moltype = DNA   length = 1026
FEATURE                Location/Qualifiers
misc_feature           1..1026
                       note = human TP53 C176Y cDNA
source                 1..1026
                       mol_type = other DNA
                       organism = synthetic construct
SEQUENCE: 14
atggaggagc cgcagtcaga tcctagcgtc gagccccctc tgagtcagga aacattttca   60
gacctatgga aactacttcc tgaaacaaac gttctgtccc ccttgccgtc ccaagcaatg  120
gatgatttga tgctgtcccc ggacgatatt gaacaatggt tcactgaaga cccaggtcca  180
gatgaagctc ccagaatgcc agaggctgct cccccgtgg ccctgcacc agcagctcct  240
```

-continued

```
acaccggcgg cccctgcacc agcccctcc tggcccctgt catcttctgt cccttcccag   300
aaaacctacc agggcagcta cggtttccgt ctgggcttct tgcattctgg gacagccaag   360
tctgtgactt gcacgtactc ccctgccctc aacaagatgt tttgccaact ggccaagacc   420
tgccctgtgc agctgtgggt tgattccaca cccccgcccg gcaccgcgt ccgcgccatg    480
gccatctaca agcagtcaca gcacatgacg gaggttgtga ggcgctaccc ccaccatgag   540
cgctgctcag atagcgatgg tctggcccct cctcagcatc ttatccgagt ggaaggaaat   600
ttgcgtgtgg agtatttgga tgacagaaac actttttcgac atagtgtggt ggtgccctat   660
gagccgcctg aggttggctc tgactgtacc accatccact acaactacat gtgtaacagt   720
tcctgcatgg gcggcatgaa ccggaggccc atcctcacca tcatcacact ggaagactcc   780
agtggtaatc tactgggacg gaacagcttt gaggtgcgtg tttgtgcctg tcctgggaga   840
gaccggcgca cagaggaaga gaatctccgc aagaaagggg agcctcacca cgagctgccc   900
ccagggagca ctaagcgagc actgcccaac aacaccagct cctctcccca gccaaagaag   960
aaaccactgg atggagaata tttcacccct caggaccaga ccagctttca aaagaaaat   1020
tgttaa                                                            1026
```

SEQ ID NO: 15                moltype = AA   length = 341
FEATURE                      Location/Qualifiers
REGION                       1..341
                             note = human TP53 E285K protein
source                       1..341
                             mol_type = protein
                             organism = synthetic construct
SEQUENCE: 15
```
MEEPQSDPSV EPPLSQETFS DLWKLLPENN VLSPLPSQAM DDLMLSPDDI EQWFTEDPGP   60
DEAPRMPEAA PPVAPAPAAP TPAAPAPAPS WPLSSSVPSQ KTYQGSYGFR LGFLHSGTAK   120
SVTCTYSPAL NKMFCQLAKT CPVQLWVDST PPPGTRVRAM AIYKQSQHMT EVVRRCPHHE   180
RCSDSDGLAP PQHLIRVEGN LRVEYLDDRN TFRHSVVVPY EPPEVGSDCT TIHYNYMCNS   240
SCMGGMNRRP ILTIITLEDS SGNLLGRNSF EVRVCACPGR DRRTKEENLR KKGEPHHELP   300
PGSTKRALPN NTSSSPQPKK KPLDGEYFTL QDQTSFQKEN C                      341
```

SEQ ID NO: 16                moltype = DNA   length = 1026
FEATURE                      Location/Qualifiers
misc_feature                 1..1026
                             note = human TP53 E285K cDNA
source                       1..1026
                             mol_type = other DNA
                             organism = synthetic construct
SEQUENCE: 16
```
atggaggagc cgcagtcaga tcctagcgtc gagcccctc tgagtcagga aacattttca   60
gacctatgga aactacttcc tgaaaacaac gttctgtccc ccttgccgtc ccaagcaatg   120
gatgatttga tgctgtcccc ggacgatatt gaacaatggt tcactgaaga cccaggtcca   180
gatgaagctc ccagaatgcc agaggctgct ccccccgtgg cccctgcacc agcagctcct   240
acaccggcgg cccctgcacc agcccctcc tggcccctgt catcttctgt cccttcccag   300
aaaacctacc agggcagcta cggtttccgt ctgggcttct tgcattctgg gacagccaag   360
tctgtgactt gcacgtactc ccctgccctc aacaagatgt tttgccaact ggccaagacc   420
tgccctgtgc agctgtgggt tgattccaca cccccgcccg gcaccgcgt ccgcgccatg    480
gccatctaca agcagtcaca gcacatgacg gaggttgtga ggcgctaccc ccaccatgag   540
cgctgctcag atagcgatgg tctggcccct cctcagcatc ttatccgagt ggaaggaaat   600
ttgcgtgtgg agtatttgga tgacagaaac actttttcgac atagtgtggt ggtgccctat   660
gagccgcctg aggttggctc tgactgtacc accatccact acaactacat gtgtaacagt   720
tcctgcatgg gcggcatgaa ccggaggccc atcctcacca tcatcacact ggaagactcc   780
agtggtaatc tactgggacg gaacagcttt gaggtgcgtg tttgtgcctg tcctgggaga   840
gaccggcgca caaaggaaga gaatctccgc aagaaagggg agcctcacca cgagctgccc   900
ccagggagca ctaagcgagc actgcccaac aacaccagct cctctcccca gccaaagaag   960
aaaccactgg atggagaata tttcacccct caggaccaga ccagctttca aaagaaaat   1020
tgttaa                                                            1026
```

SEQ ID NO: 17                moltype = AA   length = 321
FEATURE                      Location/Qualifiers
REGION                       1..321
                             note = human PTEN V317fs6 protein
source                       1..321
                             mol_type = protein
                             organism = synthetic construct
SEQUENCE: 17
```
MTAIIKEIVS RNKRRYQEDG FDLDLTYIYP NIIAMGFPAE RLEGVYRNNI DDVVRFLDSK   60
HKNHYKIYNL CAERHYDTAK FNCRVAQYPF EDHNPPQLEL IKPFCEDLDQ WLSEDDNHVA   120
AIHCKAGKGR TGVMICAYLL HRGKFLKAQE ALDFYGEAVT RDKKGVTIPS QRRYVYYYSY   180
LLKNHLDYRP VALLFHKMMF ETIPMFSGGT CNPQFVVCQL KVKIYSSNSG PTRREDKFMY   240
FEFPQPLPVC GDIKVEFFHK QNKMLKKDKM FHFWVNTFFI PGPEETSEKV ENGSLCDQEI   300
DSICSIERAD NDKEYLDFNK K                                            321
```

SEQ ID NO: 18                moltype = DNA   length = 1207
FEATURE                      Location/Qualifiers
misc_feature                 1..1207
                             note = human PTEN V317fs6 DNA
source                       1..1207
                             mol_type = other DNA
                             organism = synthetic construct

```
SEQUENCE: 18
atgacagcca tcatcaaaga gatcgttagc agaaacaaaa ggagatatca agaggatgga   60
ttcgacttag acttgaccta tatttatcca aacattattg ctatgggatt tcctgcagaa  120
agacttgaag gcgtatacag gaacaatatt gatgatgtag taaggttttt ggattcaaag  180
cataaaaacc attacaagat atacaatctt tgtgctgaaa gacattatga caccgccaaa  240
tttaattgca gagttgcaca atatcctttt gaagaccata acccaccaca gctagaactt  300
atcaaaccct tttgtgaaga tcttgaccaa tggctaagtg aagatgacaa tcatgttgca  360
gcaattcact gtaaagctgg aaagggacga actggtgtaa tgatatgtgc atatttatta  420
catcggggca aatttttaaa ggcacaagag gccctagatt tctatgggga agtaaggacc  480
agagacaaaa agggagtaac tattcccagt cagaggcgct atgtgtatta ttatagctac  540
ctgttaaaga atcatctgga ttatagacca gtggcactgt tgtttcacaa gatgatgttt  600
gaaactattc caatgttcag tggcggaact tgcaatcctc agtttgtggt ctgccagcta  660
aaggtgaaga tatattcctc caattcagga cccacacgac gggaagacaa gttcatgtac  720
tttgagttcc ctcagccgtt acctgtgtgt ggtgatatca aagtagagtt cttccacaaa  780
cagaacaaga tgctaaaaaa ggacaaaatg tttcactttt gggtaaatac attcttcata  840
ccaggaccag aggaaacctc agaaaaagta gaaaatggaa gtctatgtga tcaagaaatc  900
gatagcattt gcagtataga gcgtgcagat aatgacaagg aatatctaga ctttaacaaa  960
aaatgatctt gacaaagcaa ataaagacaa agccaaccga tactttctc caaattttaa  1020
ggtgaagctg tacttcacaa aaacagtaga ggagccgtca aatccagagg ctagcagttc  1080
aacttctgta acaccagatg ttagtgacaa tgaacctgat cattatagat attctgacac  1140
cactgactct gatccagaga atgaaccttt tgatgaagat cagcatacac aaattacaaa  1200
agtctga                                                           1207

SEQ ID NO: 19          moltype = AA  length = 318
FEATURE                Location/Qualifiers
REGION                 1..318
                       note = human PTEN V317fs3 protein
source                 1..318
                       mol_type = protein
                       organism = synthetic construct
SEQUENCE: 19
MTAIIKEIVS RNKRRYQEDG FDLDLTYIYP NIIAMGFPAE RLEGVYRNNI DDVVRFLDSK   60
HKNHYKIYNL CAERHYDTAK FNCRVAQYPF EDHNPPQLEL IKPFCEDLDQ WLSEDDNHVA  120
AIHCKAGKGR TGVMICAYLL HRGKFLKAQE ALDFYGEVRT RDKKGVTIPS QRRYVYYYSY  180
LLKNHLDYRP VALLFHKMMF ETIPMFSGGT CNPQFVVCQL KVKIYSSNSG PTRREDKFMY  240
FEFPQPLPVC GDIKVEFFHK QNKMLKKDKM FHFWVNTFFI PGPEETSEKV ENGSLCDQEI  300
DSICSIERAD NDKEYLVL                                               318

SEQ ID NO: 20          moltype = DNA  length = 1208
FEATURE                Location/Qualifiers
misc_feature           1..1208
                       note = human PTEN V317fs3 DNA
source                 1..1208
                       mol_type = other DNA
                       organism = synthetic construct
SEQUENCE: 20
atgacagcca tcatcaaaga gatcgttagc agaaacaaaa ggagatatca agaggatgga   60
ttcgacttag acttgaccta tatttatcca aacattattg ctatgggatt tcctgcagaa  120
agacttgaag gcgtatacag gaacaatatt gatgatgtag taaggttttt ggattcaaag  180
cataaaaacc attacaagat atacaatctt tgtgctgaaa gacattatga caccgccaaa  240
tttaattgca gagttgcaca atatcctttt gaagaccata acccaccaca gctagaactt  300
atcaaaccct tttgtgaaga tcttgaccaa tggctaagtg aagatgacaa tcatgttgca  360
gcaattcact gtaaagctgg aaagggacga actggtgtaa tgatatgtgc atatttatta  420
catcggggca aatttttaaa ggcacaagag gccctagatt tctatgggga agtaaggacc  480
agagacaaaa agggagtaac tattcccagt cagaggcgct atgtgtatta ttatagctac  540
ctgttaaaga atcatctgga ttatagacca gtggcactgt tgtttcacaa gatgatgttt  600
gaaactattc caatgttcag tggcggaact tgcaatcctc agtttgtggt ctgccagcta  660
aaggtgaaga tatattcctc caattcagga cccacacgac gggaagacaa gttcatgtac  720
tttgagttcc ctcagccgtt acctgtgtgt ggtgatatca aagtagagtt cttccacaaa  780
cagaacaaga tgctaaaaaa ggacaaaatg tttcactttt gggtaaatac attcttcata  840
ccaggaccag aggaaacctc agaaaaagta gaaaatggaa gtctatgtga tcaagaaatc  900
gatagcattt gcagtataga gcgtgcagat aatgacaagg aatatctagt actttaacaa  960
aaaatgatct tgacaaagca aataaagaca aagccaaccg atactttct ccaaatttta  1020
aggtgaagct gtacttcaca aaaacagtag aggagccgtc aaatccagag gctagcagtt  1080
caacttctgt aacaccagat gttagtgaca atgaacctga tcattataga tattctgaca  1140
ccactgactc tgatccagag aatgaacctt tgatgaaga tcagcataca caaattacaa  1200
aagtctga                                                          1208

SEQ ID NO: 21          moltype = AA  length = 212
FEATURE                Location/Qualifiers
REGION                 1..212
                       note = human Rb K202fs protein
source                 1..212
                       mol_type = protein
                       organism = synthetic construct
SEQUENCE: 21
MPPKTPRKTA ATAAAAAEP PAPPPPPPPE EDPEQDSGPE DLPLVRLEFE ETEEPDFTAL   60
CQKLKIPDHV RERAWLTWEK VSSVDGVLGG YIQKKKELWG ICIFIAAVDL DEMSFTFTEL  120
QKNIEISVHK FFNLLKEIDT STKVDNAMSR LLKKYDVLFA LFSKLERTCE LIYLTQPSSS  180
```

-continued

```
ISTEINSALV LKVSWITFLL AKGKYYKWKM IW                             212

SEQ ID NO: 22           moltype = DNA   length = 2786
FEATURE                 Location/Qualifiers
misc_feature            1..2786
                        note = human Rb K202fs DNA
source                  1..2786
                        mol_type = other DNA
                        organism = synthetic construct
SEQUENCE: 22
atgccgccca aaacccccg aaaaacggcc gccaccgccg ccgctgccgc cgcggaaccc   60
ccggcaccgc cgccgccgcc ccctcctgag gaggacccag agcaggacag cggcccggag  120
gacctgcctc tcgtcaggct tgagtttgaa gaaacagaag aacctgattt tactgcatta  180
tgtcagaaat taaagatacc agatcatgtc agagagagag cttggttaac ttgggagaaa  240
gtttcatctg tggatggagt attgggaggt tatattcaaa agaaaaagga actgtgggga  300
atctgtatct ttattgcagc agttgaccta gatgagatgt cgttcacttt tactgagcta  360
cagaaaaaca tagaaatcag tgtccataaa ttctttaact tactaaaaga aattgatacc  420
agtaccaaag ttgataatgc tatgtcaaga ctgttgaaga agtatgatgt attgtttgca  480
ctcttcagca aattggaaag gacatgtgaa cttatatatt tgacacaacc cagcagttcg  540
atatctactg aaataaaattc tgcattggtg ctaaaagtttt cttggatcac atttttatta  600
gctaaaggga agtattacaa atggaagatg atctggtgat ttcatttcag ttaatgctat  660
gtgtccttga ctattttatt aaactctcac ctcccatgtt gctcaaagaa ccatataaaa  720
cagctgttat acccattaat ggttcacctc gaacacccag gcgaggtcag aacaggagtg  780
cacggatagc aaaacaacta gaaaatgata caagaattat tgaagttctc tgtaaagaac  840
atgaatgtaa tatagatgag gtgaaaaatg tttatttcaa aaatttttata cctttatga   900
attctcttgg acttgtaaca tctaatggac ttccagaggt tgaaaatctt tctaaacgat   960
acgaagaaat ttatcttaaa aataaagatc tagatgcaag attatttttg gatcatgata  1020
aaactcttca gactgattct atagacagtt ttgaaacaca gagaacacca cgaaaaagta  1080
accttgatga gagaggtgaat gtaattcctc cacacactcc agttaggact gttatgaaca  1140
ctatccaaca attaatgatg atttttaaatt cagcaagtga tcaaccttca gaaaatctga  1200
tttcctattt taacaactgc acagtgaatc caaaagaaag tatactgaaa agagtgaagg  1260
atataggata catctttaaa gagaaatttg ctaaagctgt gggacagggt tgtgtcgaaa  1320
ttggatcaca gcgatacaaa cttggagttc gcttgtatta ccgagtaatg gaatccatgc  1380
ttaaatcaga agaagaacga ttatccattc aaaattttag caaacttctg aatgacaaca  1440
tttttcatat gtctttattg gcgtgcgctc ttgaggttgt aatggccaca tatagcagaa  1500
gtacatctca gaatcttgat tctggaacag atttgtcttt cccatggatt ctgaatgtgc  1560
ttaatttaaa agcctttgat ttttacaaag tgatcgaaag ttttatcaaa gcagaaggca  1620
acttgacaag agaaatgata aaacatttag aacgatgtga acatcgaatc atggaatccc  1680
ttgcatggct ctcagattca ccttttattg atcttattaa acaatcaaag gaccgagaag  1740
gaccaactga tcaccttgaa tctgcttgtc ctcttaatct tcctctccag aataatcaca  1800
ctgcagcaga tatgtatctt tctcctgtaa gatctccaaa gaaaaaaggt tcaactacgc  1860
gtgtaaattc tactgcaaat gcagagacac aagcaacctc agccttccag acccagaagc  1920
cattgaaatc tacctctctt tcactgtttt ataaaaaagt gtatcggtca gcctatctcc  1980
ggctaaatac actttgtgaa cgccttctgt ctgagcaccc agaattagaa catatcatct  2040
ggaccctttt ccagcacacc ctgcagaatg agtatgaact catgagagac aggcatttgg  2100
accaaattat gatgtgttcc atgtatggca tatgcaaagt gaagaatata gacctaaat   2160
tcaaaatcat tgtaacagca tacaaggatc ttcctcactga tgttcaggag acattcaaac  2220
gtgtttttgat caaagaagag gagtatgatt ctattatagt attctataac tcggtcttca  2280
tgcagagact gaaaacaaat attttgcagt atgcttccac caggcccect accttgtcac  2340
caataacctca cattcctcga agcccttaca gtttcctag ttcacccta cggattcctg  2400
gagggaacat ctatatttca ccectgaaga gtccatataa aatttcagaa ggtctgccaa  2460
caccaacaaa aatgactcca agatcaagaa tcttagtatc aattggtgaa tcattcggga  2520
cttctgagaa gttccagaaa ataaatcaga tggtatgtaa cagcgaccgt gtgctcaaaa  2580
gaagtgctga aggaagcaac cctcctaaac cactgaaaaa actacgcttt gatattgaag  2640
gatcagatga agcagatgga agtaaacatc tcccaggaga gtccaaattt cagcagaaac  2700
tggcagaaat gacttctact cgaacacgaa tgcaaaagca gaaaatgaat gatagcatgg  2760
atacctcaaa caaggaagag aaatga                                       2786

SEQ ID NO: 23           moltype = DNA   length = 18
FEATURE                 Location/Qualifiers
misc_feature            1..18
                        note = EGFR_RTqPCR_Forward
source                  1..18
                        mol_type = other DNA
                        organism = synthetic construct
SEQUENCE: 23
cgtctcttgc cggaatgt                                                18

SEQ ID NO: 24           moltype = DNA   length = 25
FEATURE                 Location/Qualifiers
misc_feature            1..25
                        note = EGFR_RTqPCR_Reverse
source                  1..25
                        mol_type = other DNA
                        organism = synthetic construct
SEQUENCE: 24
ggattaaaga aataacctcc taccc                                        25

SEQ ID NO: 25           moltype = DNA   length = 19
```

-continued

```
FEATURE            Location/Qualifiers
misc_feature       1..19
                   note = RNAseP_RTqPCR_Forward
source             1..19
                   mol_type = other DNA
                   organism = synthetic construct
SEQUENCE: 25
gggagatgcg gaagaatgt                                         19

SEQ ID NO: 26       moltype = DNA  length = 19
FEATURE            Location/Qualifiers
misc_feature       1..19
                   note = RNAseP_RTqPCR_Reverse
source             1..19
                   mol_type = other DNA
                   organism = synthetic construct
SEQUENCE: 26
cctccagtca gccacagaa                                         19

SEQ ID NO: 27       moltype = DNA  length = 20
FEATURE            Location/Qualifiers
misc_feature       1..20
                   note = LDHA_RTqPCR_Forward
source             1..20
                   mol_type = other DNA
                   organism = synthetic construct
SEQUENCE: 27
actgtgaccc ttatccaggc                                        20

SEQ ID NO: 28       moltype = DNA  length = 23
FEATURE            Location/Qualifiers
misc_feature       1..23
                   note = LDHA_RTqPCR_Reverse
source             1..23
                   mol_type = other DNA
                   organism = synthetic construct
SEQUENCE: 28
cttcccttaa ctagctctca gga                                    23

SEQ ID NO: 29       moltype = DNA  length = 21
FEATURE            Location/Qualifiers
misc_feature       1..21
                   note = sgRNA_p53
source             1..21
                   mol_type = other DNA
                   organism = synthetic construct
SEQUENCE: 29
ggtgtaatag ctcctgcatg g                                      21

SEQ ID NO: 30       moltype = DNA  length = 22
FEATURE            Location/Qualifiers
misc_feature       1..22
                   note = sgRNA_Pten
source             1..22
                   mol_type = other DNA
                   organism = synthetic construct
SEQUENCE: 30
ggttggtcaa gatcttcaca ga                                     22

SEQ ID NO: 31       moltype = DNA  length = 22
FEATURE            Location/Qualifiers
misc_feature       1..22
                   note = sgRNA_lacz
source             1..22
                   mol_type = other DNA
                   organism = synthetic construct
SEQUENCE: 31
ggtgcgaata cgcccacgcg at                                     22

SEQ ID NO: 32       moltype = DNA  length = 20
FEATURE            Location/Qualifiers
misc_feature       1..20
                   note = Mouse_Trp53_forward
source             1..20
                   mol_type = other DNA
                   organism = synthetic construct
SEQUENCE: 32
aggtagggag cgacttcacc                                        20
```

```
SEQ ID NO: 33          moltype = DNA   length = 20
FEATURE                Location/Qualifiers
misc_feature           1..20
                       note = Mouse_Trp53_reverse
source                 1..20
                       mol_type = other DNA
                       organism = synthetic construct
SEQUENCE: 33
taaggatagg tcggcggttc                                         20

SEQ ID NO: 34          moltype = DNA   length = 20
FEATURE                Location/Qualifiers
misc_feature           1..20
                       note = Mouse_Pten_forward
source                 1..20
                       mol_type = other DNA
                       organism = synthetic construct
SEQUENCE: 34
agaccataac ccaccacagc                                         20

SEQ ID NO: 35          moltype = DNA   length = 20
FEATURE                Location/Qualifiers
misc_feature           1..20
                       note = Mouse_Pten_reverse
source                 1..20
                       mol_type = other DNA
                       organism = synthetic construct
SEQUENCE: 35
tacaccagtc cgtccctttc                                         20

SEQ ID NO: 36          moltype = DNA   length = 21
FEATURE                Location/Qualifiers
misc_feature           1..21
                       note = EGFR_seq_forward
source                 1..21
                       mol_type = other DNA
                       organism = synthetic construct
SEQUENCE: 36
cccaggcact tgatgatact c                                       21

SEQ ID NO: 37          moltype = DNA   length = 20
FEATURE                Location/Qualifiers
misc_feature           1..20
                       note = EGFR_seq_reverse
source                 1..20
                       mol_type = other DNA
                       organism = synthetic construct
SEQUENCE: 37
cttgctttgg gtggagagtt                                         20

SEQ ID NO: 38          moltype = DNA   length = 102
FEATURE                Location/Qualifiers
misc_feature           1..102
                       note = Trp53_indel1
source                 1..102
                       mol_type = other DNA
                       organism = synthetic construct
SEQUENCE: 38
tgtgtcttcc cccaggccgg ctctgagtat accaccatcc actacaagta catgtgtaat  60
agctcctgca cttgggggc atgaaccgcc gacctatcct ta                     102

SEQ ID NO: 39          moltype = DNA   length = 98
FEATURE                Location/Qualifiers
misc_feature           1..98
                       note = Trp53_indel2
source                 1..98
                       mol_type = other DNA
                       organism = synthetic construct
SEQUENCE: 39
tgtgtcttcc cccaggccgg ctctgagtat accaccatcc actacaagta catgtgtaat  60
agctcctgtg gggggcatga accgccgacc tatcctta                         98

SEQ ID NO: 40          moltype = DNA   length = 101
FEATURE                Location/Qualifiers
misc_feature           1..101
                       note = Trp53_indel3
source                 1..101
                       mol_type = other DNA
                       organism = synthetic construct
```

-continued

```
SEQUENCE: 40
tgtgtcttcc cccaggccgg ctctgagtat accaccatcc actacaagta catgtgtaat    60
agctcctgca atgggggca tgaaccgccg acctatcctt a                       101

SEQ ID NO: 41            moltype = DNA   length = 110
FEATURE                  Location/Qualifiers
misc_feature             1..110
                         note = Pten_indel1
source                   1..110
                         mol_type = other DNA
                         organism = synthetic construct
SEQUENCE: 41
agaccataac ccaccacagc tagaacttat caaacccttc ttgaagatct tgaccaatgg    60
ctaagtgaag atgacaatca tgttgcagca attcactgta aagctggaaa             110

SEQ ID NO: 42            moltype = DNA   length = 108
FEATURE                  Location/Qualifiers
misc_feature             1..108
                         note = Pten_indel2
source                   1..108
                         mol_type = other DNA
                         organism = synthetic construct
SEQUENCE: 42
agaccataac ccaccacagc tagaacttat caaaccctct gaagatcttg accaatggct    60
aagtgaagat gacaatcatg ttgcagcaat tcactgtaaa gctggaaa              108

SEQ ID NO: 43            moltype = DNA   length = 110
FEATURE                  Location/Qualifiers
misc_feature             1..110
                         note = Pten_indel3
source                   1..110
                         mol_type = other DNA
                         organism = synthetic construct
SEQUENCE: 43
agaccataac ccaccacagc tagaacttat caaacccttc gtgaagatct tgaccaatgg    60
ctaagtgaag atgacaatca tgttgcagca attcactgta aagctggaaa             110
```